(12) United States Patent
Chen

(10) Patent No.: US 12,692,481 B2
(45) Date of Patent: Jul. 28, 2026

(54) BACULOVIRUS EXPRESSION SYSTEM

(71) Applicant: Virovek, Inc., Houston, TX (US)

(72) Inventor: Haifeng Chen, Tomball, TX (US)

(73) Assignee: Virovek, Inc., Houston, TX (US)

( * ) Notice: Subject to any disclaimer, the term of this patent is extended or adjusted under 35 U.S.C. 154(b) by 44 days.

(21) Appl. No.: 16/912,084

(22) Filed: Jun. 25, 2020

(65) Prior Publication Data

US 2020/0407696 A1 Dec. 31, 2020

Related U.S. Application Data

(60) Provisional application No. 63/012,568, filed on Apr. 20, 2020, provisional application No. 62/866,741, filed on Jun. 26, 2019.

(51) Int. Cl.

| | |
|---|---|
| *C12N 7/00* | (2006.01) |
| *A01K 67/68* | (2025.01) |
| *C12N 15/86* | (2006.01) |
| *C12N 15/866* | (2006.01) |
| *C12N 1/00* | (2006.01) |
| *C12R 1/91* | (2006.01) |

(52) U.S. Cl.
CPC .............. *C12N 7/00* (2013.01); *A01K 67/68* (2025.01); *C12N 15/86* (2013.01); *C12N 15/866* (2013.01); *C12N 1/00* (2013.01); *C12N 2710/14041* (2013.01); *C12N 2710/14043* (2013.01); *C12N 2710/14143* (2013.01); *C12N 2710/14144* (2013.01); *C12R 2001/91* (2021.05)

(58) Field of Classification Search
CPC ....................................................... C12N 7/00
See application file for complete search history.

(56) References Cited

U.S. PATENT DOCUMENTS

| | | |
|---|---|---|
| 2008/0004228 A1 | 1/2008 | Berger et al. |
| 2012/0115207 A1 | 5/2012 | Senger et al. |
| 2014/0335063 A1 | 11/2014 | Cannon et al. |
| 2014/0356904 A1 | 12/2014 | Galibert et al. |

FOREIGN PATENT DOCUMENTS

| | | | | |
|---|---|---|---|---|
| JP | 2007/527722 A | 10/2007 | | |
| JP | 2014/522658 A | 9/2014 | | |
| WO | WO2003074714 | * 9/2003 | ............. | C12N 15/86 |
| WO | WO-2005/085456 A1 | 9/2005 | | |
| WO | WO-2011/020710 A2 | 2/2011 | | |
| WO | WO-2013/014294 A2 | 1/2013 | | |
| WO | WO-2014/159831 A1 | 10/2014 | | |
| WO | WO-2019016349 A1 * | 1/2019 | .......... | C07K 14/005 |
| WO | WO-2020/081490 A1 | 4/2020 | | |
| WO | WO-2020/264139 A1 | 12/2020 | | |

OTHER PUBLICATIONS

Kaba et al. (2004, J. Virological Methods, vol. 122, pp. 113-118) (Year: 2004).*
Zhang et al. (2018, BMC Biotech., vol. 18:24, pp. 1-8) (Year: 2018).*
Fernandes et al. (2012, Biotechnology and Bioengineering, vol. 109(11), pp. 2836-2844) (Year: 2012).*
Lee et al. (2006, Biotechnology Letters, vol. 28, pp. 645-650) (Year: 2006).*
BioTechniques (1998, vol. 25, pp. 18-20) (Year: 1998).*
Novagen (2007, Insect Cell Expression, pp. 1-36). (Year: 2007).*
Smith et al. (2009, Molecular Therapy, vol. 17(11), pp. 1888-1896) (Year: 2009).*
Aurnhamme, C. et al., Universal real-time PCR for the detection and quantification of adeno-associated virus serotype 2-derived inverted terminal repeat sequences, Hum Gene Ther. Meth., 23(1): 18-28 (2012).
Datsenko, K. A. and Wanner, B. L., One-step inactivation of chromosomal genes in *Escherichia coli* K-12 using PCR products, PNAS, 97(12):6640-6645 (2000).
Galibert, L. and Merten, O-W., Latest developments in the large-scale production of adeno-associated virus vectors in insect cells toward the treatment of neuromuscular diseases, J Invertebr Pathol., 107:S80-93 (2011).
Galibert, L. et al., Origins of truncated supplementary capsid proteins in rAAV8 vectors produced with the baculovirus system, PLOS One, 13(11): e0207414 (2018).
Grimm, D. and Kay, M. A., From virus evolution to vector revolution: use of naturally occurring serotypes of adeno-associated virus (AAV) as novel vectors for human gene therapy, Curr Gene Ther., 3(4):281-304 (2003).
International Search Report for PCT/US2020/039586, 3 pages (dated Nov. 3, 2020).
Ishimwe, E. et al., Reaching the Melting Point: Degradative Enzymes and Protease Inhibitors Involved in Baculovirus Infection and Dissemination, Virology, 0:637-649 (2015).
Kaba, S. A. et al., Development of a chitinase and v-cathepsin negative bacmid for improved integrity of secreted recombinant proteins, J Virol Methods, 122(1):113-8 (2004).
Kotin, R. M., Large-scale recombinant adeno-associated virus production, Hum Mol Gen., 20(1):R2-R6 (2011).
Luckow, V. A. et al., Efficient Generation of Infectious Recombinant Baculoviruses by Site-Specific Transposon-Mediated Insertion of Foreign Genes into a Baculovirus Genome Propagated in *Escherichia coli*, Journal of Virology, 67(8):4566-4579 (1993).

(Continued)

*Primary Examiner* — Anoop K Singh
*Assistant Examiner* — David A Montanari
(74) *Attorney, Agent, or Firm* — Choate, Hall & Stewart LLP; Rolando Medina

(57) ABSTRACT

The present disclosure relates to a heterologous recombinant baculovirus (rBV) expression system for the production of foreign heterologous proteins in insect cells. This system comprises a recombinant baculovirus backbone within a genome with a deletion in the cathepsin gene into which foreign gene cassettes can be integrated, and an insect cell that can be infected by the Δv-cath-rBV, and in which the foreign proteins and/or viral vectors or particles are expressed.

14 Claims, 37 Drawing Sheets

Specification includes a Sequence Listing.

(56) References Cited

OTHER PUBLICATIONS

Samaranch, L. et al. Adena-associated viral vector serotype 9-based gene therapy for Niemann-Pick disease type A, Science Translational Medicine, 11(506):1-32 (2019).

Thomason, L. C. et al., Recombineering: genetic engineering in bacteria using homologous recombination, Curr Protoc Mol Biol., 106:16.1-39 (2014).

Van Oers, M. M. et al., Thirty years of baculovirus-insect cell protein expression: from dark horse to mainstream technology, Journal of General Virology, 96:6-23 (2015).

Written Opinion for PCT/US2020/039586, 7 pages (dated Nov. 3, 2020).

Xiao, X. et al., Production of High-Titer Recombinant Adeno-Associated Virus Vectors in the Absence of Helper Adenovirus, J Virol., 72(3):2224-2232 (1998).

Zhang, X. et al., High-titer recombinant adeno-associated virus production from replicating amplicons and herpes vectors deleted for glycoprotein H, Hum Gene Ther., 10(15):2527-37 (1999).

Galibert, L. et al., Origins of truncated supplementary capsid proteins in rAAVS vectors produced with the baculovirus system, PLOS ONE, 13(11): 1-20 2018.

Lee, K. et al., Production of a Cellulase in Silkworm Larvae using a Recombinant Bombyx mori nucleopolyhedrovirus lacking the Virus-encoded Chitinase and Cathepsin Genes, Biotechnolo Letters, Kluwer Academic Publishers, Dordrecht, 28(9):645-650 2006.

Slack, J. M. et al., Characterization of v—cath, a cathepsin L-like proteinase expressed by the baculovirus Autographa californica multiple nuclear polyhedrosis virus, Journal Of General Viroloqv, Society For General Microbiology, 76(5): 1091-1098 (1995).

Kost, A. et al., Baculovirus as versatile vectors for protein expression in insect and mammalian cells. Nature Biotechnology. 23:567-575 (2005).

Sik, L. et al., Production of a cellulase in silkworm larvae using a recombinant Bombyx mori nucleopolyhedrovirus lacking the virus-encoded chitinase and cathepsin genes, Biotechnology Letters, 28:645-650 (2006).

* cited by examiner

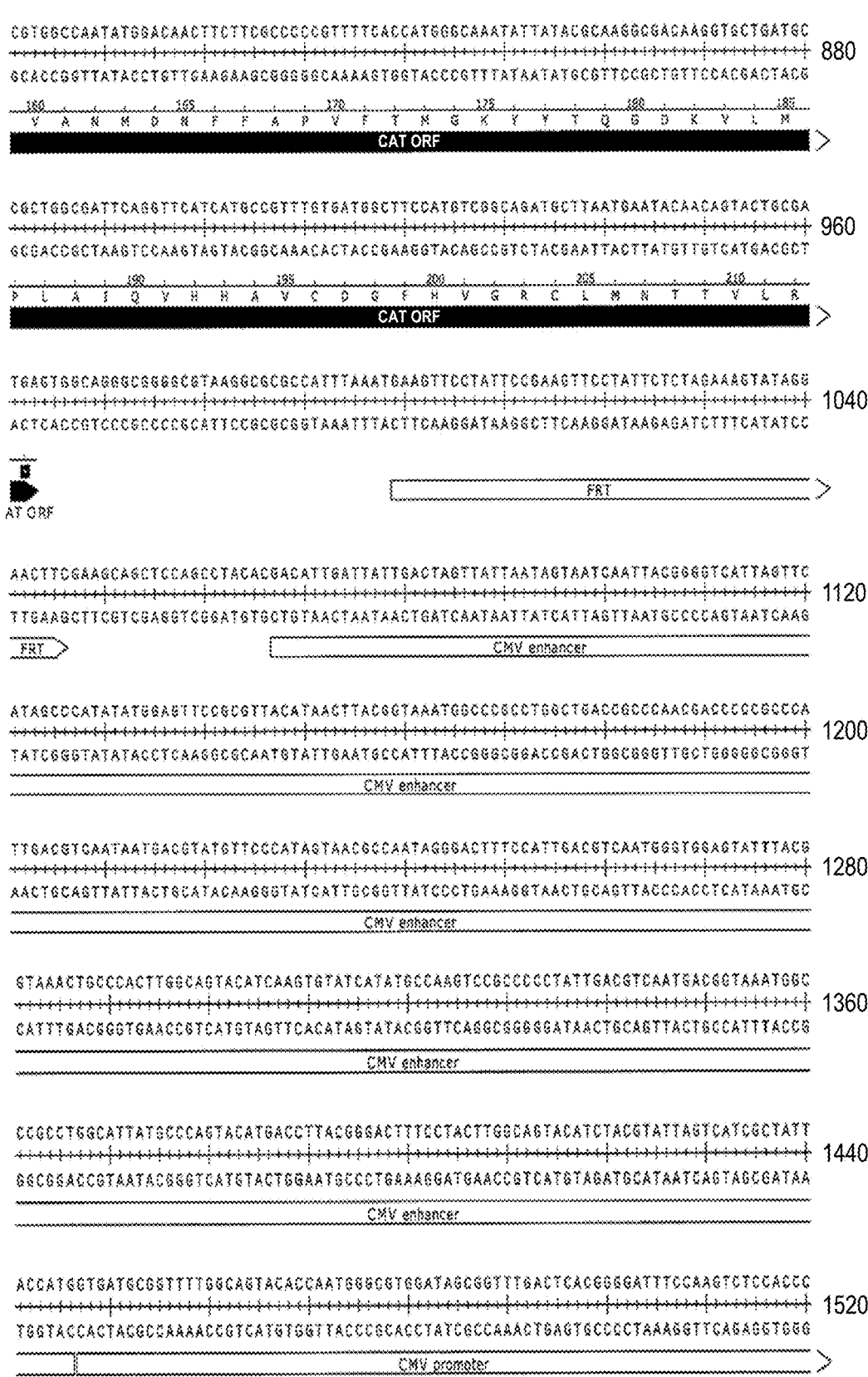

gttcggtcaaggttctggaccagttgcgtgagcgcatacgctacttgcattacagtttacgaaccgaacaggcttatgtc
+--+-+--+--+-+--+--+-+--+--+-+--+--+-+--+--+-+--+--+-+--+--+-+--+--+-+--+--+-+--+--+ 1040
caagccagttccaagacctggtcaacgcactcgcgtatgcgatgacgtaatgtcaaatgcttggcttgtccgaatacag aactggttcgtgccttcatccgtttccacggtgtgcgtcacccggcaaccttgggcagcagcgaagtcgaggcattct
+--+-+--+--+-+--+--+-+--+--+-+--+--+-+--+--+-+--+--+-+--+--+-+--+--+-+--+--+-+--+--+ 1120
ttgacccaagcacggaagtaggcaaaggtgccacacgcagtgggccgttggaaccccgtcgtcgacttcagctccgtaaaga gtcctggctggcgaacgagcgcaaggtttcggtctccacgcatcgtcaggcattggcggccttgctgttcttctacggca
+--+-+--+--+-+--+--+-+--+--+-+--+--+-+--+--+-+--+--+-+--+--+-+--+--+-+--+--+-+--+--+ 1200
caggacctgaccgcttgctcgcgttccaagccagaggtgcgtagcagtccgtaaccgccggaacgacaagacgatgccgt aggtgctgtgcacggatctgccctggcttcaggagatcggtagacctggccgtcgcggcgcttgccggtggtgctgacc
+--+-+--+--+-+--+--+-+--+--+-+--+--+-+--+--+-+--+--+-+--+--+-+--+--+-+--+--+-+--+--+ 1280
tccacgacacgtgcctagacgggaccgaagtcctctagccatctggagtccggcagcgccgcgaacggccaccacgactgg ccggatgaagtggtcgcatcctcggtttctggaaggcgagccatcgtttgttcgccaggactctagctatagttctag
+--+-+--+--+-+--+--+-+--+--+-+--+--+-+--+--+-+--+--+-+--+--+-+--+--+-+--+--+-+--+--+ 1360
ggcctacttcaccaagcgtaggagccaaaagaccttcggtcgtagcaaacaagcgggtcctgagatcgatatcaagatc tggttggcctacgtaccccgtagtggctatggcagggcttgccgccccgacgttggctgcgagccctgggccttcaccga
+--+-+--+--+-+--+--+-+--+--+-+--+--+-+--+--+-+--+--+-+--+--+-+--+--+-+--+--+-+--+--+ 1440
accaaccggatgcatgggcatcaccgataccgtccgaacggcggggctgcaaccgacgctcgggaccccggaagtgggct
                                                    < ═══════════ HSV tk polyA acttggggttggggtgggaaaaggaagaaacgcggcgtattggtcccaatggggtctcggtggggtatcgacagagt
+--+-+--+--+-+--+--+-+--+--+-+--+--+-+--+--+-+--+--+-+--+--+-+--+--+-+--+--+-+--+--+ 1520
tgaaccccaaccccacccctttcccttctttgcgccgcataaccagggttacccagagccacccatagctgtctca
───────────────────────────── HSV tk polyA ───────────────────── gccagccctgggaccgaacccgcgtttatgaacaaacgaccaacaccgtgcgtttatttctgtcttttattgccgt
+--+-+--+--+-+--+--+-+--+--+-+--+--+-+--+--+-+--+--+-+--+--+-+--+--+-+--+--+-+--+--+ 1600
cggtcgggacccctggcttggggcgcaaatacttgttgctgggttgtgggcacgcaaaataagacagaaaataacggca
< ───────────────────────────── HSV tk polyA ───────────────── catagcgcgggttccttccggtattgtctccttccgtgttcagttagcctcacccatctccggtaccgcatgctcctt
+--+-+--+--+-+--+--+-+--+--+-+--+--+-+--+--+-+--+--+-+--+--+-+--+--+-+--+--+-+--+--+ 1680
gtatcgcgcccaaggaaggccataacagaggaaggcacaaagtcaatcggaggggggtagagggccatggcgtacgaggaa
< ══════════════════ HSV tk polyA ══════════════════               ⤶ Rep cagagcgagtgtcctcgagccaatctgaacaataccatcggcagccataccctgatttaaatcattattgttcaaagat
+--+-+--+--+-+--+--+-+--+--+-+--+--+-+--+--+-+--+--+-+--+--+-+--+--+-+--+--+-+--+--+ 1760
gtctctctcacaggagctcggttagacttgttatggtagccgtcggtatggactaaatttagtaaataacaagtttcta
< ████████████████████████████ Rep ████████████████████████████ gcagtcatccaaatccacattgaccagatcgcaggcagtgcaagccgtctggcacccttccatgatatgatgaatgtagc
+--+-+--+--+-+--+--+-+--+--+-+--+--+-+--+--+-+--+--+-+--+--+-+--+--+-+--+--+-+--+--+ 1840
cgtcagtaggcttagggtgtaactggtctagcgtccgtcacgttcgcagaccgtggaagggtactatactacttacatcg
< ████████████████████████████ Rep ████████████████████████████ acagtttctgatacgcctttttgacgacagaaacgggttgagattctgacacggaaagcactctaaacgtctttctgt
+--+-+--+--+-+--+--+-+--+--+-+--+--+-+--+--+-+--+--+-+--+--+-+--+--+-+--+--+-+--+--+ 1920
tgtcaaagactatgcggaaaaactgctgtctttgcccaactctaagactgtgccctttcgtgagatttgtcagaaagaca
< ████████████████████████████ Rep ████████████████████████████ ccgtgagtgaagcagatatttgaattctgattcattctctcgcattgtctgcagggaaacagcatcagattcatgccac
+--+-+--+--+-+--+--+-+--+--+-+--+--+-+--+--+-+--+--+-+--+--+-+--+--+-+--+--+-+--+--+ 2000
ggcactcacttcgtctataaacttaagactaagtaagagagcgtaacagacgtcccttttgtcgtagtctaagtacgggtg
< ████████████████████████████ Rep ████████████████████████████

*Fig. 4B (cont)*

M, protein ladder; lanes 1 & 5, AAV9 control; lanes 2& 6, AAV7m8-GFP; lanes 3 & 7, AAV8-GFP; lanes 4 & 8, AAV6-GFP; lanes 2 – 4, AAV vectors produced with WT-rBVs; lanes 6 – 8, AAV vectors produced with Δ-v-cath rBVs. Arrows indicate degraded capsid proteins.

BACULOVIRUS EXPRESSION SYSTEM

CROSS REFERENCE TO RELATED APPLICATIONS

This application claims priority to U.S. Provisional Application Ser. No. 62/866,741, filed Jun. 26, 2019, and U.S. Provisional Application Ser. No. 63/012,568, filed Apr. 20, 2020, each of which is incorporated herein by reference in its entirety.

FIELD OF THE INVENTION

The present invention is in the fields of molecular biology, virology, and gene therapy. More particularly, the invention relates to a baculovirus system for the synthesis of recombinant protein in insect cells.

BACKGROUND OF THE INVENTION

Gene therapy has been developed to treat a number of disorders such as cancer and genetic related diseases. Such treatment includes the use of recombinant proteins which have been produced in mammalian systems using viral vectors.

Currently there are several technologies in the field of recombinant protein and viral vector production which use different means of introducing foreign genes into the host cells. For example, traditional methods of introducing AAV genes utilize the transfection of mammalian cell lines such as HEK-293 or Hela cells with triple or double plasmids (Xiao et al. (1998) *J. Virol.* 72(3): 2224-2232; Grimm et al. (2003) *Mol. Ther.* 7(6): 839-850). Another technique utilizes Herpes simplex virus (HSV) to infect mammalian cells, e.g., for AAV manufacturing (Zhan et al. (1999) *Hum. Gene Ther.* 10(15): 2527-2537).

Unfortunately, AAV production in these systems has been low. For example, AAV vector production has been hampered by the difficulties of generating sufficient HSV seed stocks. Also, the manufacture of AAV vectors is difficult to scale up due to the inherent properties of adherent mammalian cells and low yield of AAV production. Thus, large scale production of AAV in these systems sufficient to obtain enough material for clinical trials has been problematic.

Other recombinant protein and viral production systems include the use of baculovirus in insect cells (Chen (2008) Mol. Ther. 16(5): 924-930; Kotin (2011) *Hum. Mol. Genet.* 20(R1): R2-6). The baculovirus expression vector (or bacmid) system (BEVS) is a well-established method for the production of recombinant proteins to be used as vaccines, therapeutic molecules, or diagnostic reagents (van Oers (2015) *J. Gen. Virol.* 96(Pt 1): 6-23) This system provides increased AAV production yields relative to other AAV production technologies (Galibert et al. (2011) *J. Invertebr. Pathol.* 107 Suppl: S80-93). However, this method has encountered AAV capsid degradation. Removal of the baculovirus chitinase (chiA) and cathepsin (v-cath) genes has been reported to improve the integrity of secreted recombinant proteins and prevented AAV8 capsid degradation (Galibert et al. (2018) *PLoS One* 13(11): e0207414). However, removal of the chiA gene also removes the chitinase activity that is required to breakdown the chitin, a high molecular weight linear polymer of N-acetyl-D-glucosamine units synthesized in the insect cells (IIshimwe et al. (2015) *Virol.* 479-480: 637-649). Without chiA activity, the AAV particles produced in these insect cells are difficult to isolate from the viscous cell lysate, thereby reducing the recovery of AAV particles.

Therefore, improved expression systems that produce useful amounts of recombinant viral vectors and proteins that are not degraded and that have useful levels of activity are needed.

SUMMARY OF THE INVENTION

It has been discovered that a recombinant baculovirus (rBV) having a genome with a deletion of the v-cath gene enables the expression of AAV capsid proteins with higher structural integrity, from a cassette that has been integrated into the rBV genome. Therefore, rAAV isolated from insect-cells infected with cathepsin-deleted rBV have higher infectivity than rAAV isolated from insect cells infected with rBV containing cathepsin.

These discoveries have been exploited to develop the present disclosure, which, in part, is directed to a recombinant baculovirus system, the components thereof, and to methods using a specifically deleted rBV for foreign protein expression.

In one aspect, the disclosure provides a recombinant baculovirus (rBV) DNA backbone, comprising: a chitinase gene; a deletion of the v-cath gene; and a DNA fragment enabling integration of one or more foreign protein expression cassettes into the backbone, such that the one or more foreign protein or proteins expressed in an insect cell are less degraded than they are when expressed from a rBV backbone without the deletion.

In some embodiments, the DNA fragment comprises a DNA sequence homologous to two sequences flanking the one or more foreign protein expression cassettes in a donor plasmid. In certain embodiments, the DNA fragment is derived from bMON14272. In some embodiments, the DNA fragment comprises an origin of replication. In specific embodiments, the origin of replication is a mini-F-replicon, ColE1, oriC, OriV, OriT or OriS. In certain embodiments, the DNA fragment further comprises a reporter gene. In specific embodiments, the reporter gene is LacZα.

In some embodiments, the rBV DNA backbone further comprises a selection marker expression gene cassette integrated into the cath-v deletion. In particular embodiments, the selection marker expression gene cassette comprises an antibiotic-resistance gene, and in particular embodiments, the antibiotic-resistance gene is a kanamycin-resistant gene, an ampicillin-resistant gene, a tetracycline-resistant gene, a gentamicin-resistant gene, a blasticidin-resistance gene, a chloramphenicol-resistance gene, a streptomycin-resistance gene, or a geneticin-resistance gene. In other embodiments, the selection marker expression gene cassette comprises a selection marker gene encoding a visually detectable protein. In some embodiments, the selection marker gene encodes a colorimetric, fluorescent, chromatographic, chemiluminescent, or luminescent protein.

The present discourse also provides a recombinant baculovirus (rBV) genome, comprising: a rBV DNA backbone; and a foreign protein expression cassette. The rBV DNA backbone comprises: a chitinase gene; a deletion of the v-cath gene; and a DNA fragment enabling integration of one or more foreign protein expression cassettes into the backbone, such that the one or more foreign protein or proteins expressed in an insect cell are less degraded than they are when expressed from a rBV backbone without the deletion. The foreign protein gene cassette comprises: at least one foreign protein gene; an insect cell promoter operably linked to the at least one foreign gene; and two DNA sequences, enabling the foreign protein expression cassette to integrate into the rBV DNA backbone.

In some embodiments, the at least one foreign protein gene in the foreign expression cassette compromises at least one viral protein gene and/or at least one mammalian protein gene. In certain embodiments, the viral protein gene encodes an AAV protein, an adenoviral protein, a retroviral protein, an SV40 protein, or a Herpes simplex viral protein. In specific embodiments, the foreign protein expression cassette comprises a sequence encoding at least one AAV capsid protein. In certain embodiments, the at least one AAV protein is VP1, VP2, VP3, and/or a Rep protein, and in particular embodiments, the at least one SV40 protein is VP1 major capsid protein.

In some embodiments, the foreign protein expression cassette comprises an insect promoter, such as a polyhedron, p10, or p6.9 insect promoter, operably linked to the at least one foreign protein gene.

In some embodiments, the two DNA sequences enabling the foreign protein expression cassette to integrate into the DNA backbone are homologous to the DNA sequence in the rBV DNA backbone. In particular embodiments, the two DNA sequences enabling the foreign protein expression cassette to integrate into the DNA backbone. are transposable elements. In certain embodiments, the two DNA sequences enabling the foreign protein expression cassette, to integrate into the DNA backbone are Tn7R and Tn7L.

In another aspect, the disclosure provides a recombinant baculovirus (rBV) genome, comprising: a rBV DNA backbone and a foreign protein cassette. The rBV backbone comprises: a chitinase gene; a deletion of the v-cath gene; a selection marker gene cassette integrated into the cath-v deletion; and a DNA fragment enabling integration of one or more foreign protein expression cassettes into the backbone, such that the one or more foreign protein or proteins expressed in an insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In yet another aspect, the disclosure provides a recombinant baculovirus (rBV) vector or particle comprising: an rBV genome; and at least one baculoviral capsid protein. The rBV genome comprises: an rBV DNA backbone; and a foreign protein expression cassette, the rBV DNA backbone comprising: a chitinase gene; a deletion of the v-cath gene; and a DNA fragment enabling integration of one or more foreign protein expression cassettes into the backbone, such that the one or more foreign protein or proteins expressed in an insect cell are less degraded than they are when expressed from a rBV backbone without the deletion, and the foreign protein gene cassette comprises: at least one foreign protein gene; an insect cell promoter operably linked to the at least one foreign gene; and two DNA sequences, enabling the foreign protein expression cassette to integrate into the rBV DNA backbone. In some embodiments, the rBV genome comprises a rBV backbone comprising a foreign protein expression cassette encoding at least one AAV capsid protein.

In still another aspect, the disclosure provides a recombinant baculovirus (rBV) vector or particle comprising: a rBV genome; and at least one baculoviral capsid protein. The rBV genome comprises: an rBV DNA backbone comprising: a chitinase gene; a deletion of the v-cath gene; a selection marker gene cassette integrated into the cath-v deletion; and a DNA fragment enabling integration of one or more foreign protein expression cassettes into the backbone, such that the one or more foreign protein or proteins expressed in an insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the one or more foreign protein expression cassettes to integrate into the rBV DNA backbone. In some embodiments, the rBV genome comprises a rBV backbone comprising a foreign protein expression cassette encoding at least one AAV capsid protein.

The disclosure also provides an insect cell comprising a recombinant baculovirus (rBV) vector or particle comprising: a rBV genome; and at least one baculoviral capsid protein. The rBV genome comprises: an rBV DNA backbone comprising: a chitinase gene; a deletion of the v-cath gene; and a DNA fragment enabling integration of one or more foreign protein expression cassettes into the backbone, such that the one or more foreign protein or proteins expressed in an insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In some embodiments, the insect cell is an Sf9, Sf21, S2, *Trichoplusia ni*, E4a, or BTI-TN-5B1-4 cell. In particular embodiments, the insect cell further comprises at least one foreign protein expressed from the foreign protein expression cassette in the rBV backbone of the rBV genome of the rBV vector or particle, and in certain embodiments, the at least one foreign protein is at least one AAV capsid protein.

Also provided herein is an insect cell comprising a recombinant baculovirus vector or particle, comprising: a rBV genome; and at least one baculoviral capsid protein. The rBV genome comprises: an rBV DNA backbone comprising: a chitinase gene; a deletion of the v-cath gene; a selection marker gene integrated into the cath-v deletion; and a DNA fragment enabling integration of one or more foreign protein expression cassettes into the backbone, such that the one or more foreign proteins expressed in an insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In some embodiments, the insect cell is an Sf9, Sf21, S2, *Trichoplusia ni*, E4a, or BTI-TN-5B1-4 cell. In particular embodiments, the insect cell further comprises at least one foreign protein expressed from the foreign protein expression cassette in the rBV backbone of the rBV genome of the rBV vector or particle, and in certain embodiments, the at least one foreign protein is at least one AAV capsid protein.

In another aspect, the disclosure provides a heterologous expression system comprising: an rBV vector or particle; and an insect cell. The rBV vector or particle comprises: an rBV genome; and at least one baculoviral capsid protein, the rBV genome comprising: an rBV DNA backbone comprising: a chitinase gene; a deletion of the v-cath gene; and a DNA fragment enabling integration of one or more foreign protein expression cassettes into the backbone, such that the one or more foreign protein or proteins expressed in the insect cell are less degraded than they are when expressed from the rBV backbone without the deletion; and a foreign protein expression cassette, the foreign protein expression cassette comprising: at least one foreign protein gene; an insect cell promoter operably linked to the at least one foreign gene; and two DNA sequences, enabling the foreign protein expression cassette to integrate into the rBV DNA backbone. The insect cell in the system is susceptible to infection, and capable of expressing the at least one foreign protein encoded, by the rBV backbone in the rBV vector or particle.

In some embodiments. rBV vector or particle comprises an rBV backbone comprising a foreign protein expression cassette, the foreign protein expression cassette comprising a sequence encoding at least one AAV capsid protein. In some embodiments, the insect cell is an Sf9, Sf21, S2, *Trichoplusia ni*, E4a, or BTI-TN-5B1-4 cell.

In yet another aspect, the disclosure provides a heterologous expression system comprising: an rBV vector or particle; and an insect cell. The recombinant baculovirus vector or particle comprises: an rBV genome; and at least one baculoviral capsid protein. The rBV genome comprises: an rBV DNA backbone comprising: a chitinase gene; a deletion of the v-cath gene; a selection marker cassette integrated into the cath-v deletion; and a DNA fragment enabling integration of one or more foreign protein expression cassettes into the backbone, such that the one or more foreign protein or proteins expressed in the insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone. The insect cell of the system is susceptible to infection, and capable of expressing the at least one foreign protein encoded, by the rBV backbone in the rBV vector or particle.

In some embodiments. rBV vector or particle comprises an rBV backbone comprising a foreign protein expression cassette, the foreign protein expression cassette comprising a sequence encoding at least one AAV capsid protein. In some embodiments, the insect cell is an Sf9, Sf21, S2, *Trichoplusia ni*, E4a, or BTI-TN-5B1-4 cell.

The present disclosure also provides a non-viscous insect cell lysate, comprising: the recombinant baculovirus (rBV) genome; and at least one foreign protein encoded by the rBV genome and expressed in the lysate. The rBV genome comprises: an rBV DNA backbone comprising: a chitinase gene; a deletion of the v-cath gene; and a DNA fragment enabling integration of one or more foreign protein expression cassettes into the backbone, such that the one or more foreign protein or proteins expressed in an insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In some embodiments, the at least one foreign protein encoded by the rBV genome is at least one AAV capsid protein. In some embodiment the insect cell lysate is derived from an Sf9, Sf21, S2, *Trichoplusia ni*, E4a, or BTI-TN-5B1-4 insect cell infected with the rBV genome.

In another aspect, the disclosure provides a non-viscous insect cell lysate, comprising: a recombinant baculovirus (rBV) genome; and at least one foreign protein encoded by the rBV genome and expressed in the lysate. The rBV genome comprises: an rBV DNA backbone comprising: a chitinase gene; a deletion of the v-cath gene; a selection marker gene cassette integrated into the cath-v deletion; and a DNA fragment enabling integration of one or more foreign protein expression cassettes into the backbone, such that the one or more foreign proteins expressed in an insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In some embodiments, the at least one foreign protein encoded by the rBV genome is at least one AAV capsid protein. In some embodiments, the insect cell lysate is derived from an Sf9, Sf21, S2, *Trichoplusia ni*, E4a, or BTI-TN-5B1-4 insect cell infected with the rBV genome.

In still another aspect, the present disclosure provides a method of producing a foreign protein in an insect cell, comprising: infecting the insect cell with a recombinant baculovirus (rBV) vector or particle; culturing the infected cell under conditions conducive for the expression of the at least one foreign protein gene; and isolating the foreign protein. particle comprising: a rBV genome; and at least one baculoviral capsid protein. The rBV vector or particle comprises: an rBV DNA backbone comprising: a chitinase gene; a deletion of the v-cath gene; and a DNA fragment enabling integration of one or more foreign protein expression cassettes into the backbone, such that the one or more foreign protein or proteins expressed in the insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In some embodiments, the insect cell is lysed to isolate the foreign protein. In certain embodiments, the foreign protein is at least one recombinant AAV capsid protein.

The disclosure also provides a recombinant AAV capsid protein produced by this method.

In another aspect, the present disclosure provides a method of producing a foreign protein in an insect cell, comprising: infecting the insect cell with a recombinant baculovirus (rBV) vector or particle; culturing the infected cell under conditions conducive for the expression of the at least one foreign protein gene; and isolating the foreign protein. The rBV vector or particle comprises: an rBV DNA backbone comprising: a chitinase gene; a deletion of the v-cath gene; a selection marker gene cassette integrated into the cath-v deletion; and a DNA fragment enabling integration of one or more foreign protein expression cassettes into the backbone, such that the one or more foreign protein or proteins expressed in the insect cell are less degraded than they are when expressed from a rBV backbone without the deletion. The foreign protein expression cassette comprises: at least one foreign protein gene; an insect cell promoter operably linked to the at least one foreign gene; and two DNA sequences, enabling the foreign protein expression cassette to integrate into the rBV DNA backbone.

In some embodiments, the insect cell is lysed to isolate the foreign protein. In certain embodiments, the foreign protein is at least one recombinant AAV capsid protein.

The disclosure also provides a recombinant AAV capsid protein produced by this method.

DESCRIPTION OF THE DRAWING

The foregoing and other objects of the present disclosure, the various features thereof, as well as the disclosure itself may be more fully understood from the following description, when read together with the accompanying drawings in which:

FIG. 1A is a diagrammatic representation of the recombinant baculovirus (rBV) DNA backbones or bacmids according to the disclosure showing the deletion of the v-cath gene between nucleotides 107,034 and 107,904 and its replacement with the CAT expression cassette flanked by two FRTs and a green fluorescent protein (GFP) expression cassette, wherein;

FIGS. 2A-2C are schematic representations of representative DNA junction sequences between the v-cath and CAT and GFP expression cassettes in the Δv-cath rBV backbone, where bases 51-1066 are the CAT expression cassette, 1067-3223 are the GFP expression cassette, and 1-50 and 3224-3275 bases are the remaining v-cath sequence, and where the sequence is set forth in SEQ ID NO:12;

FIGS. 4A-4H are schematic representations of the DNA sequences of the foreign protein expression cassette described in FIG. 3, including a representative polh insect promoter, and the Tn7L and Tn7R sites for integration of the foreign protein expression cassette into the recombinant baculovirus Δv-cath rBV DNA backbone, and where the sequence is set forth in SEQ ID NO:13;

FIGS. 10A-10C show GFP-expressing AAV vectors produced by WT-rBVs, FIGS. 10D-10F show GFP-expressing AAV vectors produced by v-cath-deleted rBV, where 10A and 10D are AAV7m8-GFP, 10B and 10E are AAV8-GFP, and 10C and 10F are AAV6-GFP;

DESCRIPTION

Figure 1A:
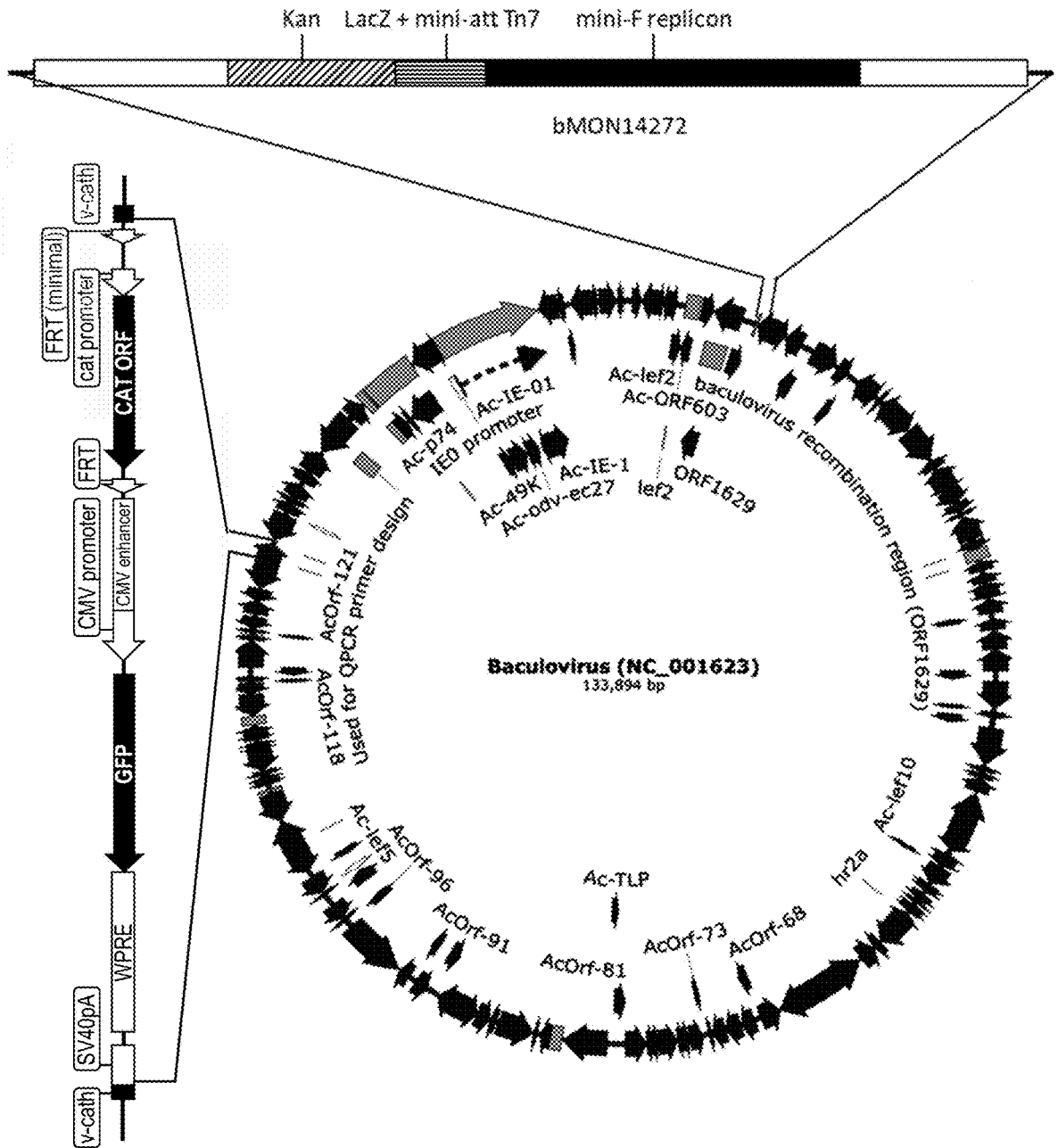

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

The term "bacmid" refers to a shuttle vector that can be propagated in both *E. coli* and insect cells. A Δv-cath bacmid is a bacmid having a deletion in the v-cathepsin gene.

The term "recombinant baculovirus (rBV) DNA backbone" refers to a bacmid comprising a baculovirus genome as described by Luckow et al. (1993) *J. Virol.* 67(8):4566, that contains a bacterial origin of replication, an antibiotic resistant gene and the mini-att Tn7 site enabling the integration of an expression cassette into the backbone, and a cathepsin gene.

A Δv-cath rBV backbone or Δv-cath DNA backbone is a bacmid having a deletion in the v-cathepsin gene and into which foreign gene cassettes including viral and/or mammalian genes can be inserted. The terms "Δv-cath" and "a deletion in the v-cath (or cathepsin) gene" are used interchangeably herein.

The term "recombinant baculovirus (rBV) genome" is used herein to mean a baculovirus DNA genome including at least one expression cassette encoding at least one foreign protein. When the rBV genome includes a deleted v-cath gene, it is referred to as "Δv-cath-rBV genome".

An rBV vector refers to a recombinant baculovirus carrying a rBV genome and encased within the baculovirus capsid and which is capable of infecting an insect cell.

A "viral particle" refers to a biological entity comprising a shell formed by the expression and operative assembly within a cell, of capsid proteins, and genetic information in the form of RNA or DNA.

A "selection marker gene" encompasses those genes that encode a selection marker protein useful for identifying or selecting an *E. coli* cell that has been successfully transformed by the bacmid, and for identifying and selecting an insect or mammalian cell successfully infected by the rBV such as, but not limited to, a colorimetric protein or an antibiotic-resistance protein.

A "selection marker gene cassette" is a DNA sequence that encodes a non-native selection marker gene operably linked to an *E. coli* or insect promoter and comprising two insertion sequences which has enabled the integration of the cassette into the DNA backbone.

As used herein, the term "foreign protein" refers to a protein not encoded by a wild type baculovirus genome. Such proteins include, but are not limited to, non-insect proteins such as viral proteins and mammalian proteins.

A "foreign protein expression cassette" is a DNA sequence encoding at least one non-baculoviral protein such as a viral and/or mammalian protein, operably linked to an insect promoter enabling expression in an insect cell, and may further comprise a DNA sequence operably linked to a mammalian gene promoter enabling expression in a mammalian cell. The foreign gene expression cassette may further link to a selection marker gene and insertion sequences enabling integration of the foreign gene expression cassette into the recombinant baculovirus DNA backbone.

A "donor plasmid" is a DNA vector or plasmid that has the foreign protein expression cassette flanked by recombination elements such as transposons which can be used to transfer the foreign protein expression cassette to the bacmid to generate the recombinant baculovirus (rBV) genome.

The present disclosure relates to a recombinant baculovirus (rBV) expression system for the production of foreign heterologous proteins, including mammalian proteins, in insect cells and which are useful for gene therapy. This system comprises a recombinant baculovirus genome with a deletion in the cathepsin gene (Δv-cath-rBV) into which foreign gene cassettes can be integrated, and an insect cell that can be infected by the Δv-cath-rBV, and in which the foreign proteins and/or viral vectors or particles are expressed or produced.

Insect cells infected by rBV with chitinase A and v-cathepsin deletion are commonly used for expression of recombinant proteins, particularly AAV capsid proteins (Kaba et al. (2004) *J. Virol. Meth.* 122(1): 113-118; Galibert et al. (2018) *PLoS One* 13(11): e0207414). However, the deletion of both chiA and v-cath results in a gelatinous lysate due to the absence of chitinase A which cleaves the chitin-rich membrane of insect cells. Isolation of proteins from this viscous lysate is decreased owing gelatinous nature of the lysate.

The present system unexpectedly enables the efficient production of foreign proteins of interest, and viral vectors and particles, without degradation and in an amount and infectivity level sufficient to be useful for therapeutic purposes. Relative to systems using infection of insect cells with rBV having both a chitinase A gene deletion and a v-cathepsin gene deletion, use of the present system rBV leads to greater AAV yields and greater structural integrity of the AAV capsid, especially in certain AAV mutants. This system also enables the direct expression of mammalian genes in an insect cell.

Δv-cath-Baculovirus Backbone

Figure 1B:
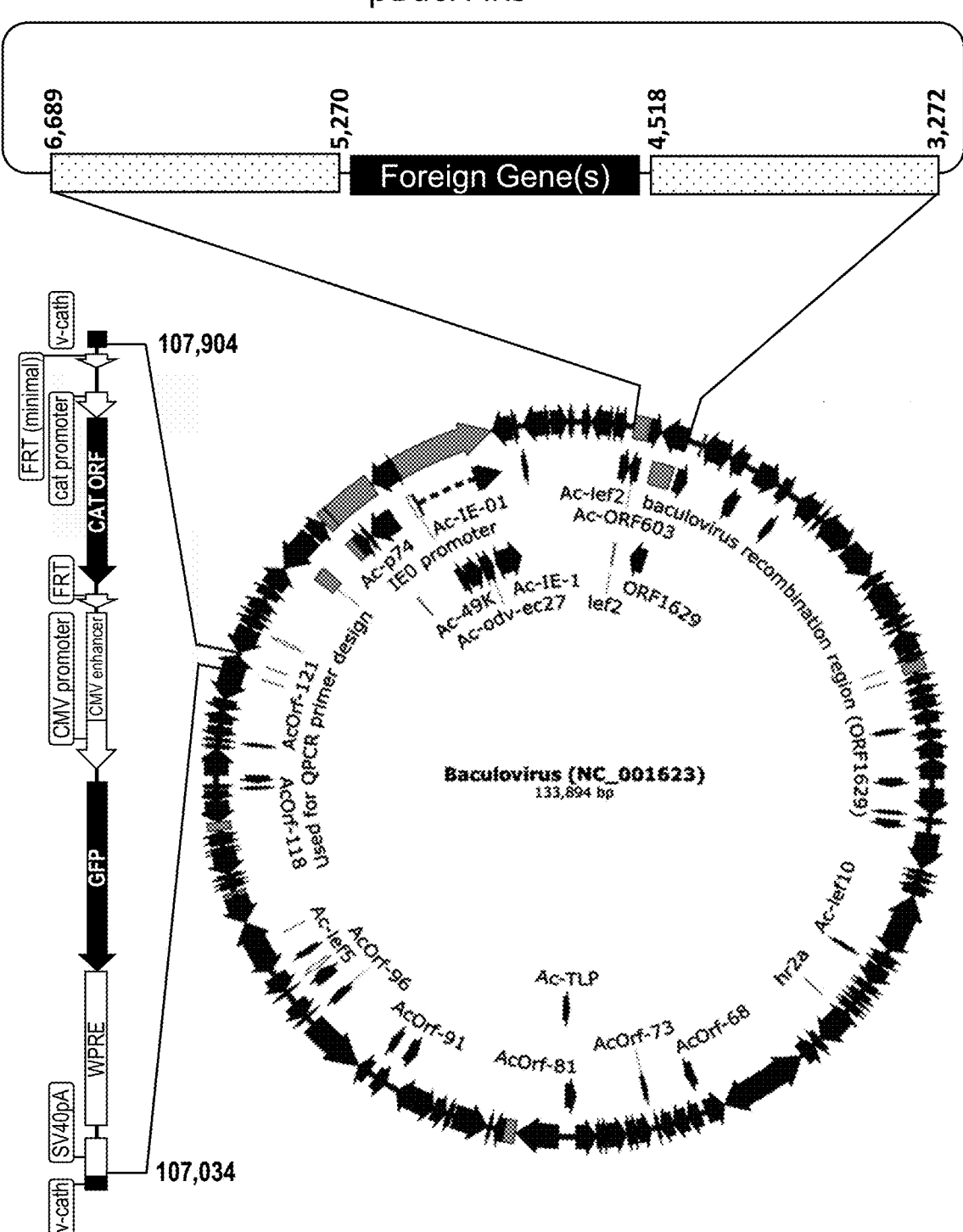
FIG. 1B is a diagrammatic representation of the recombinant baculovirus (rBV) DNA backbones or bacmids according to the disclosure showing the deletion of the v-cath gene between nucleotides 107,034 and 107,904 and its replacement with the CAT expression cassette flanked by two FRTs and a green fluorescent protein (GFP) expression cassette, wherein a foreign protein expression cassette(s) can be integrated into the rBV DNA backbone through homologous recombination.

A baculovirus DNA backbone according to the disclosure comprises a deletion of the cathepsin gene. One Δv-cath DNA backbone according to the disclosure is shown in FIGS. 1A and 1B. The deletion is between nucleotides 107,034 and 107,904 based on GenBank ID NC_001623. In one nonlimiting example shown in FIG. 1A, the Δv-cath-DNA backbone includes the mini-att Tn7 site that enables the insertion of one or more foreign gene cassettes for the expression of foreign proteins and nucleic acids of interest. In another example showing in FIG. 1B, the Δv-cath-rBV DNA backbone's DNA fragments from nucleotides 3272 to 4518, and 5270 to 6689 based on GenBank ID NC_001623 were cloned into the pBacPAK shuttle plasmid to flank the one or more foreign gene cassettes such that the one or more foreign gene cassettes can be inserted into the Δv-cath-rBV DNA backbone through homologous recombination.

Figure 11:
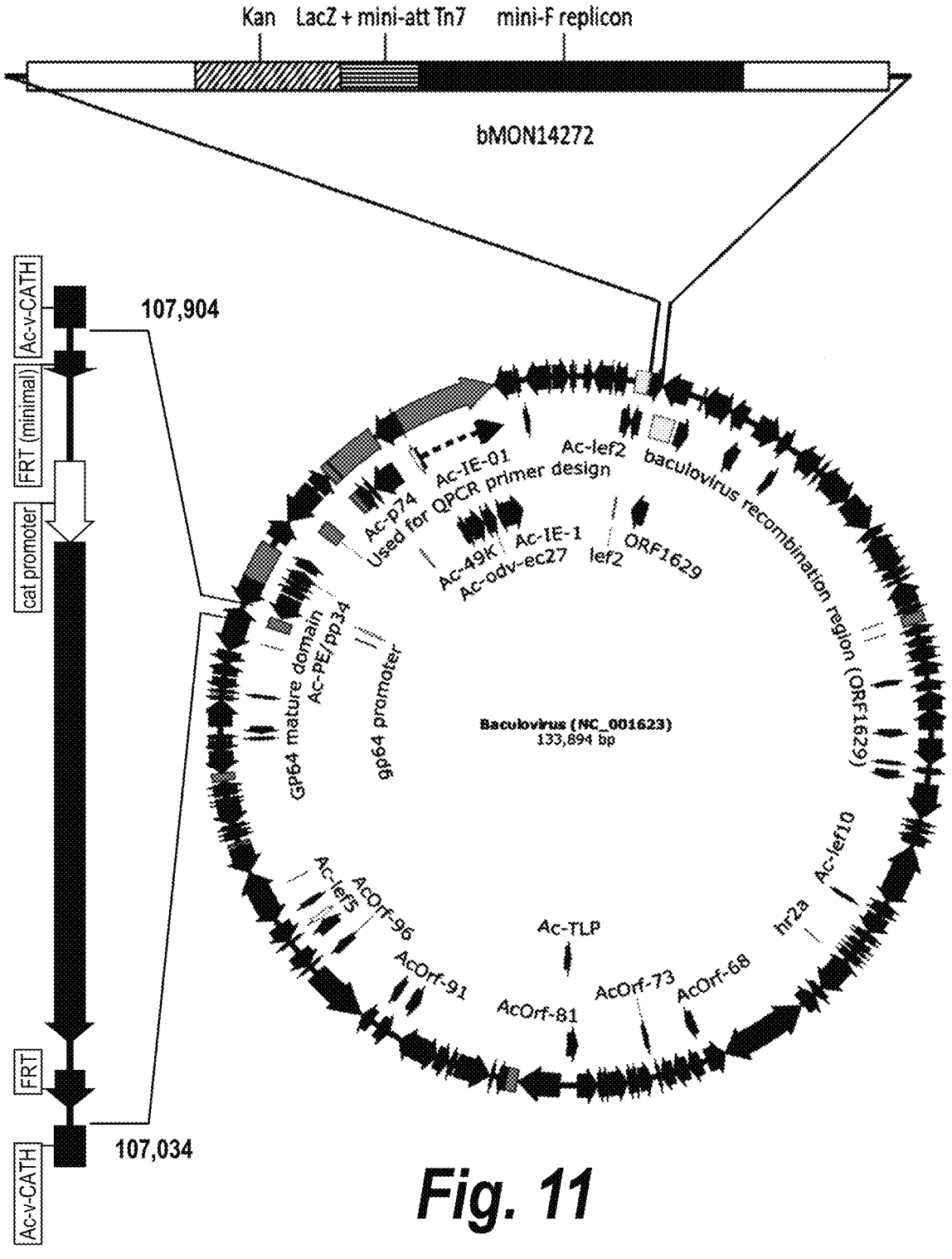
FIG. 11 is a diagrammatic representation of Δv-cath recombinant baculovirus backbone containing the CAT expression cassette flanked by two FRTs only.
Figure 12:
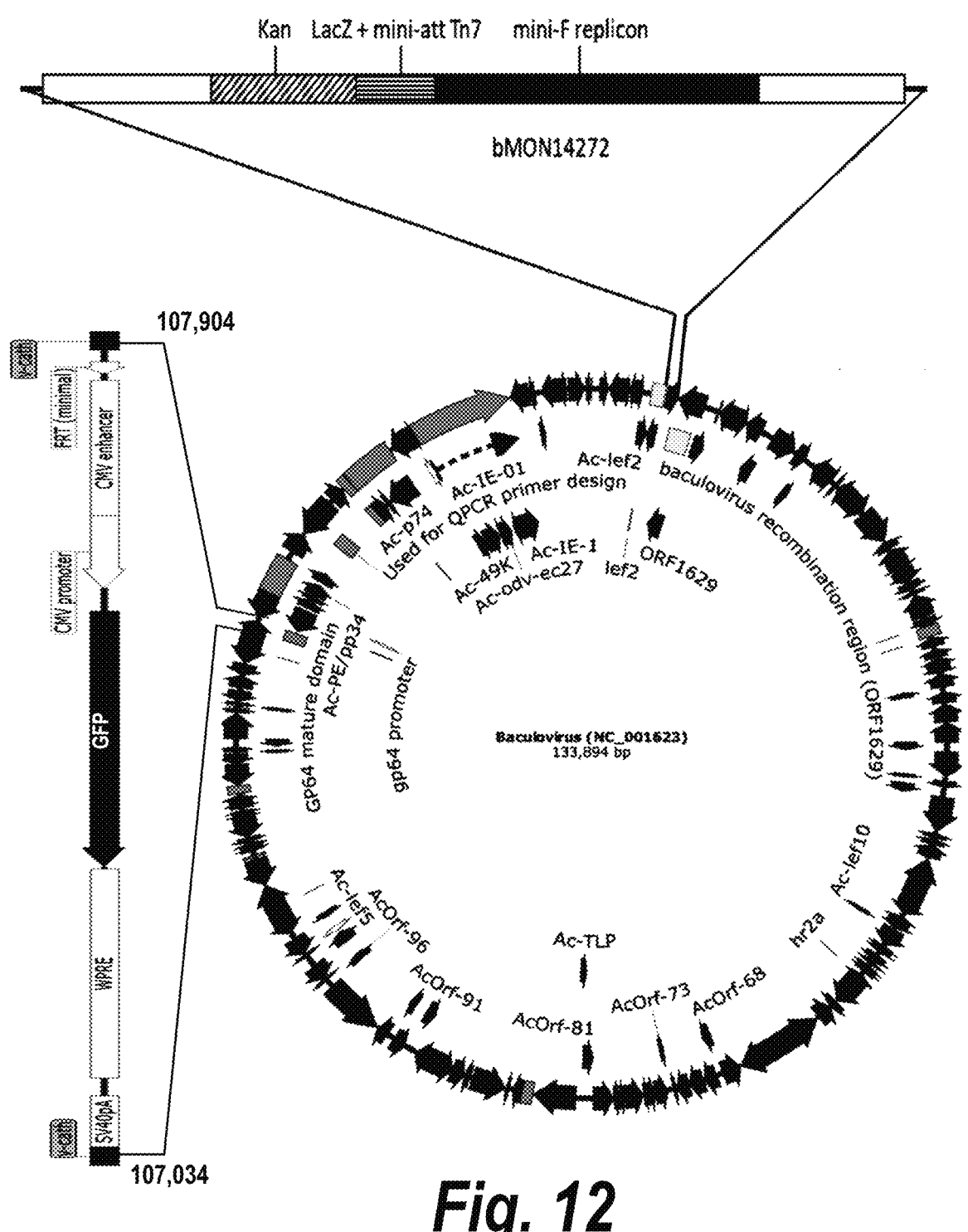
FIG. 12 is a diagrammatic representation of the baculovirus backbone Δv-cath rBV after removal of the CAT expression cassette, leaving behind the GFP expression cassette and a single FRT site.

In some rBV backbones, a selection marker cassette is integrated into the Δv-cath deletion. For example, the v-cath deletion can be replaced with a chloramphenicol (CAT)

selection marker expression cassette (CAT promoter-CAT ORF-polyA) flanked by two FRTs (see FIG. 11). Alternatively, in FIG. 1B, the Δv-cath deletion has been replaced with a CAT selection marker expression cassette flanked by two FRTs and a selection marker, green fluorescent protein (GFP) expression cassette (CMV promoter-GFP-WPRE-polyA). The latter expression marker selection cassette is useful for tracking successful infection into an insect cell. The cassette alternatively may include genes encoding other selection markers such as other colorimetric, fluorescent, or chemiluminescent marker proteins. Useful fluorescent marker proteins include, but are not limited to, red fluorescent protein, yellow fluorescent protein, blue fluorescent protein, and luciferase. Useful colorimetric marker proteins include, but are not limited to lacZ β-galactosidase and secreted embryonic alkaline phosphatase (SEAP). Useful antibiotic resistance genes are also acceptable selection marker. Such genes include, but are not limited to, a kanamycin-resistant gene, an ampicillin-resistant gene, a tetracycline-resistant gene, a gentamicin-resistant gene, a blasticidin-resistant gene, or a chloramphenicol-resistant gene.

Figure 13:
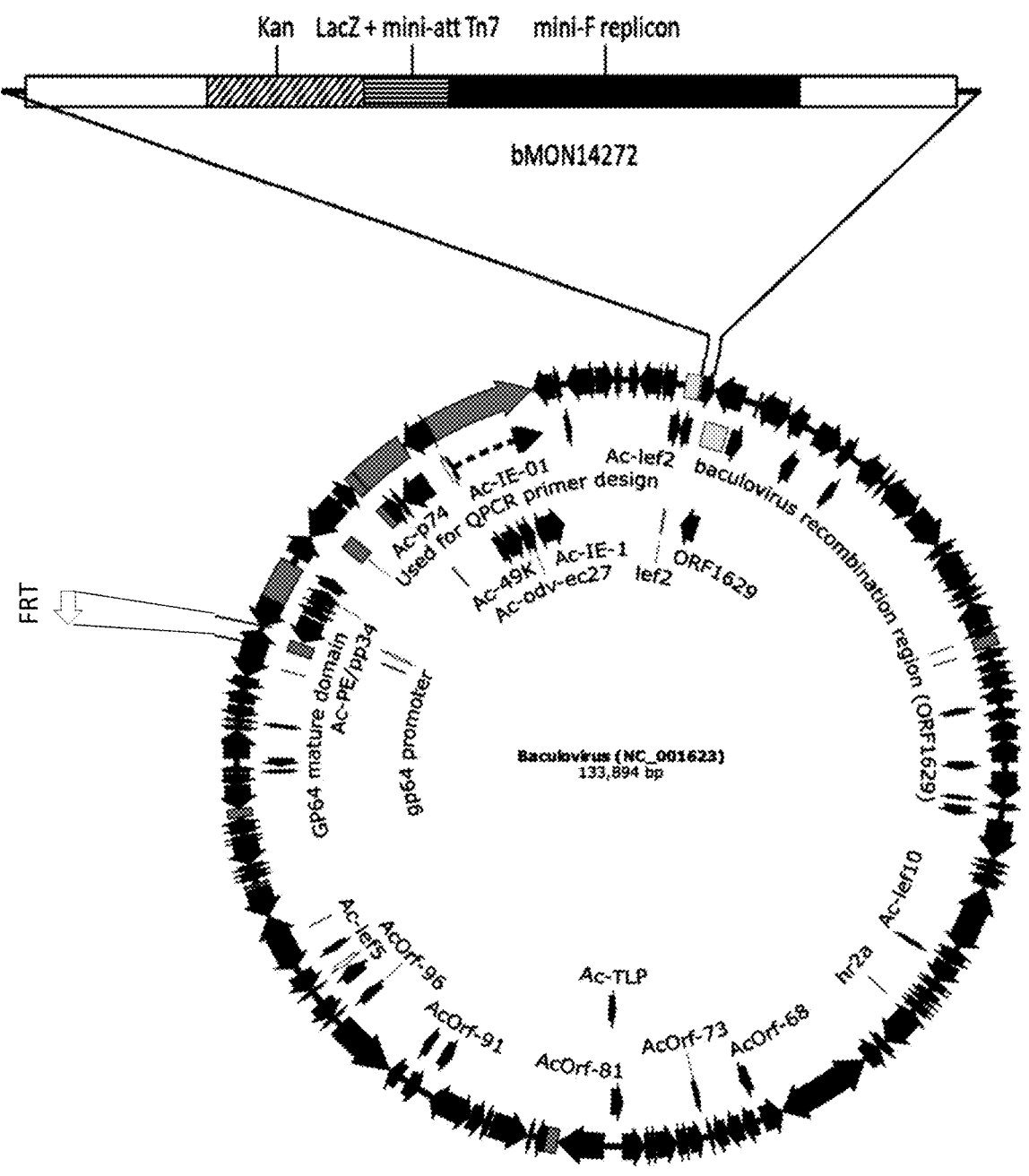
FIG. 13 is a diagrammatic representation of the Δv-cath rBV backbone after removal of the CAT expression cassette, leaving one FRT site behind.

Another representative Δv-cath rBV DNA backbones is shown in FIG. 13. This backbone does not include a selection marker gene expression cassette. It can be created from Δv-cath rBV DNA backbone containing the CAT expression cassette as depicted in FIG. 11 through genomic engineering with the FLP-FRT recombination technology that can remove the CAT expression cassette between the FRT sites, leaving only one FRT site in the Δv-cath rBV DNA backbone.

The rBV Δv-cath DNA backbone according to the disclosure also comprises a chitinase gene (at positions 105,282 to 106,937 in FIGS. 1A, 1B, 11, 12, and 13. In addition, the backbone comprises a DNA fragment enabling integration of one or more foreign protein expression cassettes into the backbone. Useful examples of this fragment include, but are not limited to, the Tn7 transposon fragment. For example, in the rBV DNA backbone shown in FIG. 1A, this fragment is located within the LacZ coding sequence between the kanamycin gene and mini-F replication sequence in the bMON14272 rBV DNA backbone.

Δv-cath Backbone Synthesis

The Δv-cath backbone can be created from a bacmid comprising the WT baculovirus genome (AcMNPV (NC_001623) into which the composite fragment (Kan LacZ+mini-att Tn7 mini-F replication) is inserted into the polyhedrin region as depicted in bMON14272, (see EXAMPLE 2) or synthesized de novo.

Figure 2A:
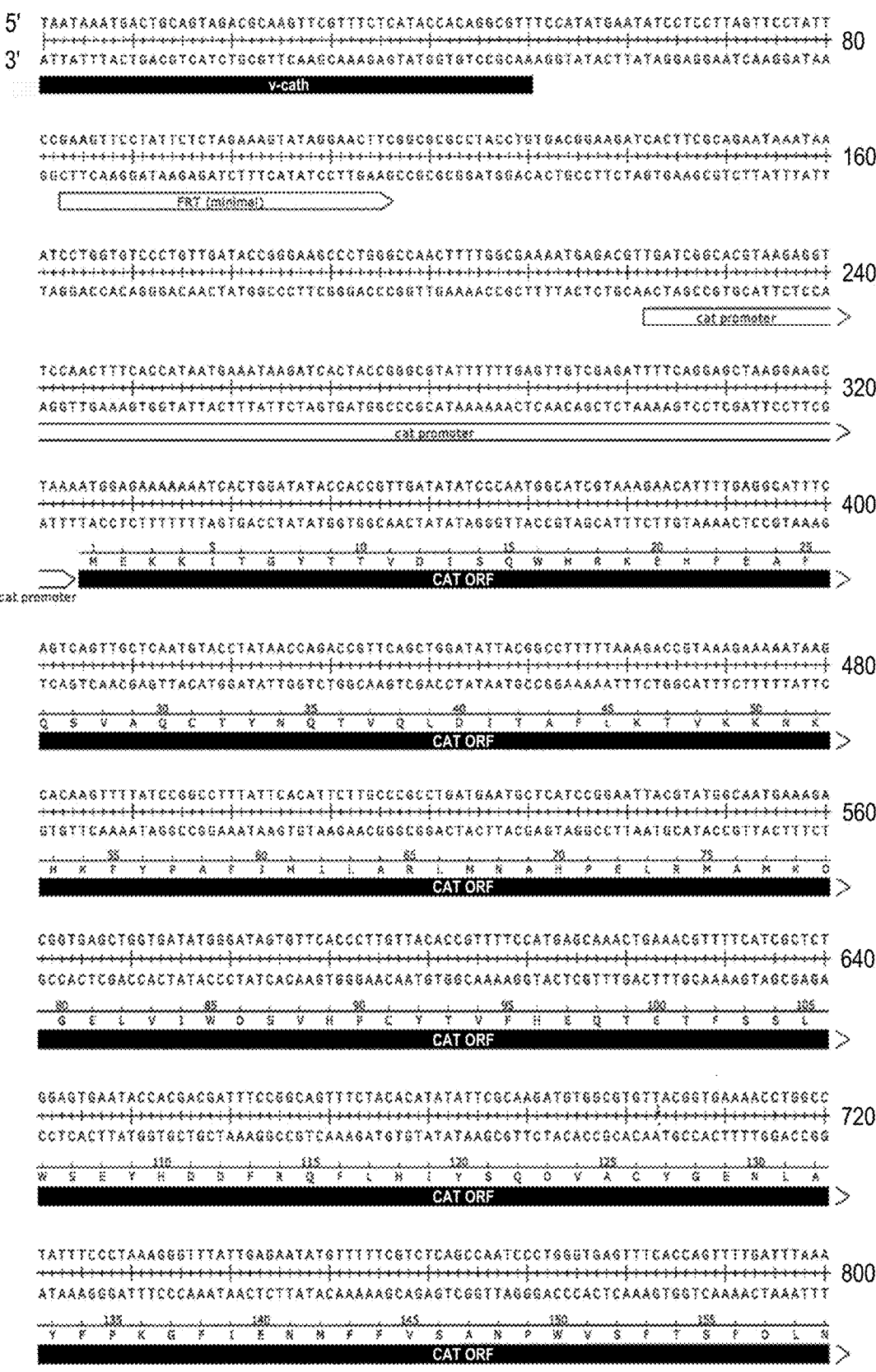
Figure 2C:
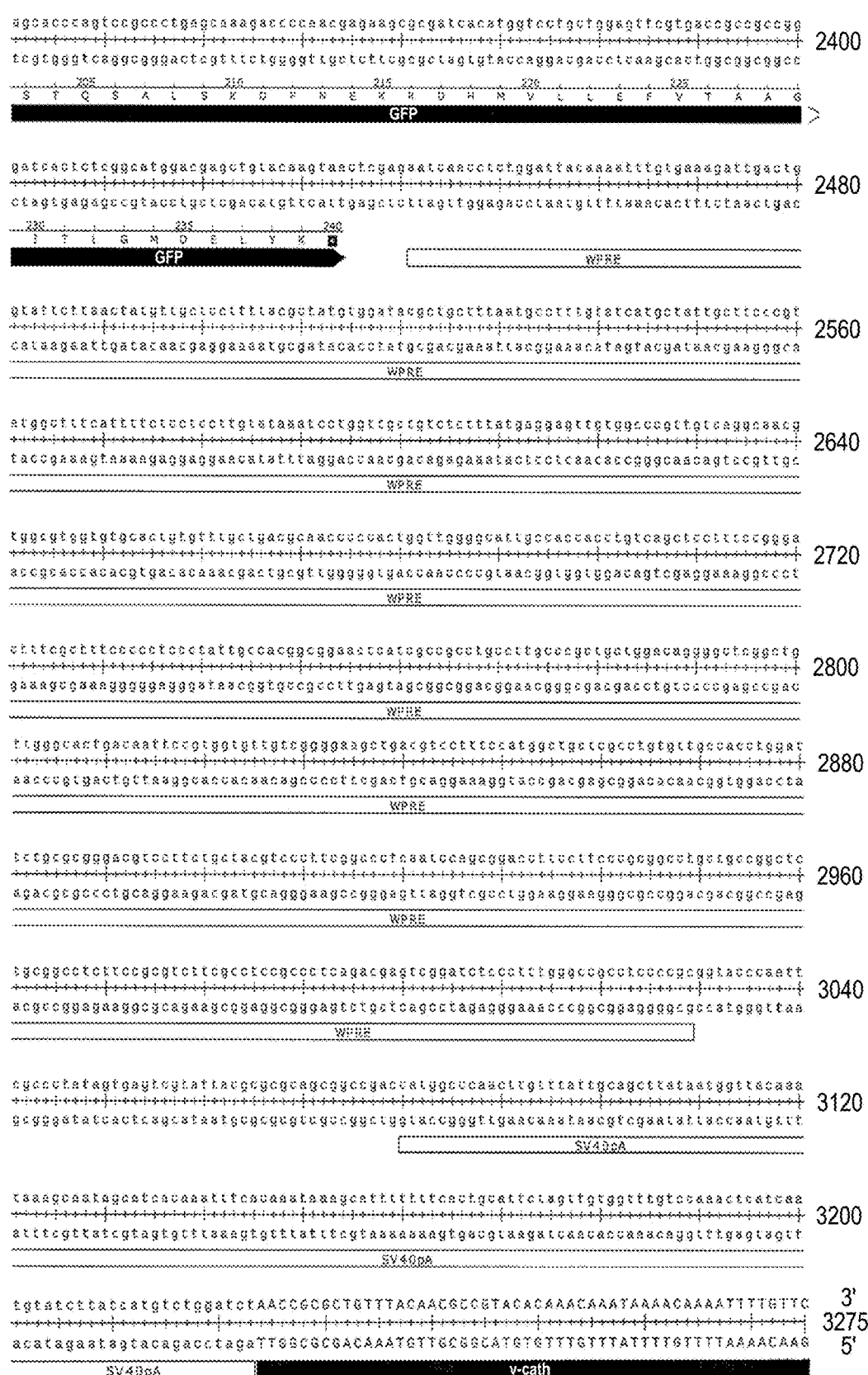
Figure 3:
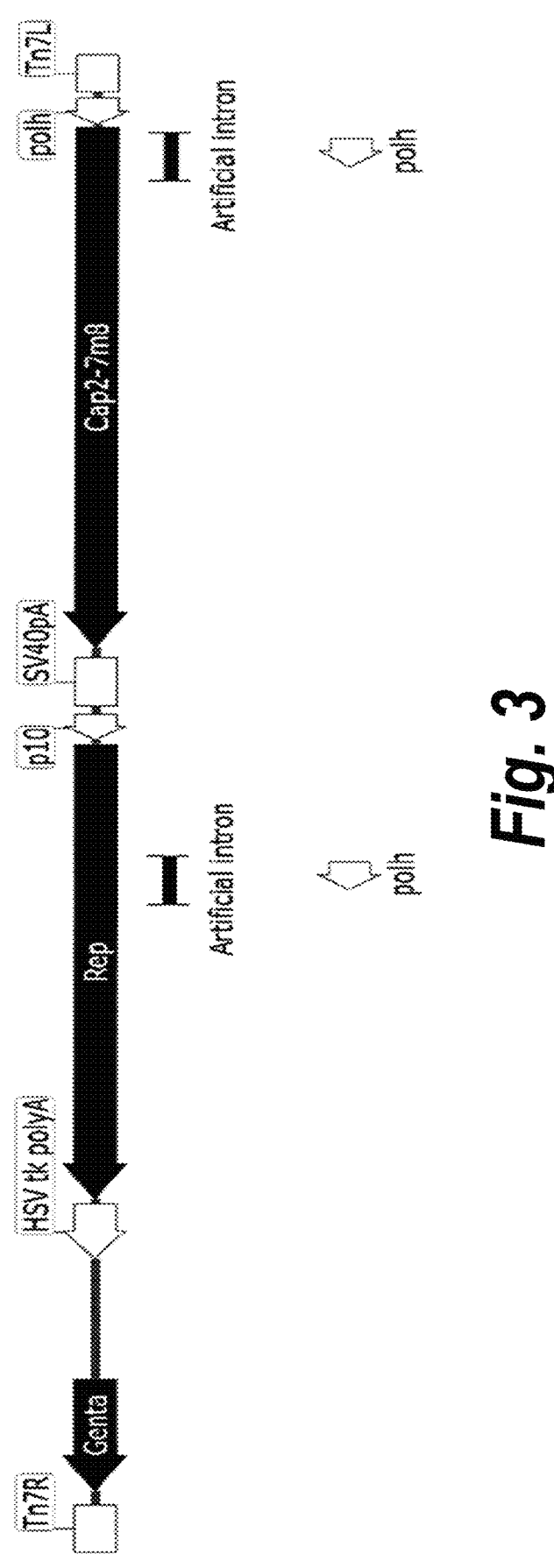
FIG. 3 is a diagrammatic representation of the design of an exemplary foreign protein expression cassette including an insect polyhedrin promoter (polh), AAV Rep and Cap (foreign protein) genes, and a selection marker gene gentamicin (Genta), flanked by Tn7R and Tn7L sites for integration of the cassette into the recombinant baculovirus Δv-cath rBV DNA backbone.
Figure 4A:
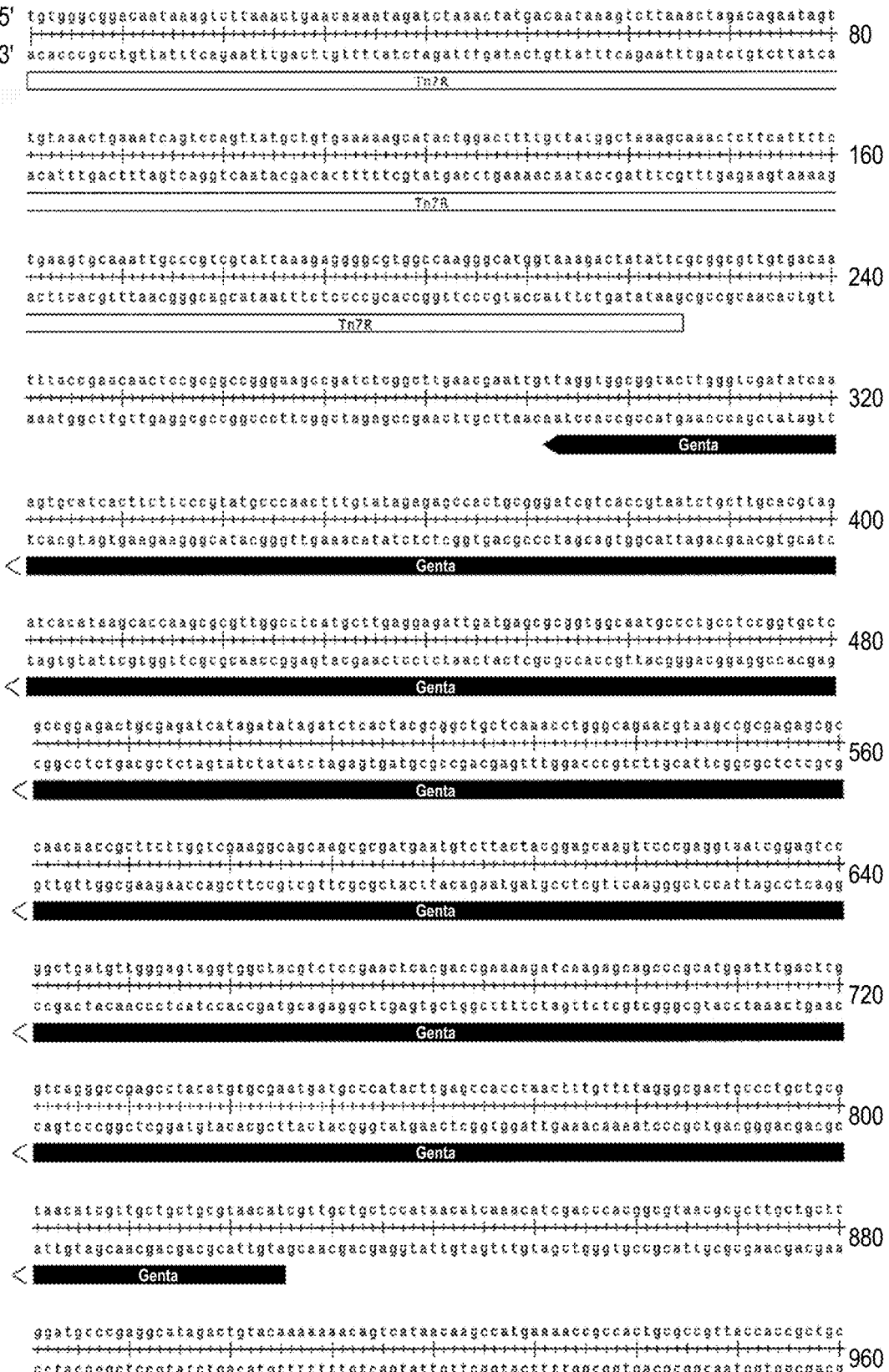
Figure 4C:
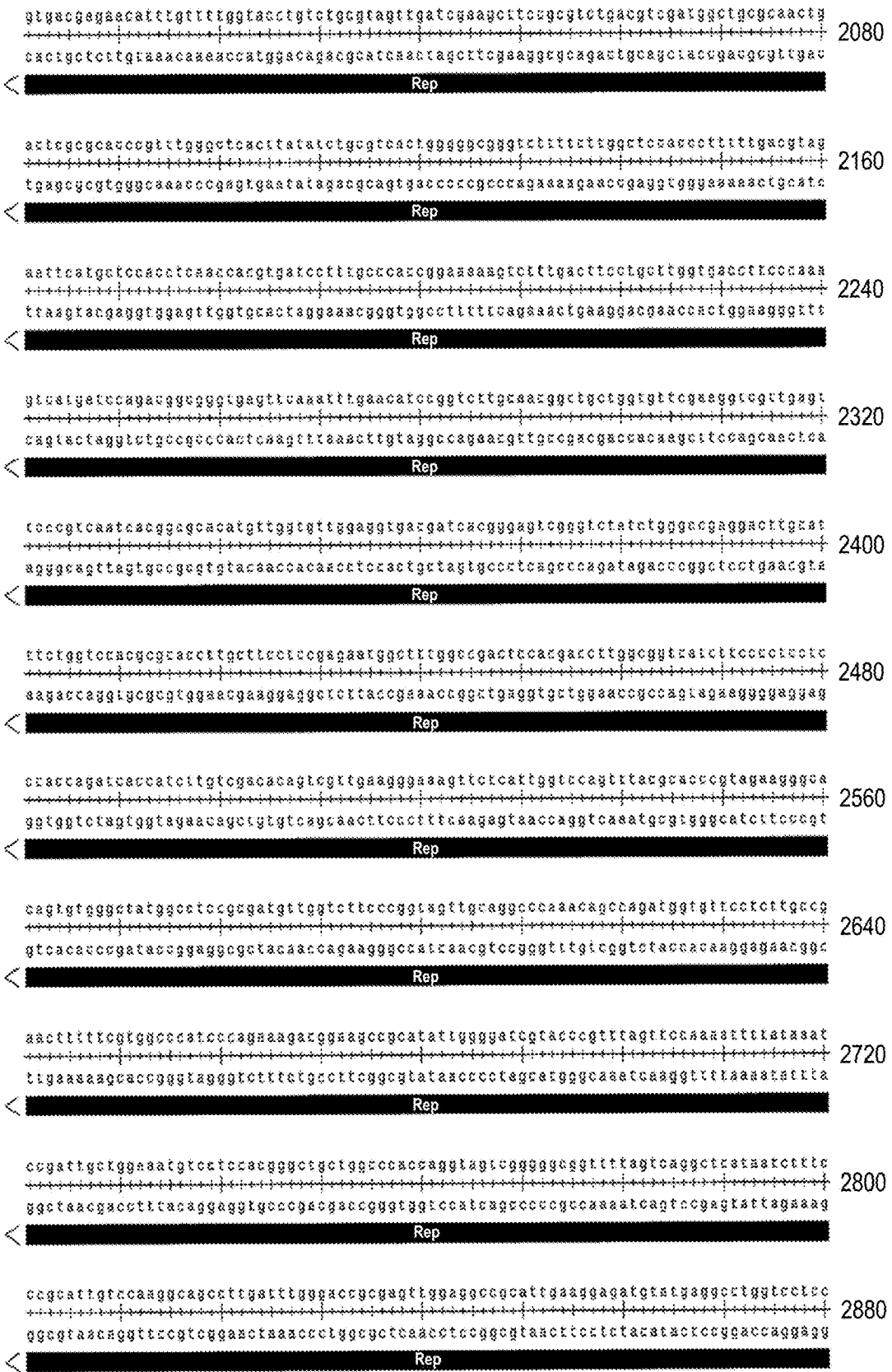
Figure 4D:
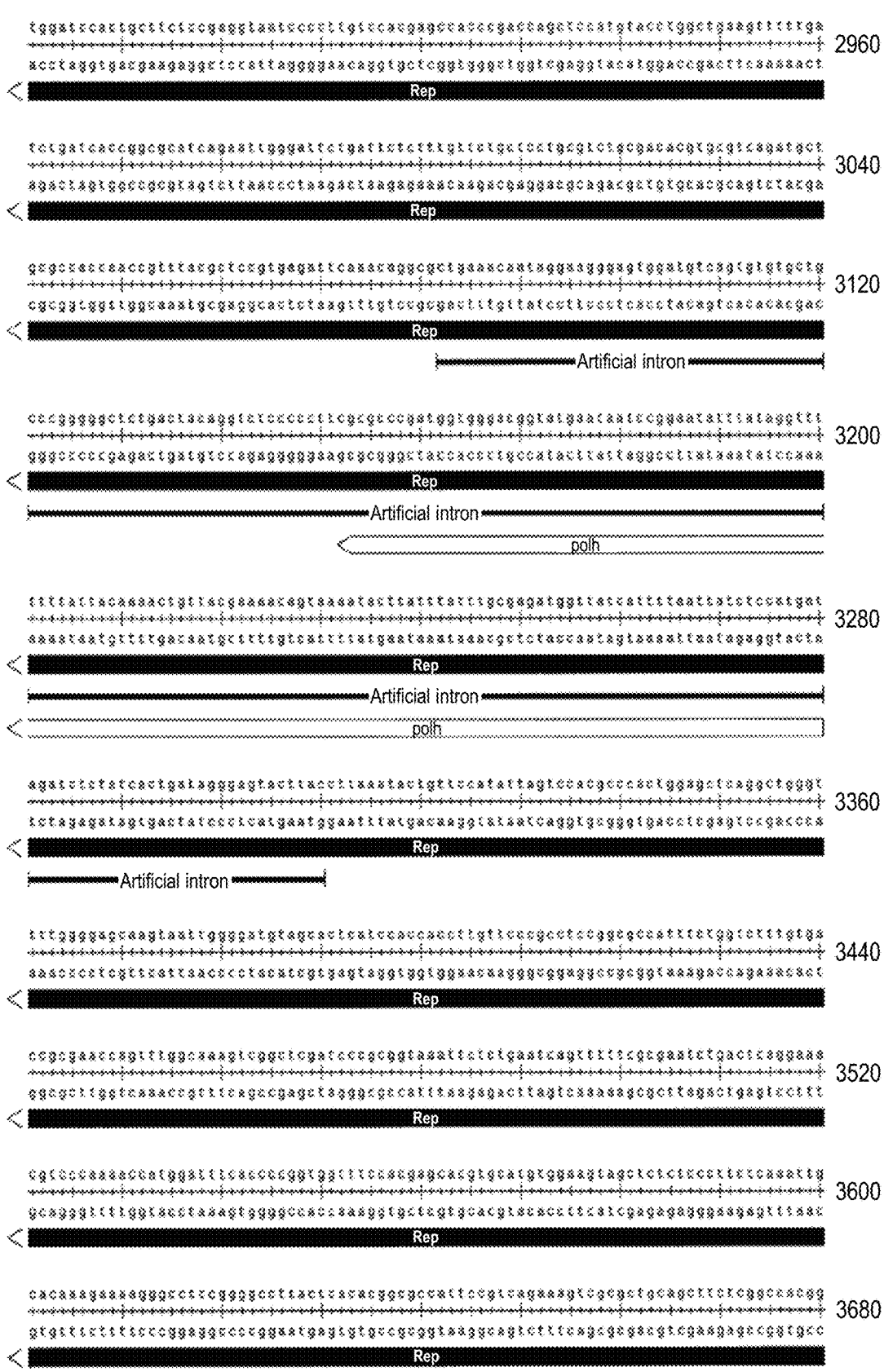
Figure 4E:
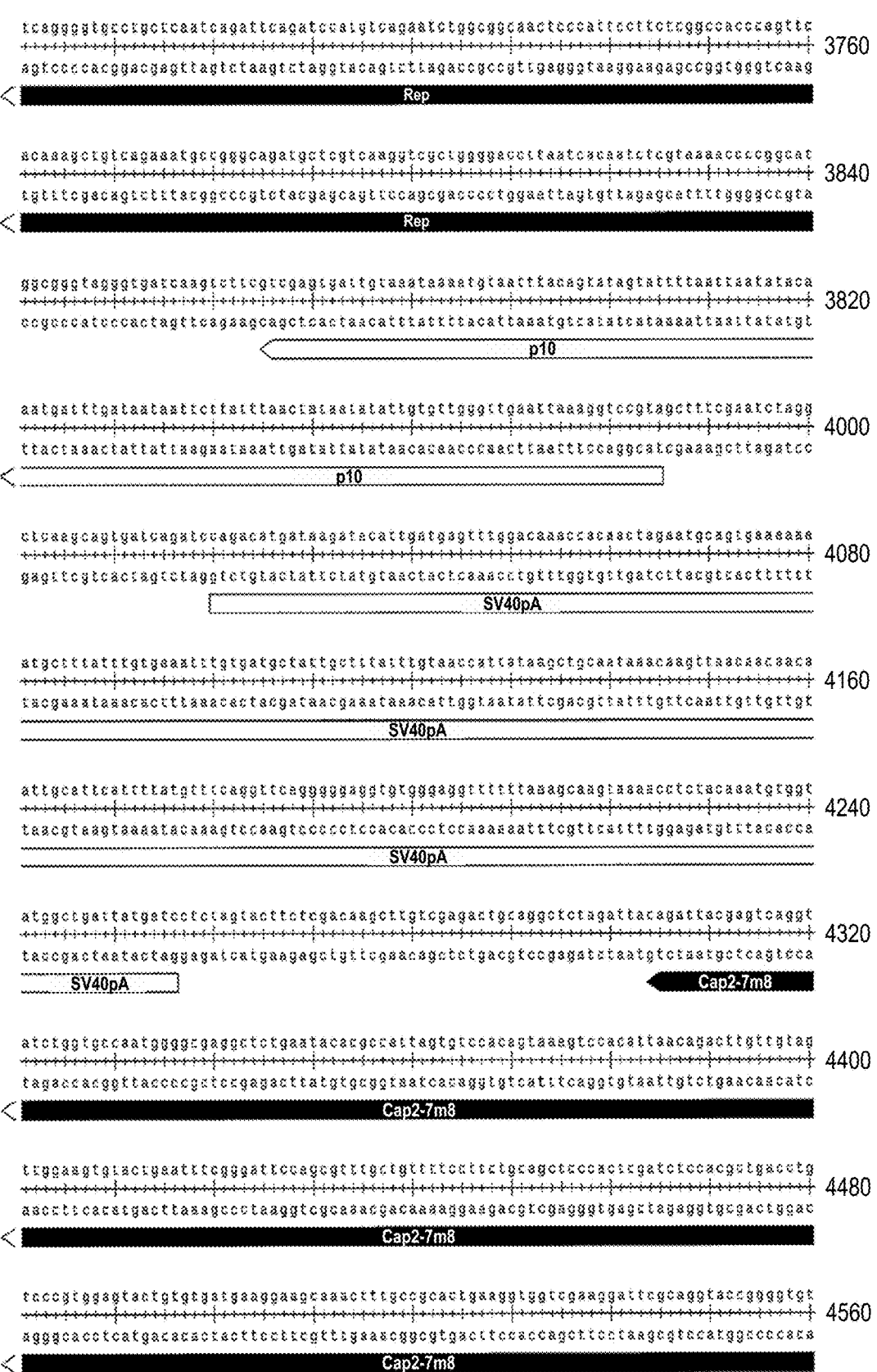
Figure 4F:
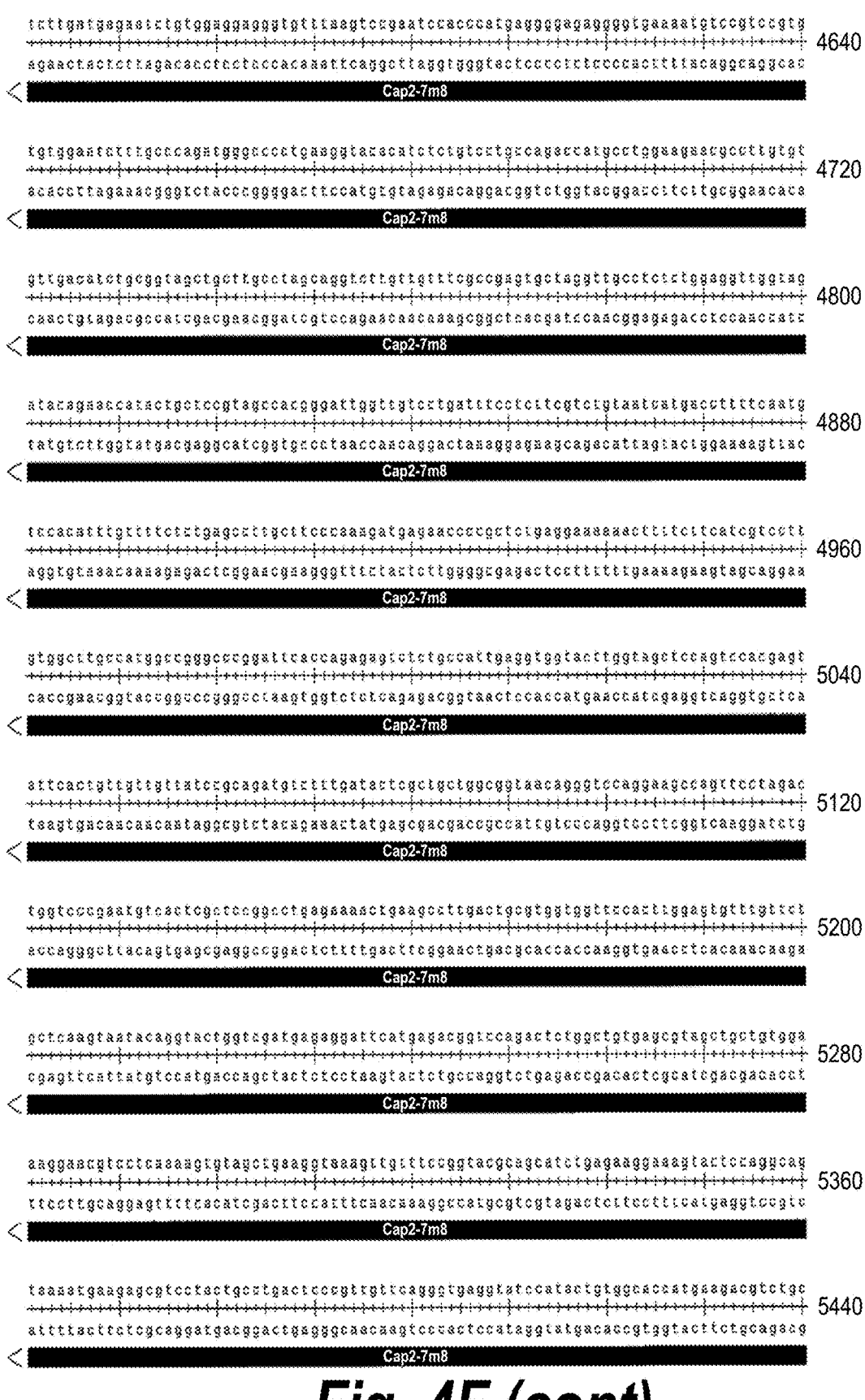
Figure 4G:
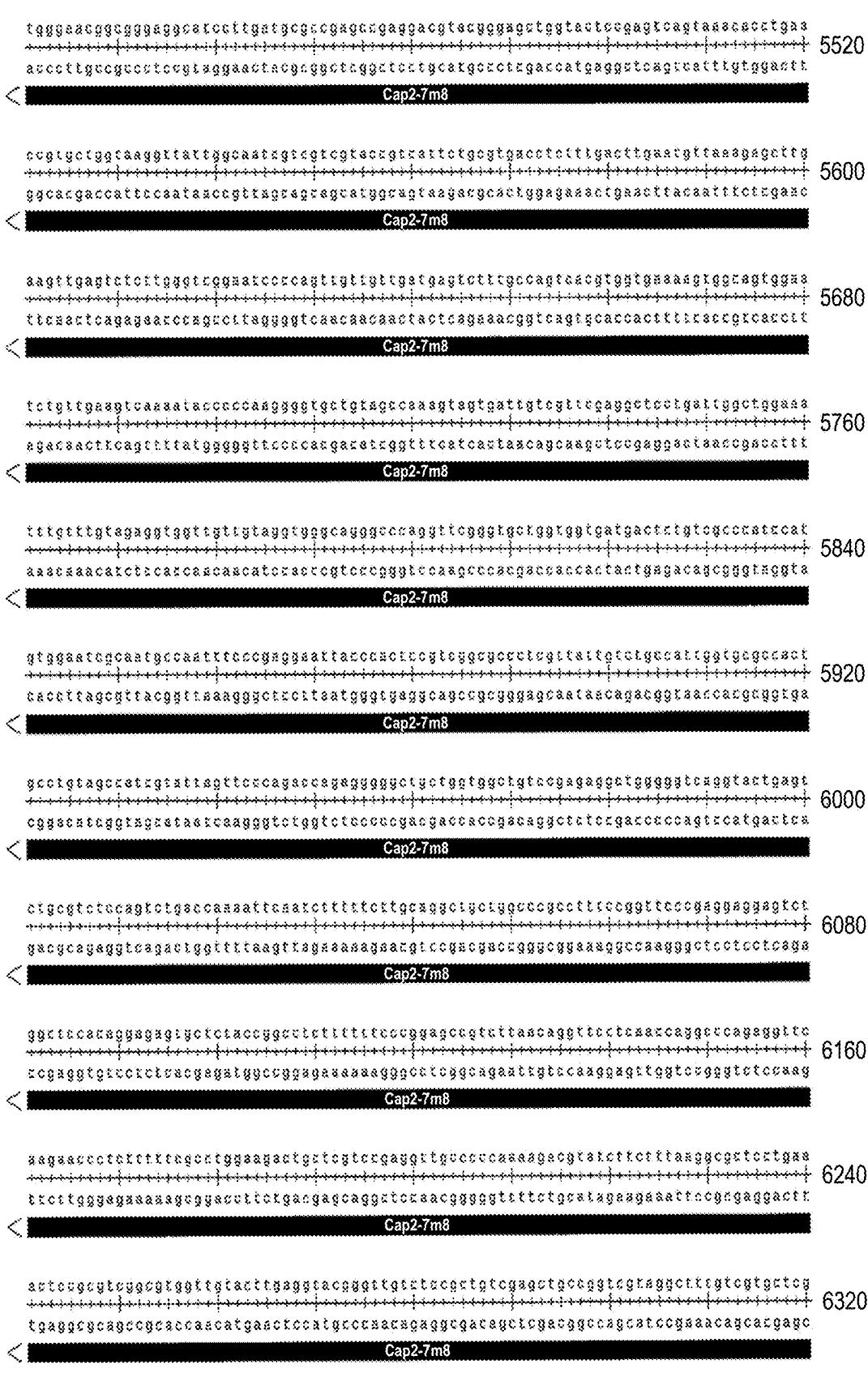
Figure 4H:
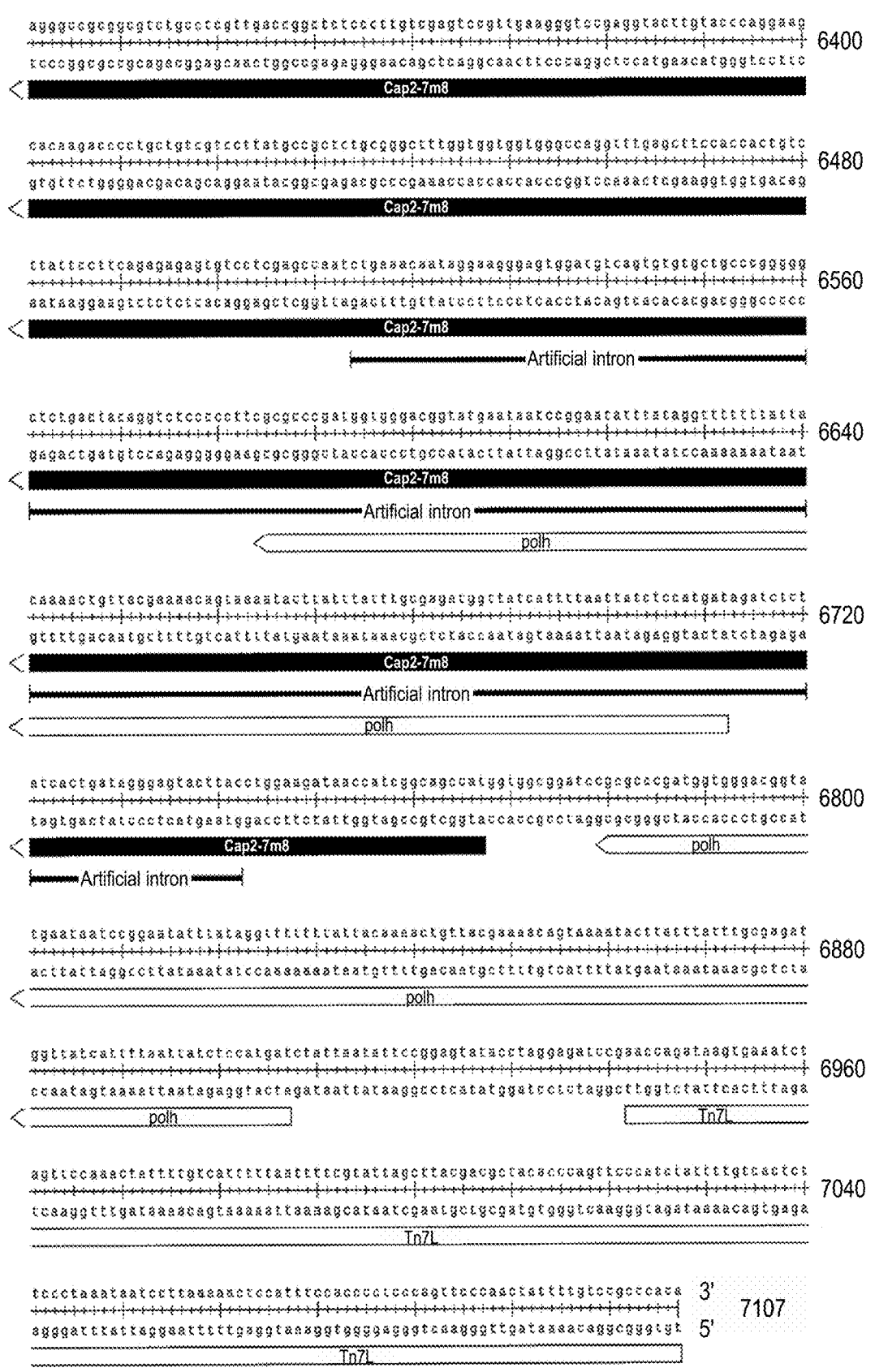

If starting from the bacmid, the CAT selection marker expression cassette flanked by two flippase recognition targets (FRTs) can be PCR-amplified with primers 2846 (5'-TAATAAATGACTGCAGTA-GACGCAAGTTCGTTTCTCATACCACAGGCGTTT CCATATGAATATCCTCCTTA-3') (SEQ ID NO:1) and 6281 (5'-ATAACTAGTCAATAAT-CAATGTCGTGTAGGCTGGAGCTGCTTCGAA-3') (SEQ ID NO:2) and plasmid pKD3 as template. The GFP (or other selection marker) expression cassette can be PCR-amplified with primers 5701 (5'-GACATTGATTAT-TGACTAGTTATTAATAGT-3') (SEQ ID NO:3) and 6282 (5'-GAACAAAATTTTGTTTTAT-TTGTTTGTGTACGGCGTTGTAAACAGCGCGGT TAGATCCAGACATGATAAGAT-3') (SEQ ID NO:4) and plasmid V376 as template. The two PCR fragments then can be joined together to form a larger PCR fragment with primers 6298 (5'-TAATAAATGACTGCAGTAGACGCAA- 3') (SEQ ID NO:5) and 6299 (5'-GAACAAAATTTTGTTT-TATTTGTTTGTGTA-3') (SEQ ID NO:6) and the two PCR fragments as templates. This large PCR fragment can be recombined into the v-cath region between nucleotides 107,034 and 107,904 to disrupt the v-cath gene via the lambda red system (Datsenko et al. (2000) *Proc. Nat.l Acad. Sci. USA* 97(12): 6640-6645; and Thomason (2014) *Curr. Protoc. Mol. Biol.* 106: 1 16 11-39). The junction sequence between CAT expression and GFP expression cassettes and remaining v-cath is shown in FIGS. 2A-2C.

The Δv-cath DNA backbone without a selection marker gene cassette can be created from a bacmid, for example bMON14272, or synthesized de novo. If starting from the bacmid, the CAT selection marker expression cassette flanked by two flippase recognition targets (FRTs) can be PCR-amplified with primers 2845 (5'-GAACAAAAT-TTTGTTTTAT-TTGTTTGTGTACGGCGTTGTAAACAGCG CGGTT GTGTAGGCTGGAGCTGCT-3') (SEQ ID NO:7) and 2846 (5'-TAATAAATGACTGCAGTA-GACGCAAGTTCGTTTCTCATACCACAG GCGTT TCCATATGAATATCCTCCTTA-3') (SEQ ID NO:1) and plasmid pKD3 as template. This PCR fragment containing the CAT expression cassette flanked by two FRTs can be recombined into the v-cath region between nucleotides 107,034 and 107,904 to disrupt the v-cath gene via the lambda red system (Datsenko et al. (2000) *Proc. Nat.l Acad. Sci. USA* 97(12): 6640-6645; Thomason (2014) *Curr. Protoc. Mol. Biol.* 106: 1 16 11-39). After selection of the bacmid DNA and confirmation of the cathepsin deletion, the CAT expression cassette can be removed with the FLP-FRT recombination technology, leaving only one FRT site in the bacmid as shown in FIG. 13.

Δv-cath rBV Genome

The rBV genome according to the disclosure is capable of replicating in an *E. coli* cell and in an insect cell It comprises a Δv-cath DNA backbone as described above, and a foreign protein expression cassette integrated in the Δv-cath rBV genome. The foreign protein expression cassette includes a gene or genes encoding foreign proteins of interest to be expressed in an insect cells, as well as a gene or genes encoding other proteins of interest to be expressed in mammalian cells. Useful genes encoding foreign proteins of interest for expression in insect cells include, but are not limited to, viral proteins and/or mammalian proteins.

Useful viral proteins to be expressed can form the structural part or capsid of a vector carrying a mammalian gene of interest and which is deliverable to mammalian cells. For example, the foreign protein expression cassette can include genes encoding AAV viral proteins, e.g., Rep and capsid (Cap) proteins (FIG. 5B). Proteins of other viruses useful in gene therapy methods include, but are not limited to, hexon, penton complex, fiber proteins from adenovirus, matrix, capsid, nucleocapsid proteins from retrovirus such as, but not limited to, lentivirus, VP5, VP23, VP19C, VP26, and capsid-vertex-specific component proteins from Herpes simplex virus (HSV), and the major VP1 protein from SV40.

Useful mammalian proteins that can be directly expressed in insect cells include, but are not limited to, human immunoglobulins, human serum albumins, erythropoietin-alpha, and Factor VIII.

The foreign protein cassette also includes control elements including, but not limited to, an insect cell promoter which enables expression of operably linked genes in an insect cell. Useful insect promoters include, but are not limited to, a polyhedron (polh), p10, OpIE2 or p6.9 insect promoter. If the cassette includes mammalian genes to be expressed in a mammalian cells, promoter enabling expression of these mammalian genes in the mammalian cell will be operably linked to that gene. Useful mammalian promoters include, but are not limited to, CMV, SV40, pGK, EF1a, synapsin, chicken beta actin, and CamKII promoter, etc.

The foreign protein expression cassette may also link to one or more additional selection marker gene. This marker gene is different than the selection marker gene in the selection marker expression cassette (if it is present in the rBV backbone) as described above which is expressed upon infection of the insect cell.

The foreign protein expression cassette is flanked by transposable DNA elements enabling it to be integrated into the rBV DNA backbone at specific nucleic acid sites or locations. Useful transposable DNA element include, but are not limited to, Tn7L and Tn7R (FIG. 1A). Alternatively, the foreign protein expression cassette can be flanked by sequences homologous to the rBV genome, for example the sequences between 3,272 and 4,518, and between 5,270 and 6,689, which enable it to be integrated into the rBV DNA backbone via homologous recombination mechanism as shown in FIG. 1B.

Figure 6:
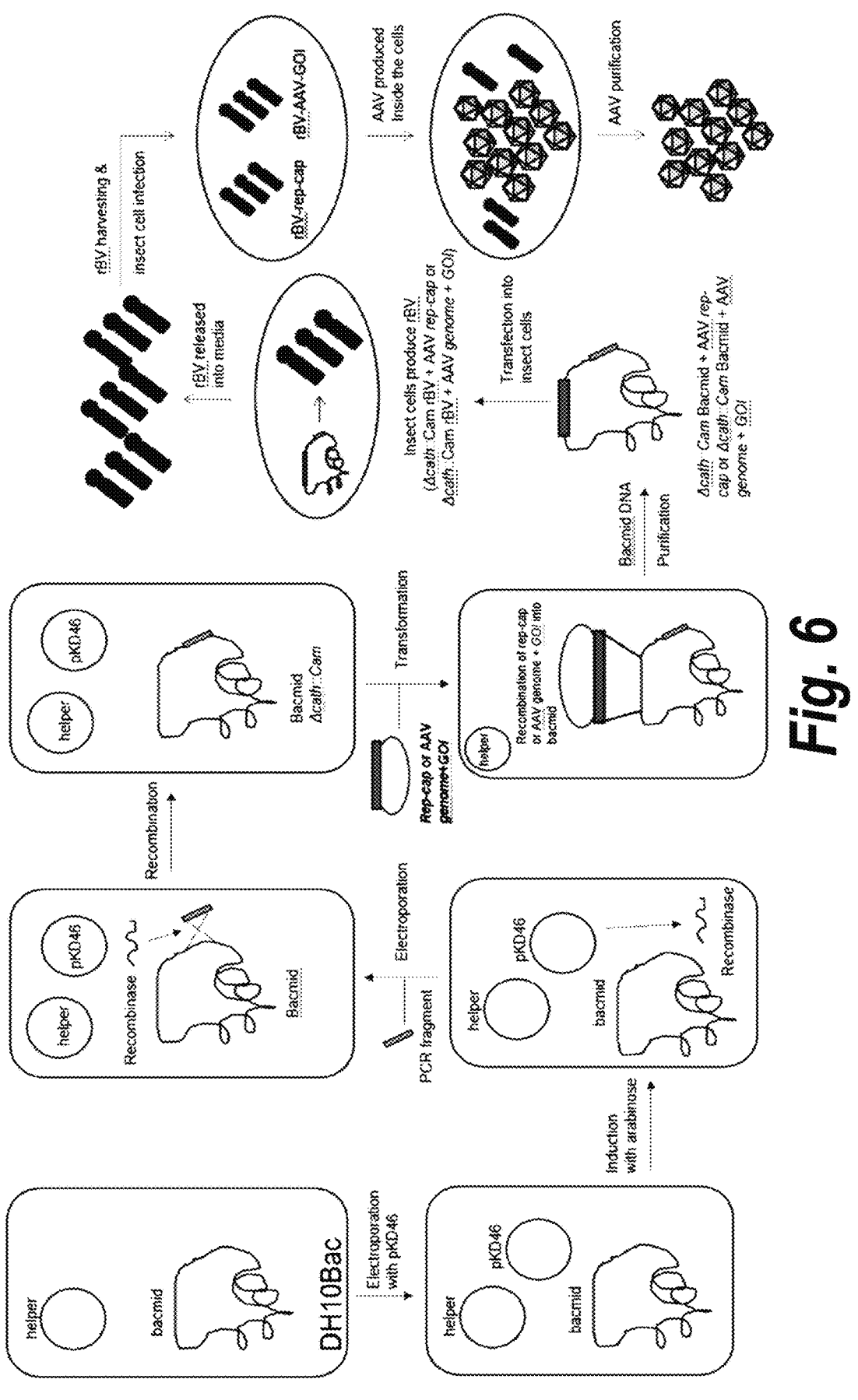
FIG. 6 is a flow chart showing the process of deleting v-cath and production of the AAV vectors in insect cells using the rBV system according to the disclosure.
Figure 7A:
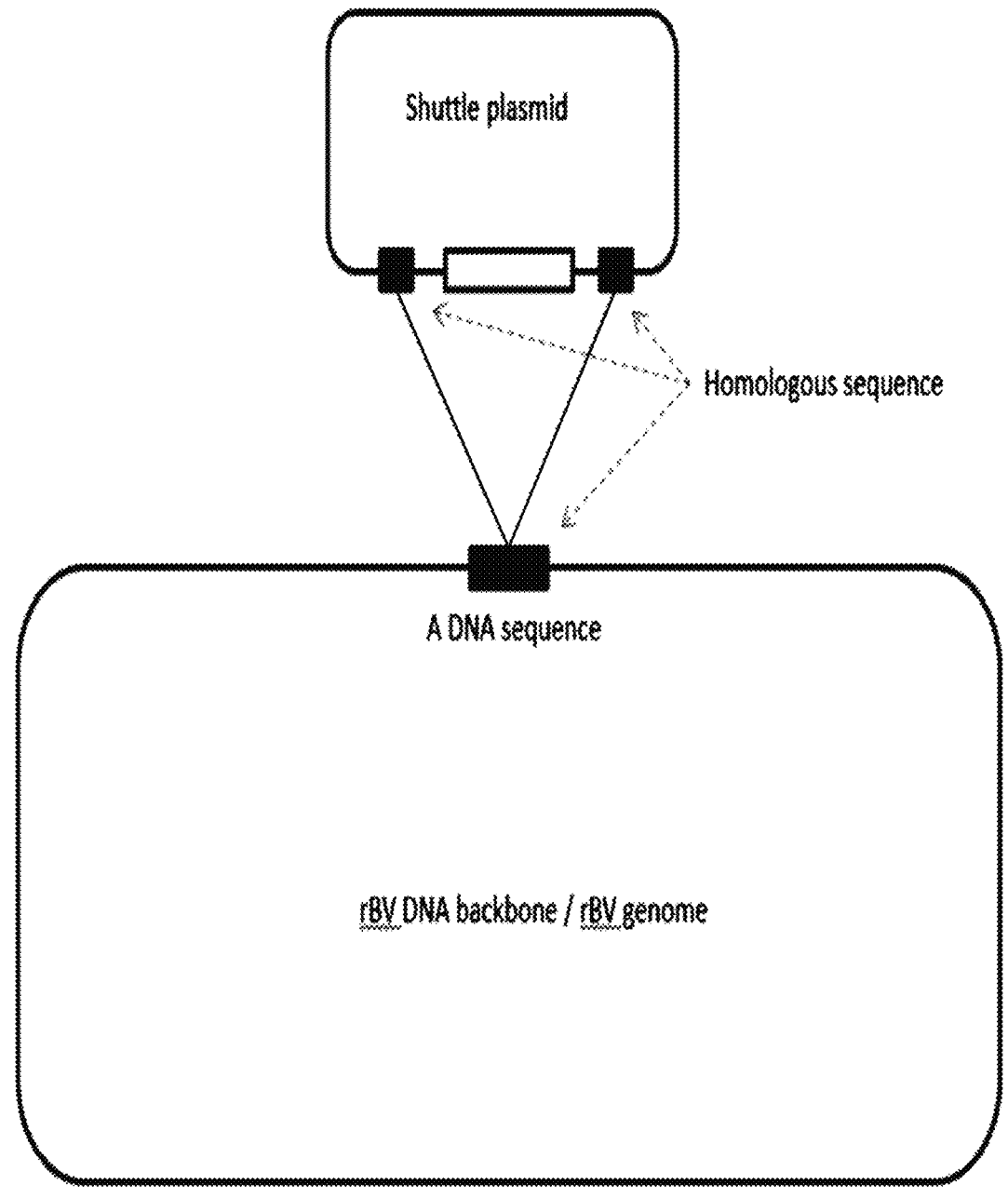
FIG. 7A is a diagrammatic representation of integrating a foreign expression cassette into the Δv-cath rBV DNA backbone by homologous recombination.
Figure 7B:
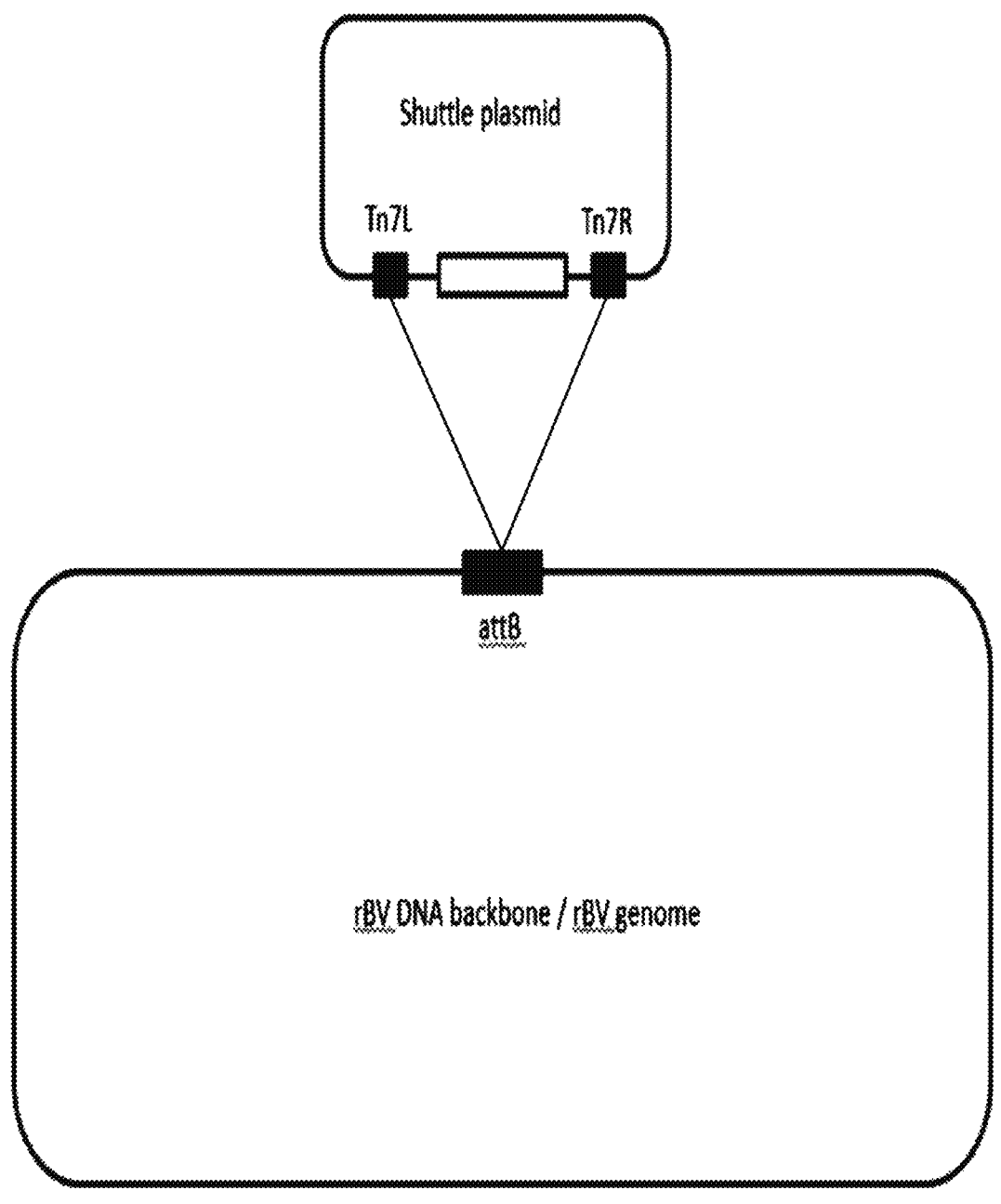
FIG. 7B is a diagrammatic representation of integrating a foreign expression cassette into the Δv-cath rBV DNA backbone by transposase.

As shown in FIG. 6, integration of the cassette into the baculovirus backbone can be accomplished by transformation of a donor plasmid (e.g., pFastBac-1). The donor plasmid comprises one or more foreign protein expression cassettes, operably linked to appropriate promoters, enhancer and polyadenylation signal as well as a bacterial selection marker gene and promoter. The transposase expressed by the helper plasmid catalyzes the transposition of Tn7L and Tn7R which flank the foreign protein expression cassettes at specific sites within the mini-att Tn7 region of the bacmid, thus incorporating the foreign expression cassettes into the bacmid. Alternatively, the foreign protein expression cassettes can be inserted into the appropriate region of the recombinant baculovirus backbone by means of other methods such as but not limited to homologous recombination using a donor plasmid that contains homologous sequences of the rBV, which flank the foreign protein expression cassettes as illustrated in FIG. 1B.

Figure 5A:
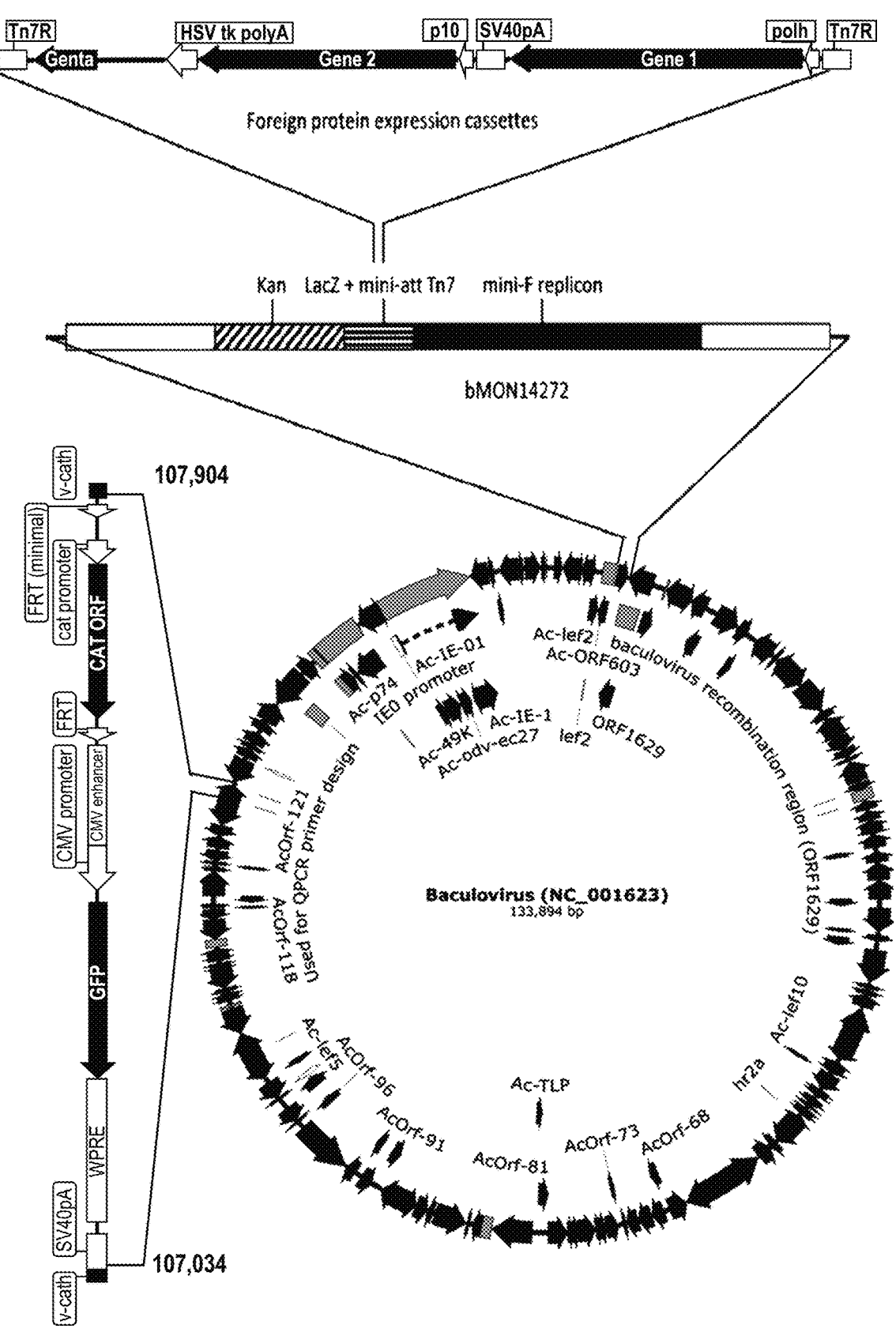
FIGS. 5A-5D are a series of diagrammatic representations of an exemplary Δv-cath rBV genomes including a selection marker CAT expression cassette and GFP expression cassette which have been inserted at the position of the v-cath deletion, and further including generic foreign protein expression cassettes carrying a gentamycin selection marker gene (Genta), and foreign Gene 1 and Gene 2 (FIG. 5A); carrying Genta, AAV Rep, and Cap AAV genes (FIG. 5B); carrying Genta, an AAV genome consisting of a luciferase gene (FIG. 5C); and carrying Genta, and mammalian proteins (human antibody heavy chain and human antibody light chain) genes (FIG. 5D), each of which have been inserted into bMON14272 bacmid.
Figure 5B:
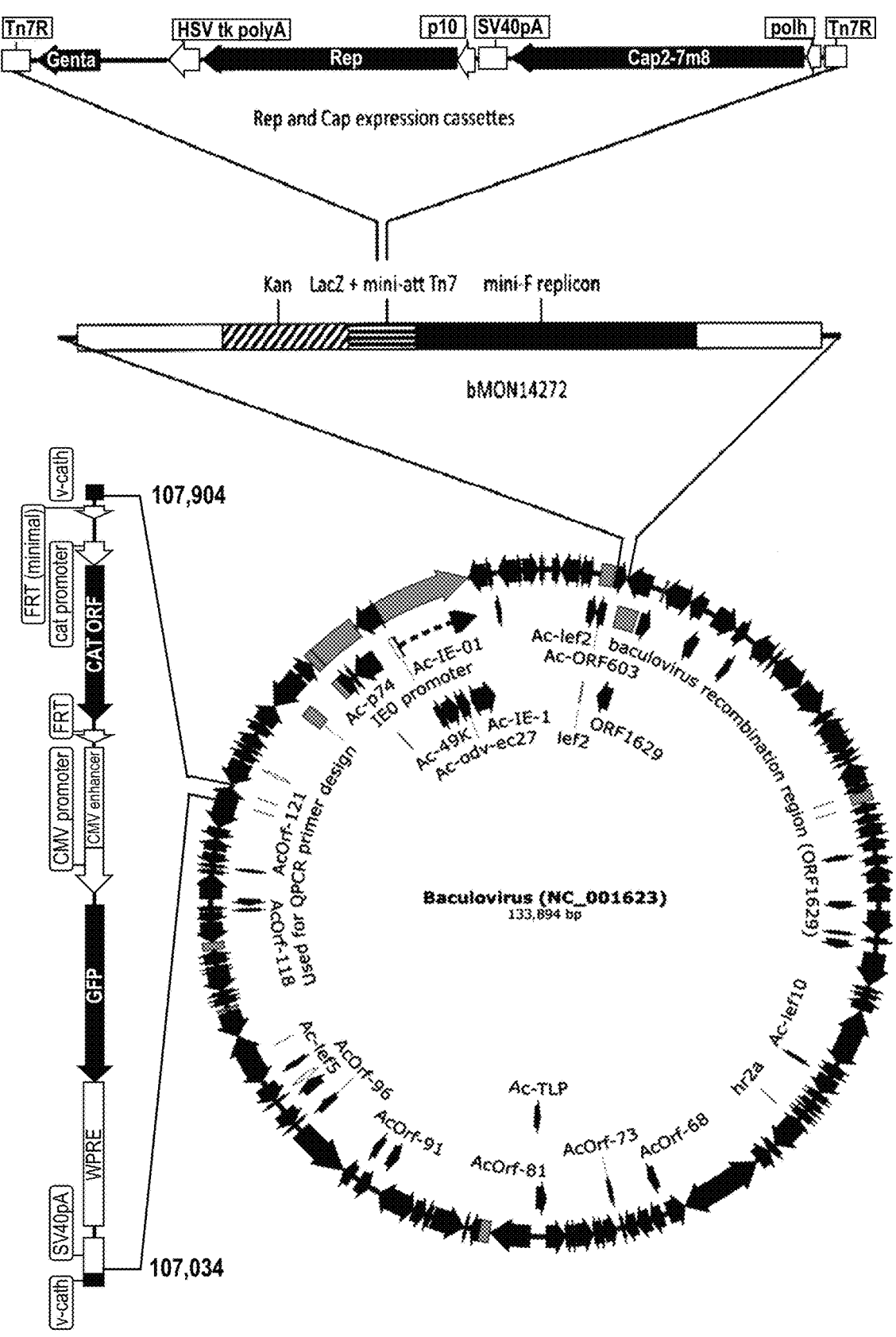
Figure 5C:
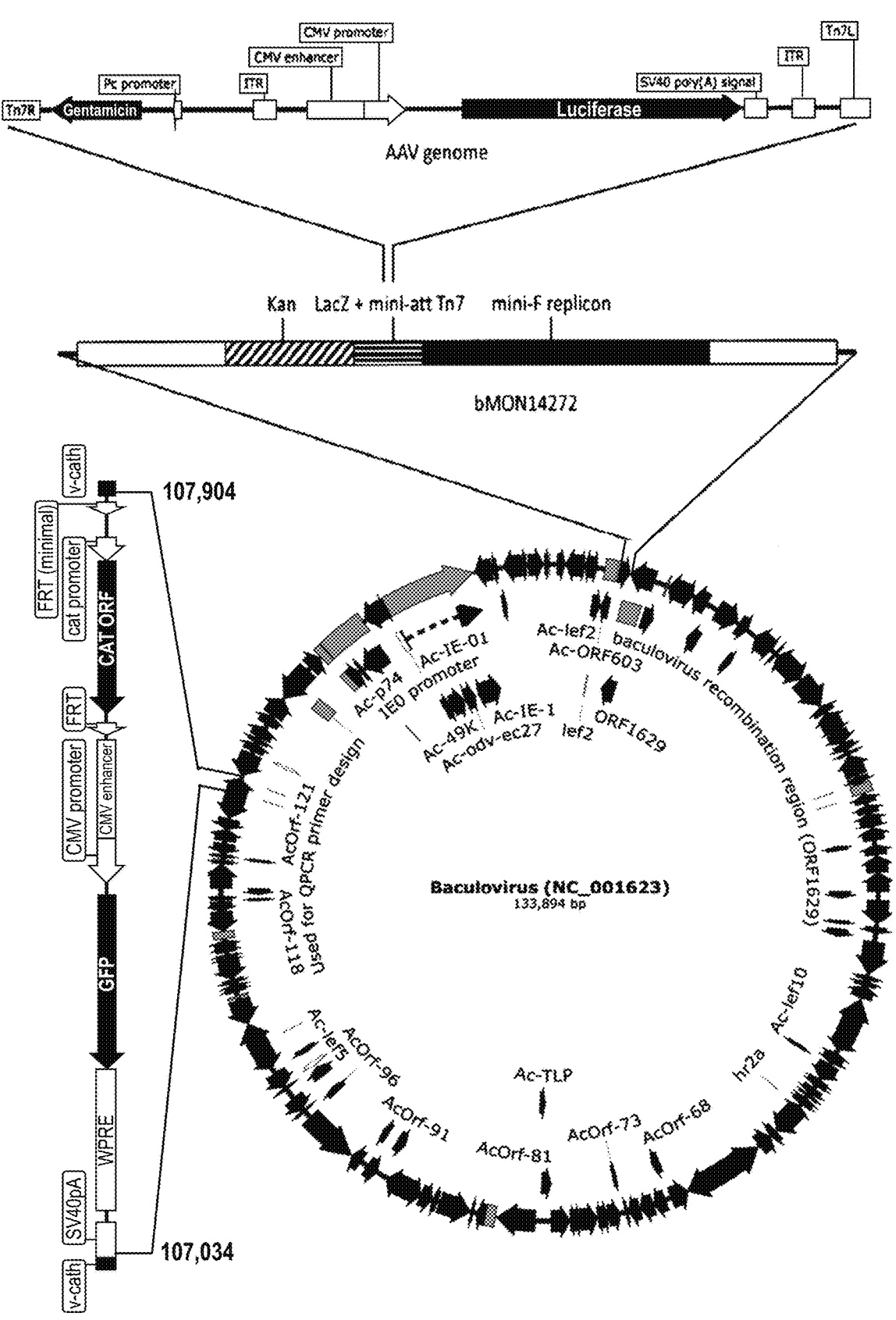
Figure 5D:
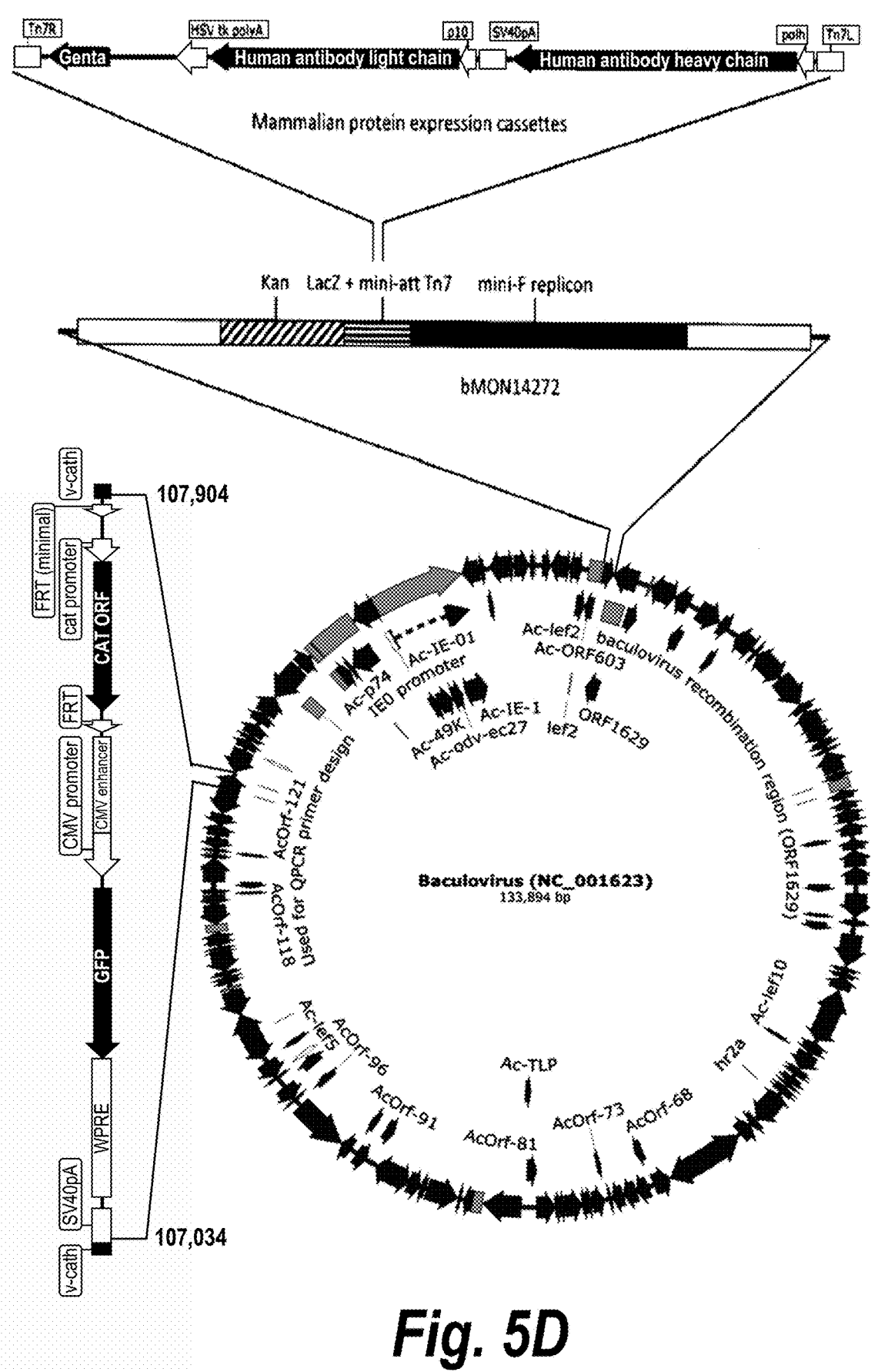
Figure 16A:
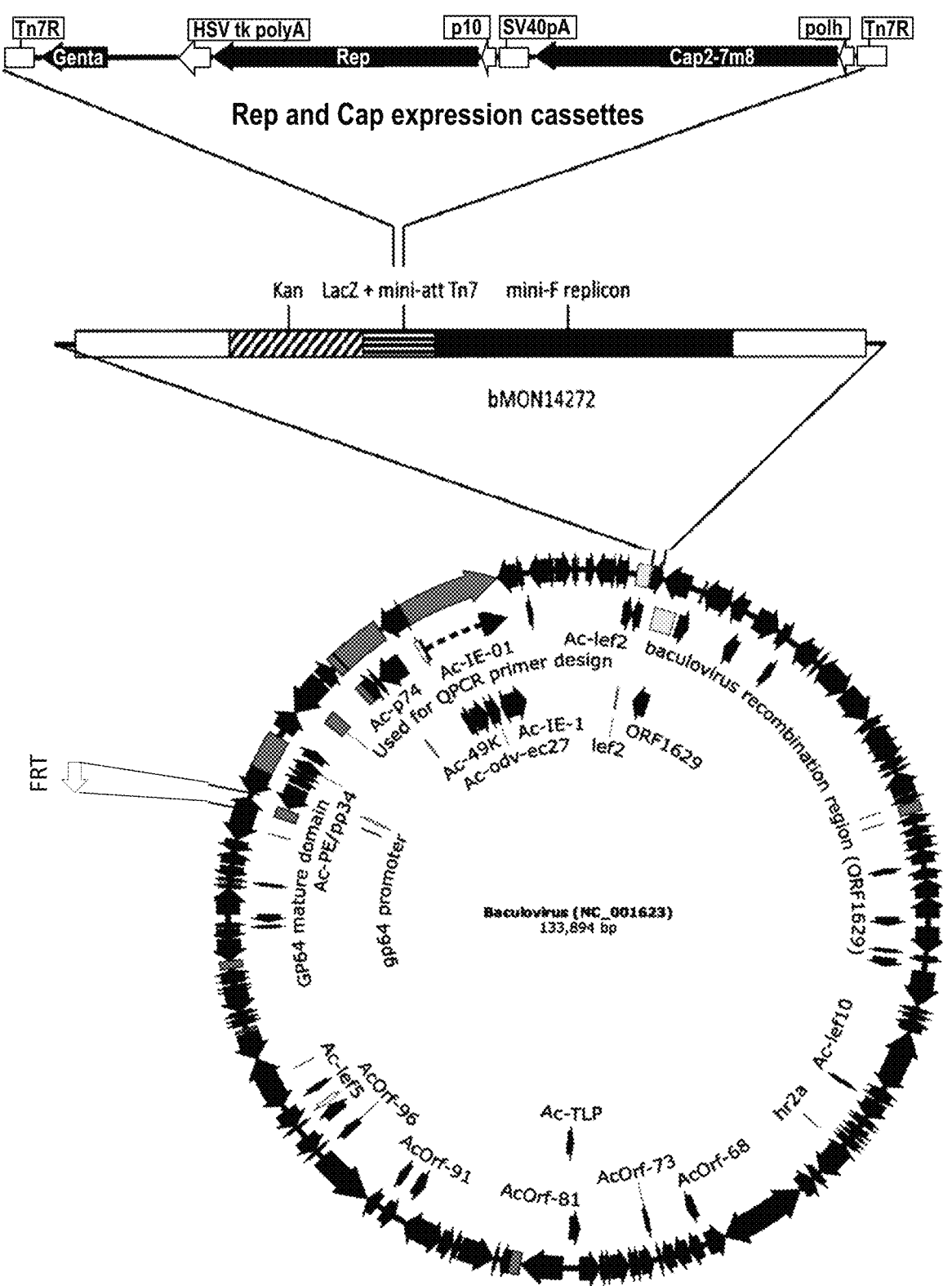
FIGS. 16A-16D are a series of diagrammatic representations of an exemplary Δv-cath rBV genomes after removal of the CAT expression cassette and only one FRT site left at the position of the v-cath deletion, and further including generic foreign protein expression cassettes carrying a gentamycin selection marker gene (Genta), and foreign Gene 1 and Gene 2 (FIG. 16A); carrying Genta, AAV Rep, and Cap AAV genes (FIG. 16B); carrying Genta, an AAV genome consisting of a luciferase gene (FIG. 16C); and carrying Genta, and mammalian proteins (human antibody heavy chain and human antibody light chain) genes (FIG. 16D), each of which have been inserted into bMON14272 bacmid.
Figure 16B:
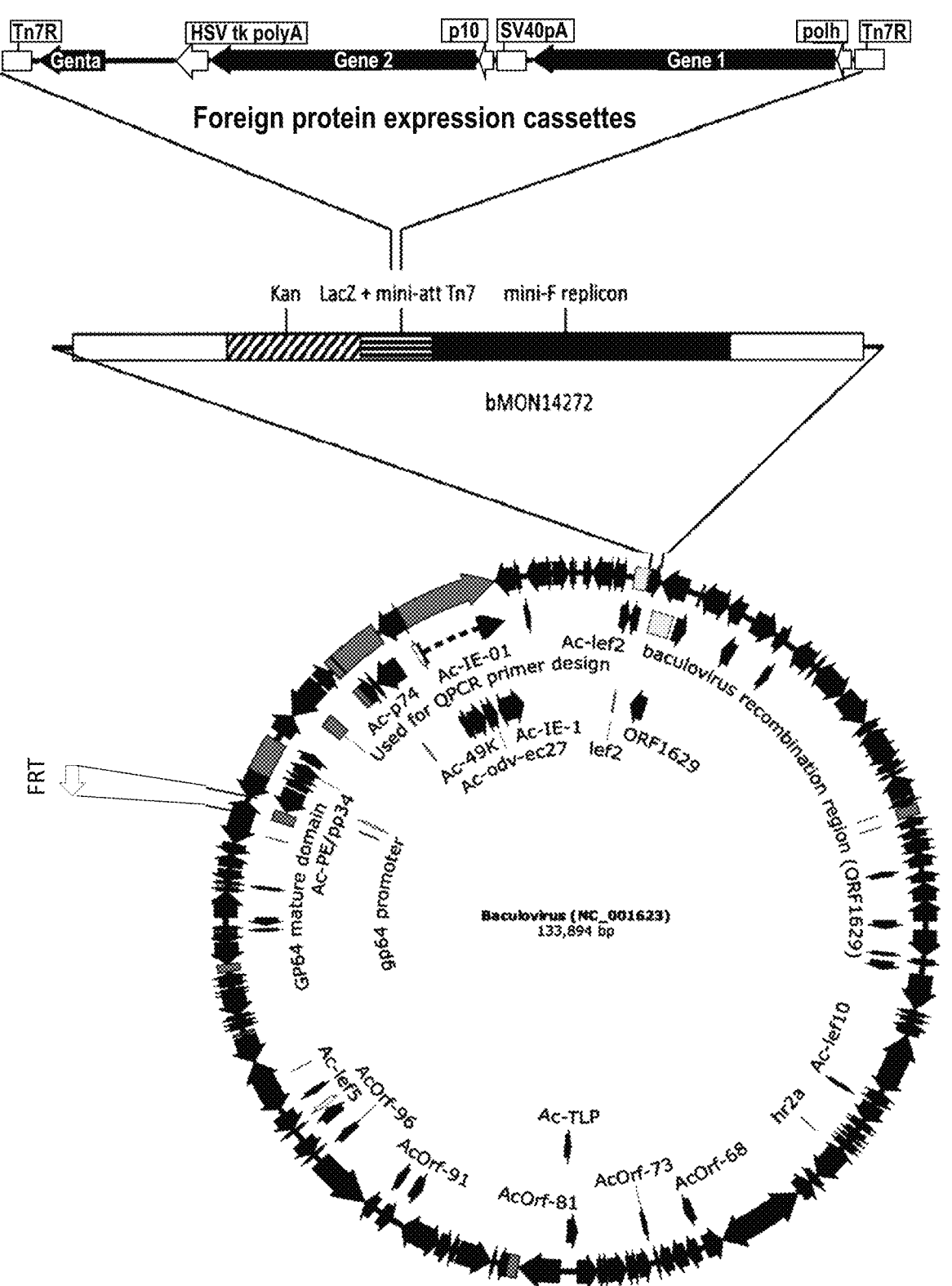
Figure 16C:
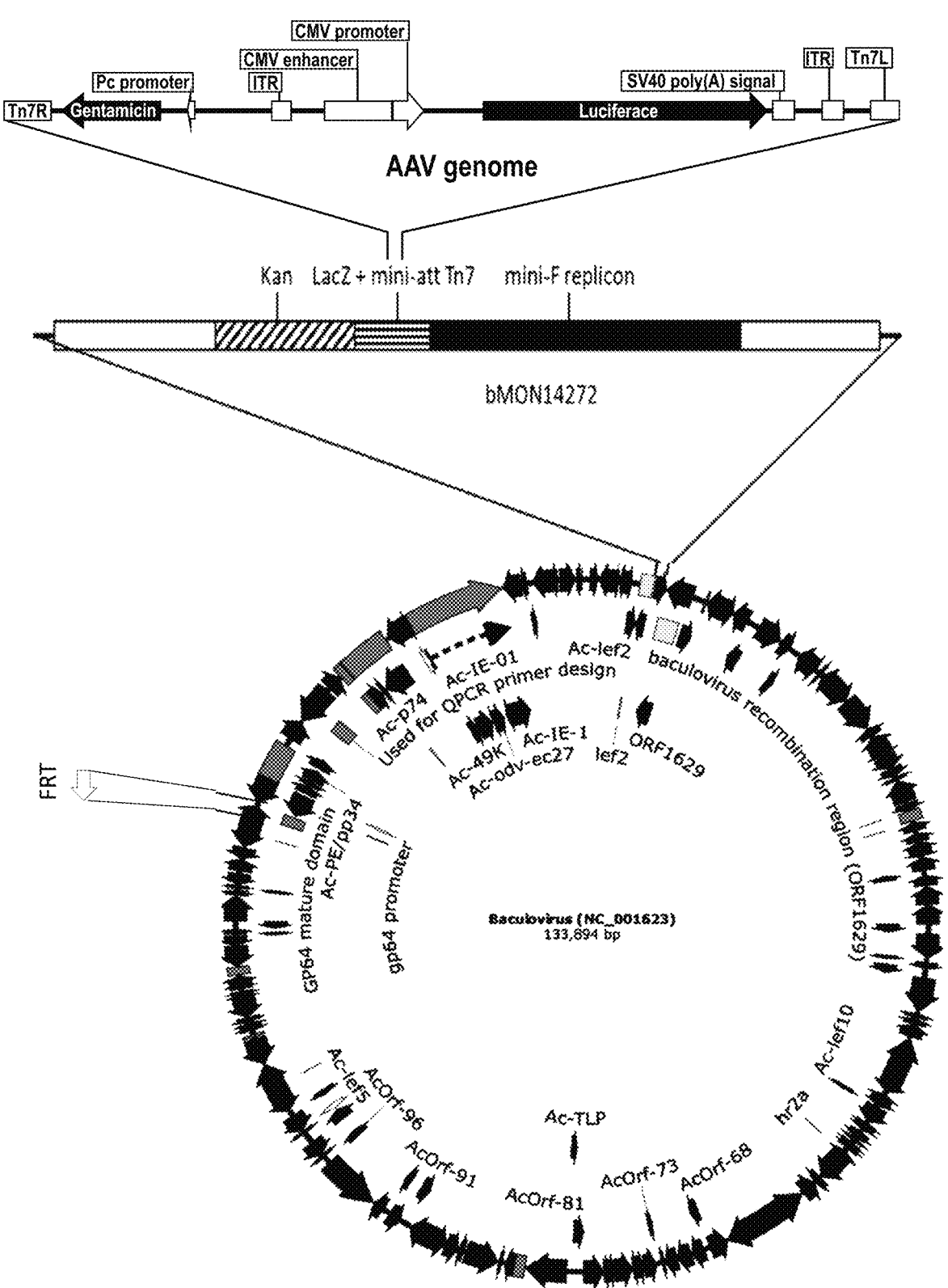
Figure 16D:
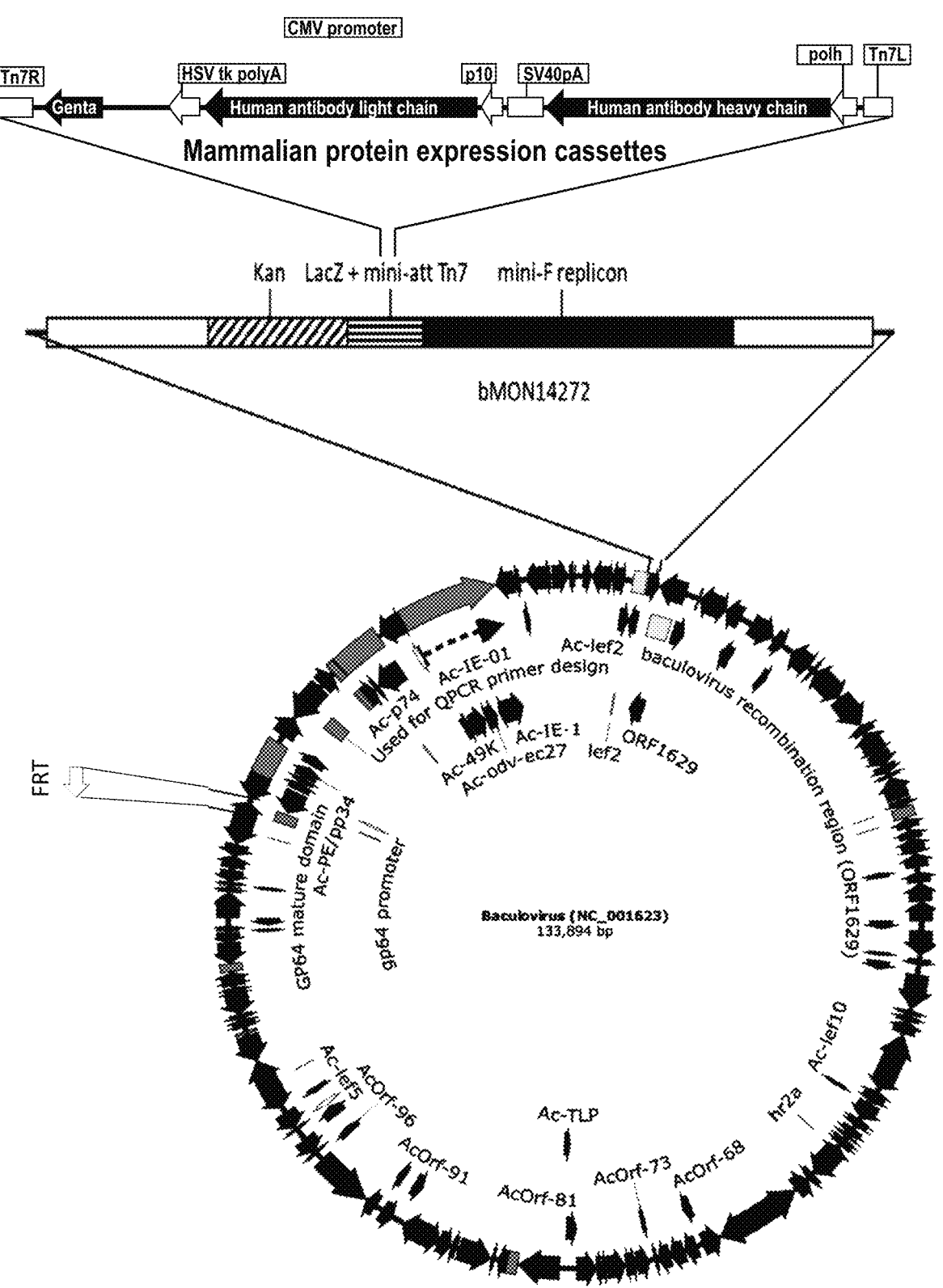

A diagram of an exemplary generic rBV genome with a v-cath deletion/CAT and GFP selection marker expression cassette insertion and the additional insertion of two foreign protein expression cassettes are shown in FIG. 5A. FIG. 5B shows the rBV genome with the Δv-cath deletion and insertion of AAV Rep and Cap foreign protein expression cassettes. FIG. 5C shows the rBV genome with the Δv-cath deletion/AAV, gentamycin, and luciferase foreign protein expression cassettes insertion. FIG. 5D shows the rBV genome with the Δv-cath deletion and insertion of a gentamycin/mammalian protein expression cassettes insertion encoding human antibody light and heavy chains. Alternatively, the rBV genome with a v-cath deletion/without CAT and GFP selection marker expression cassette insertion and the additional insertion of two foreign protein cassettes are shown in FIG. 16A. FIG. 16B shows the rBV genome with the Δv-cath deletion and insertion of AAV Rep and Cap foreign protein expression cassettes. FIG. 16C shows the rBV genome with the Δv-cath deletion/AAV, gentamycin, and luciferase foreign protein expression cassettes insertion. FIG. 16D shows the rBV genome with the Δv-cath deletion and insertion of a gentamycin/mammalian protein expression cassettes insertion encoding human antibody light and heavy chains.

Cell Culture

Cells that can be infected by the rBV vector or transformed by bacmid include insect cells or prokaryotic cells such as *E. coli*. Useful *E. coli* cells include, but are not limited to, Top10, DH5a, DH10B, TGI, BW23473, BW23474, MW003, Mwoo5, and BL21. Useful insect cells that can be infected by the rBV vector include, but are not limited to, Sf9, Sf21, Express Sf+, and S2 cells from the Fall Army worm (*Spodoptera frugiperda*), or BTI-TN-5B1-4 (High Five cells) from the cabbage looper *Trichoplusia ni* (*Lepidoptera*), *D. melanogaster*, and other cell lines. These cells are commercially available from a number of sources (e.g., ThermoFisher Scientific, ATCC, and Expression Systems). Insect cells are cultured in a medium conducive for maintenance and growth, such as, but not limited to Gibco insect media: ExpiSf CD Medium, Sf-900 III SFM, Express Five SFM, or SF-900 II SEM (ThermoFisher Scientific), ESF921 and ESFAF (Expression Systems).

rBV Infection rBV infects insect cells upon contact under conditions conducive from the virus to enter the cell, e.g., by culturing the contacted cells at about 28° C. for about three days in a medium conducive for expression of the foreign proteins, e.g., in Gibco insect media (ExpiSf CD Medium, Sf-900 III SFM, Express Five SFM, or SF-900 II SEM (ThermoFisher Scientific), ESF921 or ESF AF media (Expression Systems). Successful infection can be monitored e.g., by expression of a visually detectable selection marker protein, or the expression of the gene for which had been incorporated into the rBV genome.

Foreign Protein Expression and Isolation

Foreign proteins including those which are the structural part of viral vectors carrying mammalian genes, or directly expressed from mammalian genes can be obtained from infected insect cells by lysing the cells and isolating the proteins from the lysate. Lysing can be accomplished with physical force (e.g., with a French Press or sonication), detergent-containing lysis buffer, or enzymatic digestion of the cell matrix with, e.g., chitinase that is naturally expressed by the baculovirus genome.

The expressed foreign proteins or produced viral particles can be isolated, for example, by chromatographic or electrophoresis methods or by centrifugation, e.g., on cesium chloride gradients.

These isolated and purified proteins can then be used, e.g., for therapeutic purposes or as research reagents. If the foreign protein is part of a viral vector that carries mammalian genes, the viral vector is isolated and then can be used to infect mammalian cells, e.g., for gene therapy.

Effect of the Δv-cath Deletion on Foreign Protein Expression

Figure 8:
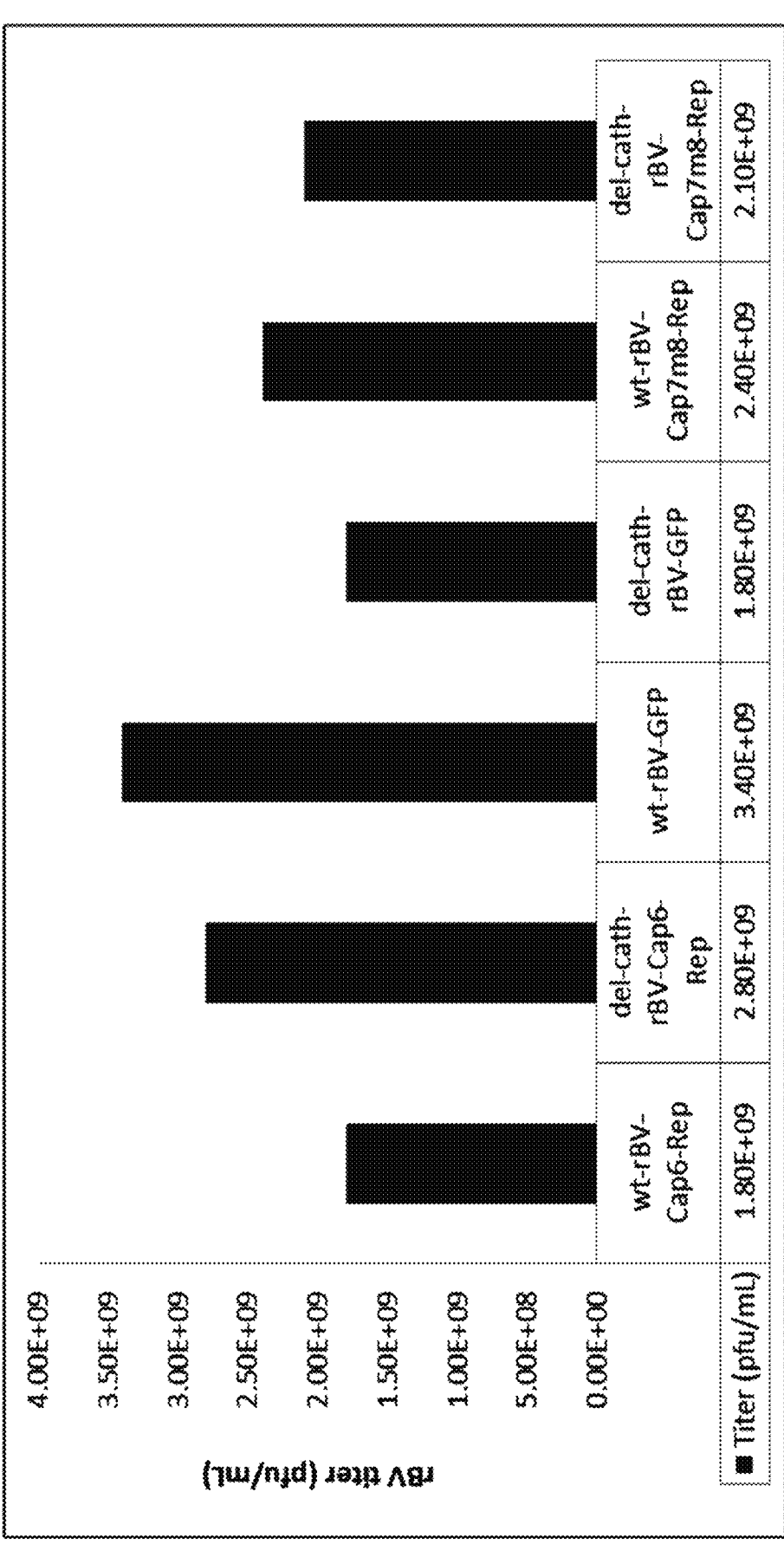
FIG. 8 is a graphic representation of the titer of WT-rBVs and Δv-cath rBV comprising the Cap6-rep expression cassettes, GFP expression cassette, or Cap2-7m8-rep expression cassettes respectively according to the disclosure.

To demonstrate that deletion of the v-cath gene from the baculovirus genome had no effect on baculovirus replication, the replication of wild type rBV was compared with the replication of the Δv-cath-rBV according to the disclosure. Both rBVs carrying the same foreign (AAV capsid and rep or GFP) genes were used to infect insect (Sf9) cells. WT baculovirus and Δv-cath deletion mutant rBV titers were then determined to be similar, demonstrating that v-cath deletion has no negative impact on virus production (FIG. 8).

To demonstrate that the foreign proteins expressed from Δv-cath rBV are not degraded, foreign protein expression in Δv-cath rBV-infected cells was compared with protein expression in WT-rBV-infected cells. The resulting synthesized AAV vectors were then purified from the cell lysates. After heating both types of AAV particles, their capsid proteins were examined by SDS-PAGE.

Figure 9:
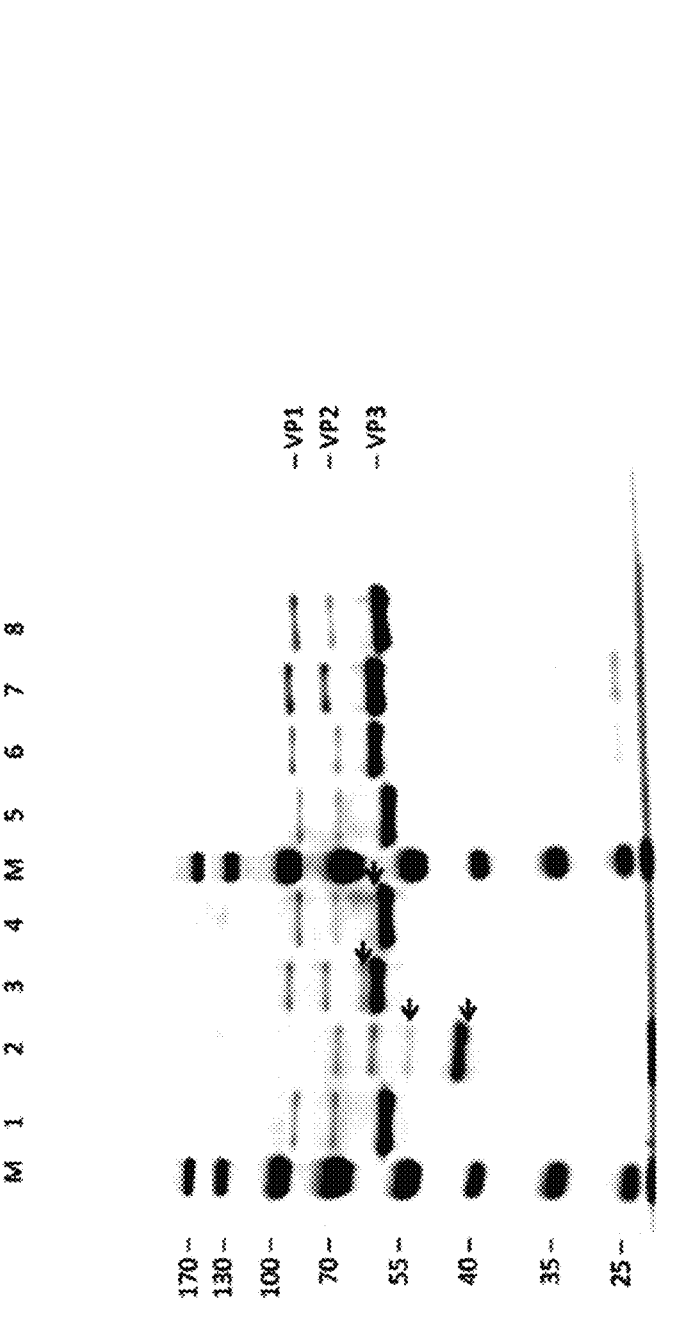
FIG. 9 is a representation of an SDS-PAGE gel stained with Simply Blue showing AAV capsid proteins expressed from different recombinant baculovirus vectors carrying capsid VP1, VP2, and VP3 genes of different AAV serotypes with and without the v-cath gene, wherein M is a protein ladder, lAnes 1 and 5 are AAV9 controls, lanes 2 and 6 are AAV7m8-GFP, lanes 3 and 7 are AAV8-GFP, lanes 4 and 8 are AAV6-GFP, lanes 6-8 are AAV vectors, and arrow indicate degraded.

The results shown in FIG. 9 demonstrate that deletion of the v-cath gene decreased capsid protein degradation. AAV7m8 was severely degraded when produced with WTrBVs, in contrast to the AAV7m8 capsids produced with Δv-cath-rBVs, where no degradation was seen (compare lane 2 with lane 6). There was only minor degradation to the AAV8 (lane 3) and AAV6 (lane 4) capsid proteins.

To demonstrate that Δv-cath rBVs can produce higher AAV yields than WT-rBVs, AAV7m8-luciferase and AAVphpb-luciferase vectors were produced in Sf9 cells infected with Δv-cath rBVs and WT-rBVs, respectively. When preparing cell lysates, the protease inhibitor Leupeptin was added to the lysis buffer for WT-rBV infected lysates to prevent degradation so that AAV production yield could be preserved. No protease inhibitor was added to Δv-cath rBV-infected lysates. After purification, the AAV vectors were quantified. The results are shown in Table 1.

TABLE 1

Comparison of AAV Production Yields Between
Δv-cath rBVs and WT-rBVs

| Lot no. | Type of rBV | Type of AAV | AAV production yield (vg/L) | Folds of difference |
|---------|-------------|-------------|------------------------------|---------------------|
| 19-137 | Δv-cath-rBV | AAV7m8-Luciferase | 1.66e+14 | 2.86 |
| 19-156 | WT-rBV | AAV7m8-Luciferase | 6.11e+13 | 1.05 |
| 19-145 | Δv-cath rBV | AAVphp.b-Luciferase | 2.30e+14 | 3.97 |
| 19-175 | WT-rBV | AAVphp.b-Luciferase | 5.80e+13 | 1 |

These results show that foreign protein expression in Δv-cath rBV-transduced cells was 3× to 4× greater than the same foreign protein expression in WT-rBV-transduced cells.

Figures 10A, 10B, 10C, 10D, 10E, 10F:
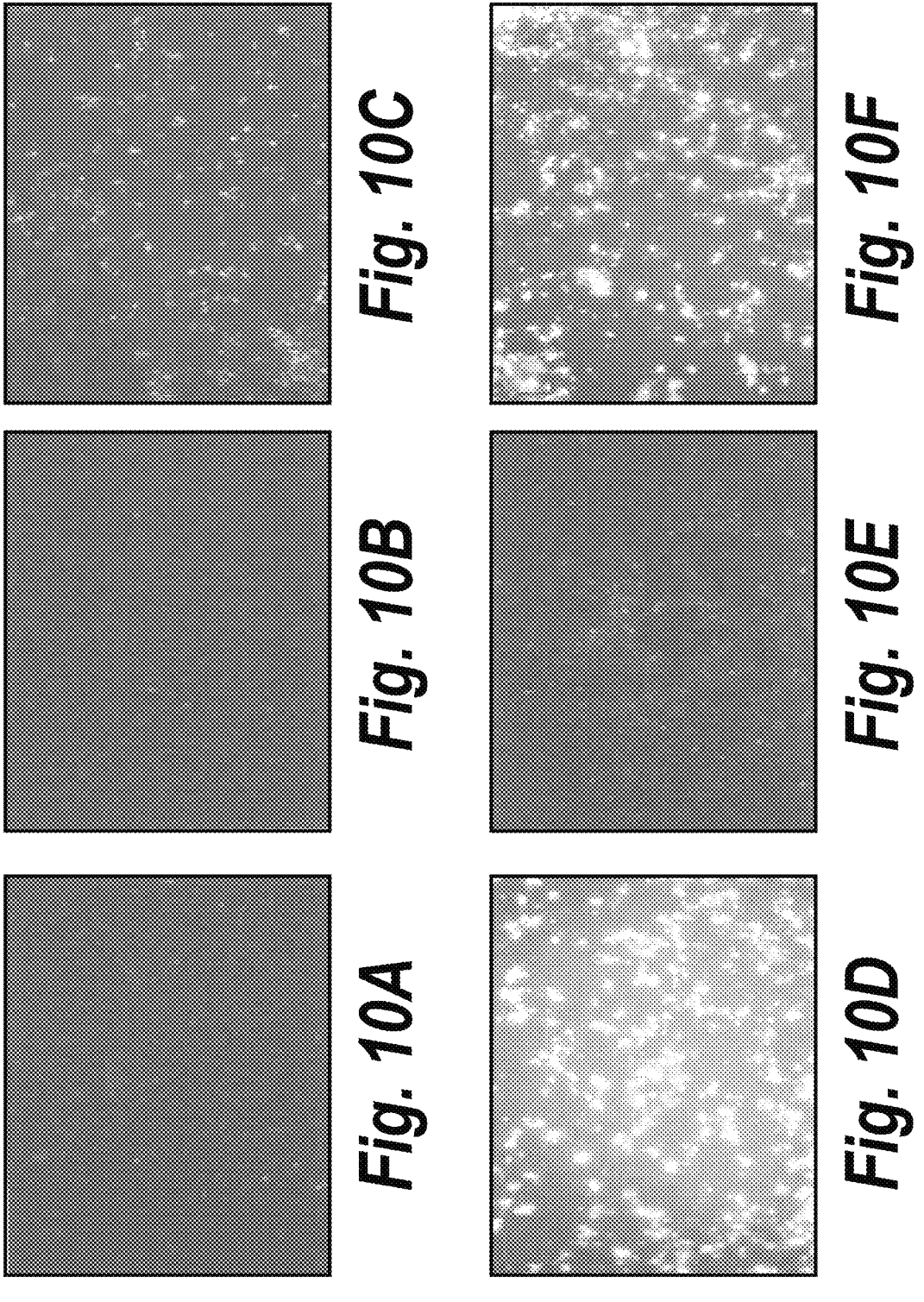
FIGS. 10A-10F is series of representations of fluorograms of HEK-293 (mammalian) cells that had been transduced with the same amount of AAV vectors comprising GFP expression cassette produced by rBVs with and without the v-cath gene, where

It was also determined that AAV vectors produced with Δv-cath rBVs relative to those produced with WT-rBVs had greater infectivity in mammalian cells. Testing was done in HEK-293 cells using AAV vectors isolated from insect cells infected with either the WT-rBVs or the deletion mutants. GFP expression was recorded. The results shown in FIGS. 10A-10F demonstrate that AAV vectors produced with WT-rBVs (FIGS. 10A-10C) have lower infectivity than those produced with Δv-cath rBVs (FIGS. 10D-10F).

Reference will now be made to specific examples illustrating the disclosure. It is to be understood that the examples are provided to illustrate exemplary embodiments and that no limitation to the scope of the disclosure is intended thereby.

EXAMPLES

Example 1

Insect Cell Culture

Sf9 cells (Expression Systems, Davis, Calif.) were cultured in Corning storage bottles at 28° C. in ESF921 or ESF AF media (Expression Systems) supplemented with 100 units/mL penicillin and 100 μg/mL streptomycin (HyClone, Logan, Utah). The cells were split 1:4 once the cell density reaches about $8×10^6$ cells/mL for maintenance.

Example 2

Deletion of v-cath Gene from Baculovirus Backbone

The protocol of lambda red system (Thomason (2014) *Curr. Protoc. Mol. Biol.* 106: 16 11-394) was used to perform the deletion. Briefly, a 1.1 kB fragment containing the chloramphenicol acetyltransferase (CAT) expression cassette flanked by two FRTs (FIGS. 2A-2C, bases 51-1066) was PCR-amplified with primers 2846 (SEQ ID NO:1) and 6281 (SEQ ID NO:2) and plasmid pKD3 (The ODIN, Oakland, Calif.) as a template. A 2.2 Kb fragment containing the GFP expression cassette (FIGS. 2A-2C, bases 1067-3223) was PCR-amplified with primers 5701 (SEQ ID NO:3) and 6282 (SEQ ID NO:4) and V376 as template. After gel purification, both PCR fragments were joined to form a 3275-bp PCR fragment with primers 6298 (SEQ ID NO:5) and 6299 (SEQ ID NO:6). The PCR fragment was digested with restriction enzyme DpnI (New England Biolabs, Ipswich, Mass.) to remove contaminating plasmid template. Then plasmid pKD46 containing the red recombinase (The ODIN) was electroporated into the DH10Bac-competent cells (ThermoFisher Scientific) to obtain DH10Bac colonies containing the red recombinase. One of the colonies was induced with 0.035% L-(+)-arabinose (Sigma-Aldrich, St. Louis, Mo.) to express the recombinase. After induction for 45 min at 37° C. with gentle shaking, the DH10Bac-competent cells containing the red recombinase were electroporated with the 3275-bp CAT-GFP PCR fragment and incubated for another 3 hours for recombination to occur. The electroporated DH10Bac-red cells were cultured overnight.

Colonies containing the bacmid with v-cath deletion were verified by DNA sequencing analysis and designated as DH10Bac-Δv-cath. One of these colonies was chosen to prepare competent cells which were used for generation of recombinant baculovirus without v-cath.

Example 3

Recombinant Baculovirus Generation

Recombinant baculovirus containing the genes of interest were generated using recombinant baculovirus shuttle vectors (bacmids) that can recombine with a donor plasmid according to manufacturer's protocol (Invitrogen, Carlsbad, Calif.). Briefly, the donor plasmids were diluted in sterile TE buffer (10 mM Tris-HCL, 1 mM EDTA, pH 8.0) to a concentration of 2 ng/μL, and 2 μL of the diluted plasmid DNA was used to transform 20 μL of DH10Bac-wild type (wt)- or DH10Bac-Δv-cath-competent cells. After 2 days of incubation on the LB-agar plates at 37° C., white colonies were picked and miniprep bacmid DNAs prepared according to manufacturer's protocol (Invitrogen).

The miniprep bacmid DNAs were then used to transfect Sf9 cells to generate recombinant baculoviruses according to manufacturer's protocol (Invitrogen) with modifications. Briefly, 5 μg miniprep bacmid DNA and 5 μl GenJet reagent (SignaGene Labs, Rockville, Md.) were each diluted in 100 μl of ESF AF media (Expression Systems) in sterile 1.5 mL microfuge tubes. The diluted GenJet reagent was transferred to the diluted bacmid DNA tube and mix by gentle pipette up and down for 3 times. After incubation at room temperature for about 30 min, 0.8 mL ESF AF media was added to the GenJet-bacmid mixture and mixed by pipette up and down 3 times. Sf9 cells were plated on 6-well plate at density of $1.5×10^6$ cells/well in 2 mL ESF AF media and incubated at 28° C. in an incubator for about 30 min to attach. The media from each well was removed and the GenJet-bacmid mixture was then added. After incubation at 28° C. in the incubator overnight, 1 mL of ESF AF media was added and the plate was incubated at 28° C. for a total of 4 days for recombinant baculovirus to be generated. The recombinant baculoviruses in the media were collected and stored at 4° C. under dark.

The recombinant baculoviruses generated from DH10Bac-wt and DH10Bac-Δv-cath were designated as WT-rBV, and Δv-cath rBV, respectively.

Example 4

Impact of v-cath Deletion on rBV Replication

To determine if deletion of the v-cath gene affected replication of baculovirus, three pairs of WT-rBV and Δv-cath rBV were used. The first pair WT-rBV-Cap6-Rep and Δv-cath-rBV-Cap6-Rep each carries AAV6 capsid gene encoding VP1, VP2, and VP3 and AAV2 rep gene encoding rep78 and rep52. The second pair WT-rBV-GFP and Δv-cath rBV-GFP each carries GFP gene encoding the green fluorescent protein. The third pair WT-rBV-Cap7m8-Rep and Δv-cath rBV-Cap7m8-Rep each carries AAV7m8 capsid gene encoding VP1, VP2, and VP3 and AAV2 rep gene encoding rep78 and rep52.

All the rBVs generated were used to infect Sf9 cells for amplification. Briefly, 1 mL of each rBV was added to 200 mL of Sf9 cells at density of $2 \times 10^6$ cells/mL in a Corning culture bottle, respectively, and the rBV amplification was carried out for 3 days at 28° C. and 180 rpm in a shaker incubator (New Brunswick, Hauppauge, N.Y.). The supernatants were harvested by centrifugation at 2,000 rpm for 10 min to remove the cell pellets. The rBV titers in the supernatants were determined by the quantitative polymerase chain reaction (QPCR) method as described in EXAMPLE 5.

Example 5

Quantification of rBV

To determine the titers of recombinant baculoviruses, a specific QPCR method for rBV titration developed in Virovek was employed. Briefly, 50 µl rBV supernatant was mixed with 50 µL 0.2% SDS solution and heated at 95° C. for 30 min to release the rBV DNA. The rBV DNA was diluted 1:100 with QPCR dilution buffer (10 µg/mL yeast tRNA (Sigma Aldrich, Saint Louis, Mo.), 0.01% Tween 80, 10 mM Tris-HCl (pH 8.0), 1 mM EDTA) and the copy numbers of rBV were determined with Chromo 4 Four-Color Real-time Detection System (Bio-Rad, Hercules, Calif.) using primers corresponding to the gentamicin gene (3065: 5'-ATTTGACTTGGTCAGGGCCG-3'9 (SEQ ID NO:8) and 3066: 5'-TGTTACGCAGCAGGGCAGTC-3' (SEQ ID. NO:9)) and SYBR Green PCR Master Mix (ThermoFisher Scientific, Fremont, Calif.). One plaque forming unit (pfu) was empirically determined to contain average of 20 copies of rBV genomes.

Example 6

AAV Vector Production and Purification

Recombinant baculoviruses were used to infect insect cells to produce AAV vectors. Briefly, 10 moi of recombinant baculovirus containing AAV Rep and Cap genes were co-infected with 5 moi of recombinant baculovirus containing the GFP marker gene flanked by AAV ITRs for 3 days at 28° C. Cell pellets were collected by centrifugation at 3000 rpm for 10 min. The cell pellets were lysed in SF9 lysis buffer (50 mM Tris-HCl, pH 7.8, 50 mM NaCl, 2 mM $MgCl_2$, 1% Sarkosyl, 1% Triton X-100, and 140 units/mL Benzonase nuclease (Sigma Aldrich) by sonication. Cell debris was removed by centrifugation at 8,000 rpm for 20 min. The cleared lysates of about 23 mL each were transferred to ultraclear centrifuge tubes for SW28 rotor (Beckman Coulter, Brea, Calif.), followed by 10 mL of 1.32 g/cc and 5 mL of 1.55 g/cc CsCl solutions and centrifuged at 28,000 rpm at 15° C. for about 20 hours. The AAV vector band was visualized with a beam light shining underneath and collected with a syringe needle. The collected AAV vectors were transferred into another centrifuge tube for a 70.1 ti rotor (Beckman Coulter) which was then filled with 1.38 g/cc CsCl solution and sealed. After centrifugation at 65,000 rpm for about 20 hours, the AAV vector band was visualized with a beam light shining underneath and collected with a syringe needle. The AAV vectors were buffer exchanged with PD-10 desalting columns (GE Healthcare Bio-Sciences, Pittsburgh, Pa.). After filter sterilization, the AAV vectors were used for further experiments.

Example 7

AAV Vector Quantification

AAV vectors in crude lysates or in purified form were quantified with QPCR according to protocol described by Aurnhamme et al. (*Hum. Gene Ther. Meth.* (2012) 23(1): 18-28) with modifications. Briefly, AAV samples were first diluted 1:100 with QPCR dilution buffer and contaminating DNA was removed by incubating 10 µl diluted AAV with 1 µl (2 units) DNaseI enzyme (New England Biolabs) in 39 µl DNaseI digestion buffer (10 mM Tris-HCl, pH 8.0, 2.5 mM $MgCl_2$, 0.5 mM $CaCl_2$) at 37° C. for 1 hour. The DNase I enzyme was inactivated by mixing with 50 µl of 200 mM EDTA and heating at 95° C. for 30 min. The treated AAV samples were further diluted 1:200, and 10 µl of each AAV sample was used in the Chromo4 QPCR machine (Bio-Rad, Hercules, Calif.) to determine the copy numbers of AAV vector genome.

Example 8

Preservation of Capsid Integrity in Δv-cath rBV-Produced AAV Vectors

AAV vectors were produced by co-infection of Sf9 cells with Δv-cath rBVs or WT-rBV and purified by two rounds of cesium chloride ultracentrifugation as described in EXAMPLE 6. Equal amounts ($1 \times 10^{11}$ vg) of purified AAV particles were heated at 95° C. for 5 min. Capsid proteins were separated by SDS-PAGE and stained with a Simply Blue staining kit to determine the amount of degradation, if any, of the capsid proteins produced by each type of rBV.

Example 9

Infectivity of rBV-Produced AAV Vectors

AAV vectors produced in Sf9 cells with Δv-cath rBVs or WT-rBVs were purified and quantified as described above in EXAMPLE 7. These AAV vectors were used to transduce HEK-293 cells for comparison of their infectivities. The HEK-293 cells (ATCC-CRL-1573, Manassas, Va.) were cultured in DMEM media (Mediatech, Manassas, Va.) supplemented with 100 units of Penicillin-Streptomycin (Corning, Corning, N.Y.) with 10% FBS (Hyclone, Logan, Utah) in Corning 12-well cell culture plate in a $CO_2$ incubator at 37° C. until about 70% confluent. The AAV samples were diluted each in 1 mL of DMEM containing 20 μm etoposide (A.G. Scientific, San Diego, Calif.) but without FBS to obtain 3.0e+9 vg/mL. After the old media was removed from the plate, 0.5 mL of diluted AAV sample was added to each well, and the plate was incubated in the $CO_2$ incubator at 37° C. overnight. The next morning, 0.5 mL DMEM medium containing 20% FBS and 100 units of Penicillin-Streptomycin was added to each well, and the transduction was carried out for 2 to 3 days. GFP-expressing cells were recorded with the Nikon Eclipse TS100 fluorescence microscope (Nikon Instruments, Melville, N.Y.).

Example 10

Expression of SV40 Capsid Proteins in Δv-cath rBV-Infected Insect Cells

Recombinant baculovirus carrying SV40 capsid genes was used to infect insect cells to express the SV40 capsid proteins. Briefly, 10 moi of the recombinant baculovirus were added to 300 mL Sf9 cells and incubated for 3 days at 28° C. Cell pellets were collected by centrifugation at 3000 rpm for 10 min. The cell pellets were lysed in SF9 lysis buffer (50 mM Tris-HCl, pH 7.8, 50 mM NaCl, 2 mM $MgCl_2$, 1% Sarkosyl, 1% Triton X-100, and 140 units/mL Benzonase nuclease (Sigma Aldrich) by sonication. Cell debris was removed by centrifugation at 8,000 rpm for 20 min. The cleared lysate of about 23 mL was transferred to ultraclear centrifuge tube for SW28 rotor (Beckman Coulter, Brea, Calif.), followed by 10 mL of 1.32 g/cc and 5 mL of 1.55 g/cc CsCl solutions and centrifuged at 28,000 rpm at 15° C. for about 20 hours. The SV40 virus-like band was visualized with a beam light shining underneath and collected with a syringe needle. The collected SV40 virus-like particles were transferred into another centrifuge tube for a 70.1 ti rotor (Beckman Coulter) which was then filled with 1.38 g/cc CsCl solution and sealed. After centrifugation at 65,000 rpm for about 20 hours, the SV40 virus-like particle band was visualized with a beam light shining underneath and collected with a syringe needle. The SV40 virus-like particles were buffer exchanged with PD-10 desalting columns (GE Healthcare Bio-Sciences, Pittsburgh, Pa.). After filter sterilization, the SV40 virus-like articles were used for further experiments.

Example 11

Expression of Human Antibody Heavy and Light Chains in Δv-cath rBV-Infected Insect Cells Recombinant baculovirus carrying the human antibody heavy chain and light chain expression cassettes was used to infect Sf9 cells for protein expression. Briefly, 10 moi of rBVs were used to infect 300 mL Sf9 cells for 3 days at 28° C. and both supernatant and cell pellet were harvested respectively. The cell pellet was lysed in the Sf9 lysis buffer, as described in EXAMPLE 6, and the cleared lysate was collected. Expressed human antibody in the supernatant and lysate were purified with protein-A agarose and analyzed by SDS-PAGE.

Example 12

Removal of the Selection Marker Expression Cassette by FLP/FLPe Expression

Two versions of cathepsin-deleted baculovirus DNA backbones were constructed: one with the CAT expression cassette flanked by two FRTs and the other with the CAT expression cassette flanked by two FRTs plus the GFP expression cassette integrated into the cathepsin-deletion region.

To remove the CAT expression cassette between FRT sites from the baculovirus backbone, the following experiment was performed. Glycerol stocks of bacteria containing DH10Bac-Δcath were streak on an LB plate containing 10 μg/mL tetracycline and 25 μg/mL chloramphenicol and were grown overnight (ON) at 37° C. The following evening a well-grown colony was picked and grown ON in 1 mL LB media containing 10 μg/mL tetracycline and 25 μg/mL chloramphenicol at 37° C. with agitation. The following morning, 30 μL of the ON culture was diluted into 1.4 mL of LB media containing 10 μg/mL tetracycline and 25 μg/mL chloramphenicol and grown at 37° C. to an $OD_{600}$ of between 0.3-0.5. The cell pellet was collected by centrifugation at 11,000 rpm for 30 sec. After removing the supernatant, the cell pellet was put on ice and resuspended in 1 mL ice-cold 10% glycerol. The cell pellet was centrifuged again at 11,000 rpm for 30 sec to remove most of the supernatant, leaving 20-30 μL in the tube to resuspend the cell pellet. One μL (500 ng/μL) of plasmid pCP20, containing the FLP recombinase (The ODIN, Oakland, Calif.) was added to the resuspended cells kept on ice and mixed briefly. The cells were then transferred to a chilled electroporation cuvette (Molecular Bioproducts, Inc., Cat #5510-11, Fischer Scientific) and electroporated with the "Bacteria" Setting on the BioRad MicroPulser machine (Hercules, Calif.). After electroporation, the cells were added to 1 mL LB media without antibiotics, and incubated at 30° C. for 2 hr with agitation. One hundred μL of the cell solution was plated on an LB plate containing 100 μg/mL ampicillin (Thermo Fisher Scientific, Waltham, Mass.), 50 μg/mL kanamycin (Thermo Fisher Scientific, Waltham, Mass.), and 10 μg/mL tetracycline (Thermo Fisher Scientific, Waltham, Mass.), and cultured at 30° C. ON. Eleven well-grown colonies were picked, streaked on an LB plate without antibiotics, and cultured at 43° C. ON. to express the recombinase, which removed the chloramphenicol expression cassettes located between 2 FRT sites through recombination. The next morning, bacteria from each colony were removed with a pipette tip and resuspended in 20 μL cold Milli Q-purified (Millipore Sigma) water.

PCR reactions were performed to verify the removal of the DNA sequence between the 2 FRT sites using 2 μL resuspended bacteria from each colony. Forward primer 6298 (5'-TAATAAATGACTGCAGTAGACGCAA-3') (SEQ ID NO: 5), and reverse primer 6299 (5'-GAACAAAATTTTGTTTTATTTGTTTGTGTA-3') (SEQ ID NO:6) were used to verify the removal of the CAT expression cassette from DH10Bac-Δv-cath containing the CAT expression cassette flanked by two FRTs plus the GFP expression cassette. Forward primer 2847 (5'-CTACGAGCGCATAATTGCGA-3') (SEQ ID NO:10) and reverse primer 2848 (5'-GTTTGGTCATGTAGT-TAACTTTG-3') (SEQ ID NO:11) were used to verify the removal of the CAT expression cassette from DH10Bac-Δv-cath containing only the FRT flanked CAT expression cassette. The PCR condition shown below in Table 2 were used.

TABLE 2

| Step | Temperature | Time |
| --- | --- | --- |
| Initial Denaturation | 98° C. | 30 seconds |
| 32 Cycles | 98° C. | 10 Seconds |

21

TABLE 2-continued

| Step | Temperature | Time |
|---|---|---|
| | 58° C. | 20 Seconds |
| | 72° C. | 1 Minute 30 Seconds |
| Final Extension | 72° C. | 2 Minutes |
| Hold | 4° C. | As Needed |

Figure 14A:
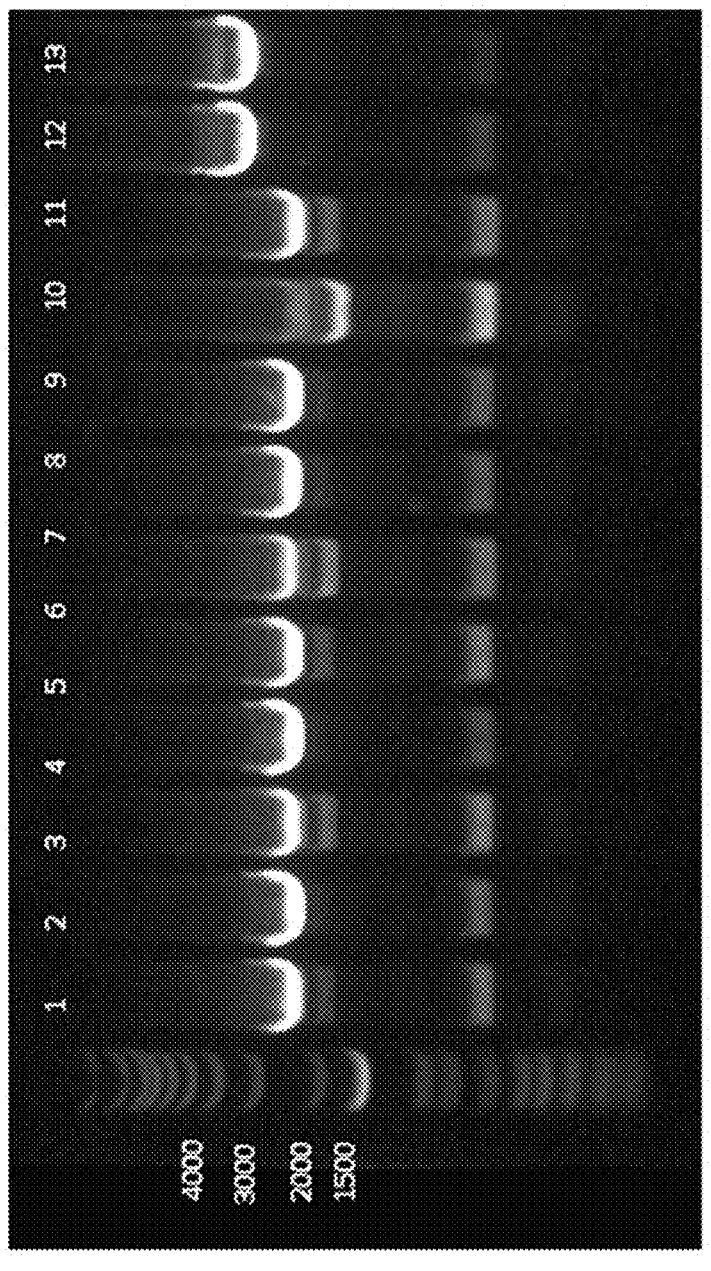
FIG. 14A is a photographic representation of an agarose gel electrophoresis image showing the removal of the CAT expression cassette from the Δv-cath rBV backbone, wherein smaller PCR fragments (2,345 bps) in lanes 1-11, compared to lanes 12 and 13 (3,245 bps), indicates the removal of the CAT expression cassette from the Δv-cath rBV backbone containing both the CAT and GFP expression cassettes.

After the PCR reactions, the amplified PCR fragments were electrophoresed on a 1% agarose gel. As shown in FIG. 14A, for DH10Bac-Δv-cath containing the CAT and the GFP expression cassettes, the PCR fragments from the 11 colonies have a fragment size of 2346 bps, whereas the control colonies #12, and #13 have a fragment size of 3276 bps, indicating that the CAT expression cassette (930 bps) had been remove from colonies 1-11. DNA sequencing analysis further confirmed the removal of the CAT expression cassette, leaving the FRT (minimal) sequence and the GFP expression cassette in the v-cath deletion region (FIGS. 15A-15D).

Figure 14B:
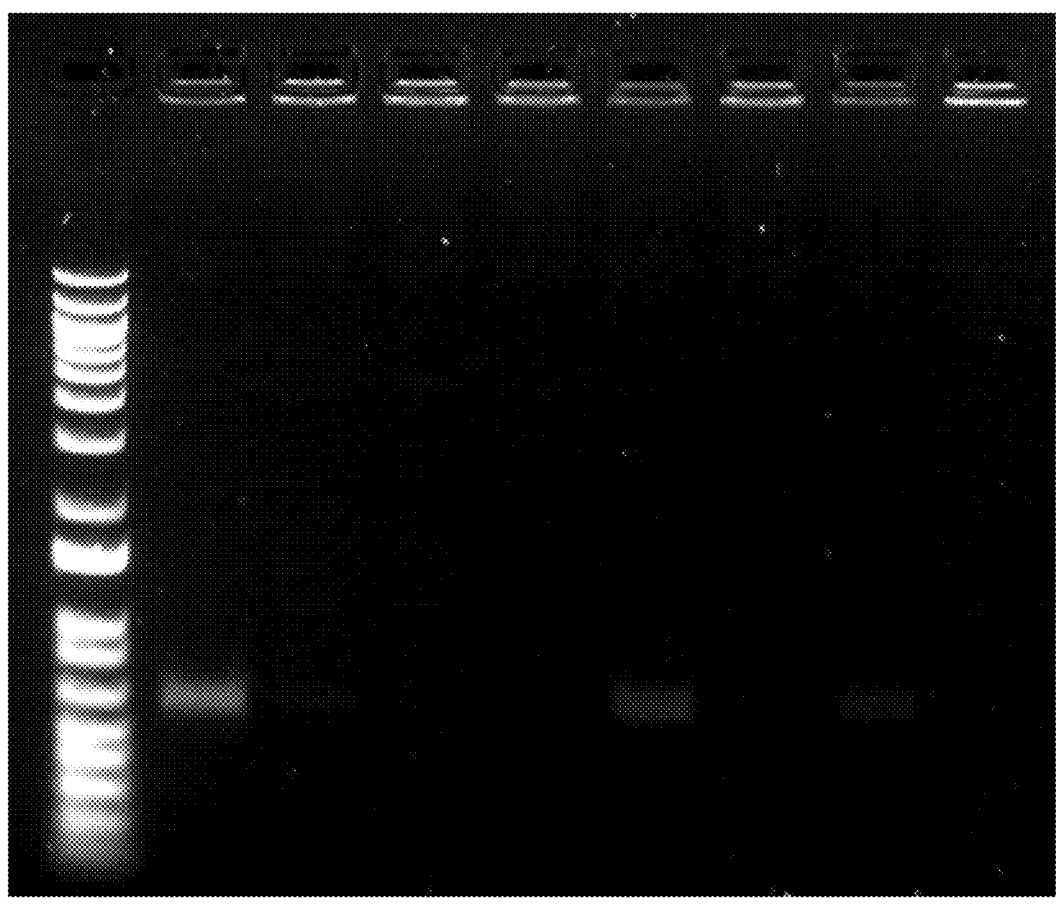
FIG. 14B, is a photographic representation of an agarose gel electrophoresis image showing the removal of the CAT expression cassette from the Δv-cath rBV backbone, wherein a 651-bp PCR fragment is shown in lanes 1, 5, and 7, indicating the correct fragment size after the removal of the CAT expression cassette from the Δv-cath rBV backbone with only one FRT site left behind.
Figure 15A:
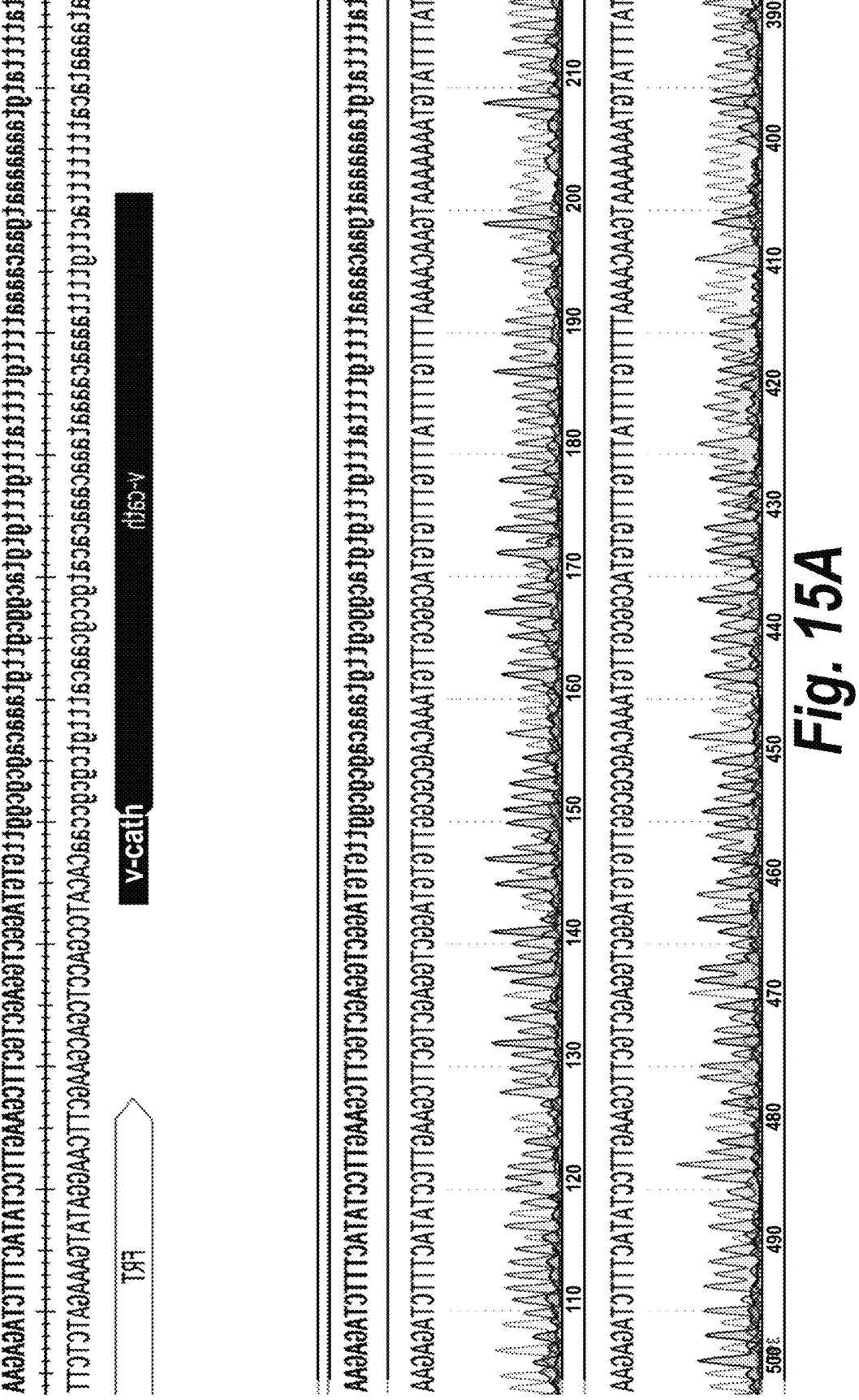
FIGS. 15A-15D are schematic representations of a DNA sequencing analysis showing the removal of the CAT expression cassette from (FIG. 15A: SEQ ID NO:14) the Δv-cath rBV backbone containing both the CAT and the GFP expression cassettes, and (FIG. 15B: SEQ ID NO:15) the Δv-cath rBV backbone containing only the CAT expression cassette.
Figure 15B:
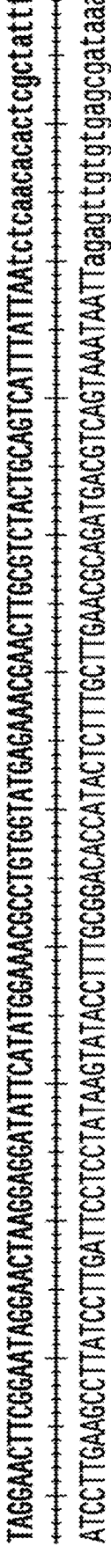
Figure 15B:
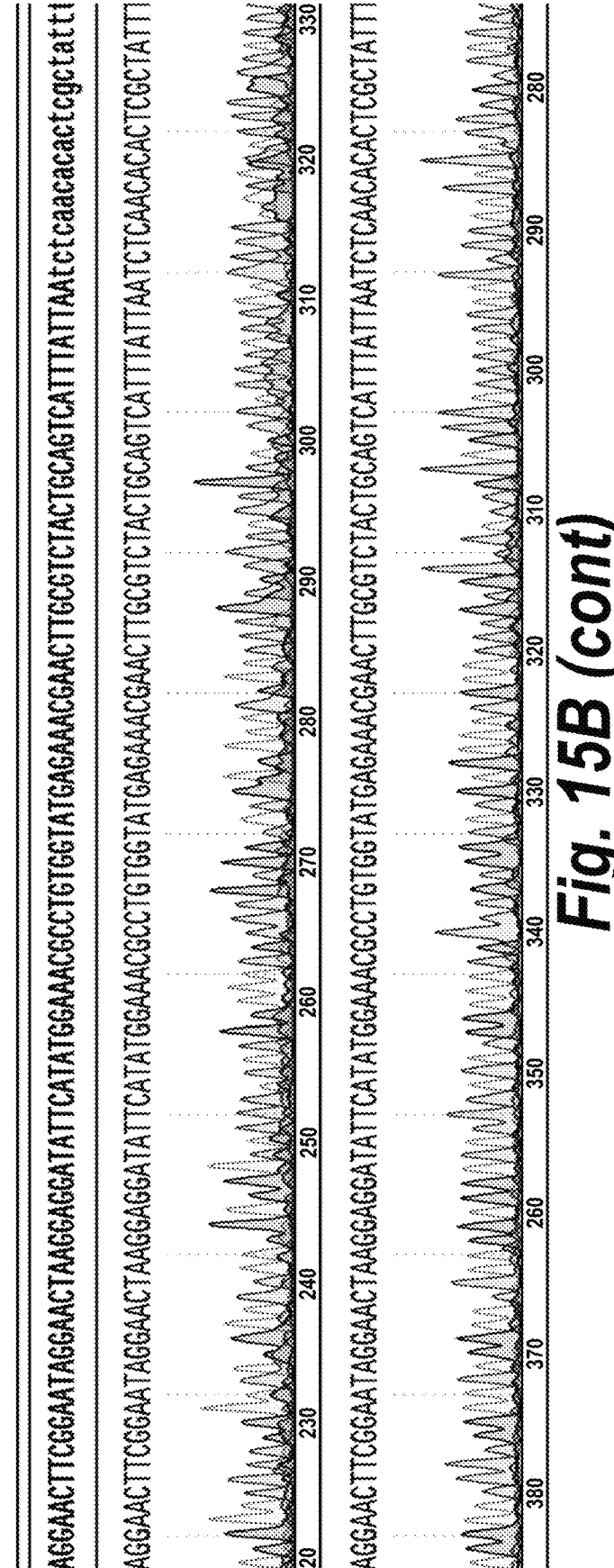
Figure 15C:
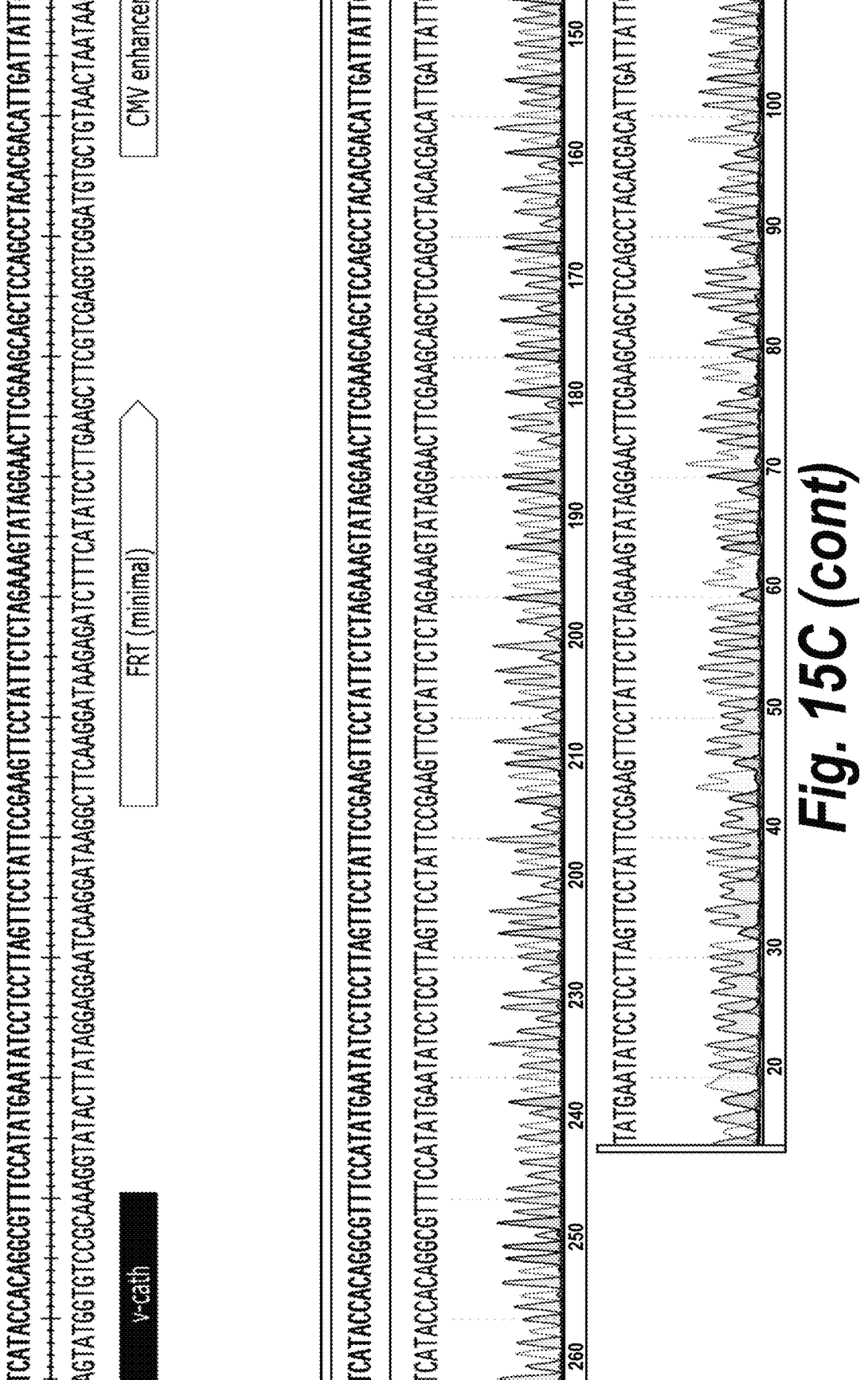
Figure 15D:
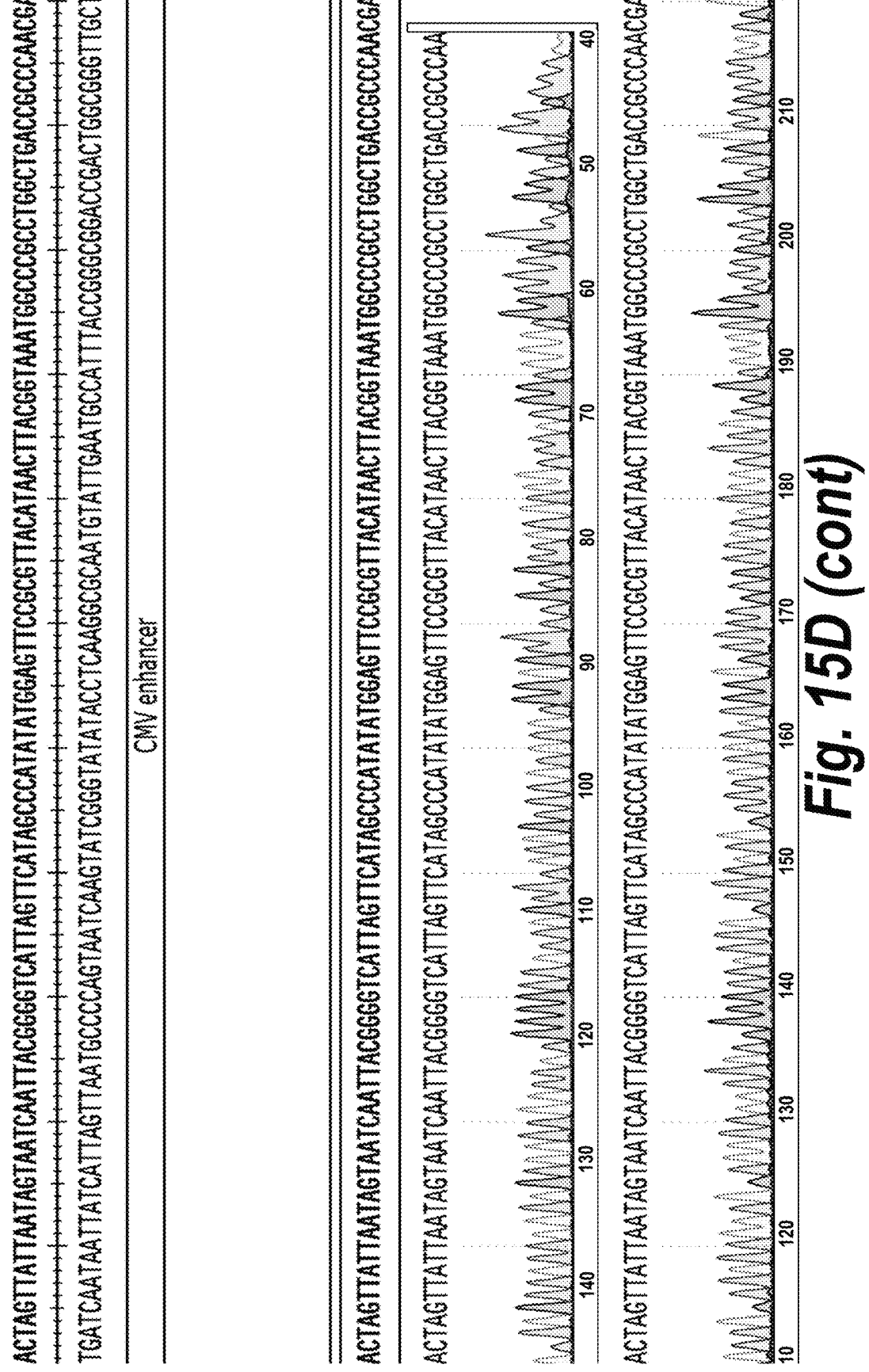

For DH10Bac-Δv-cath containing only the CAT expression cassette flanked by two FRTs, from the 8 colonies that had undergone the removal process only 3 colonies (#1, #5, and #7) showed PCR amplification of a fragment size of 651 bps, indicating the removal of CAT expression cassette (FIG. 14B). DNA sequencing analysis further confirmed the removal of the CAT expression cassette, leaving only the FRT sequence in the v-cath deletion region (FIGS. 15A-15D).

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

---

The invention claimed is:

1. A recombinant baculovirus (rBV) genome comprising an rBV DNA backbone, wherein the rBV DNA backbone comprises:
   (i) a chitinase gene;
   (ii) a deletion of a v-cath gene, and
   (iii) a DNA fragment enabling integration of one or more protein expression cassettes into the rBV DNA backbone, wherein the one or more protein expression cassettes comprise:
   at least one gene comprising a sequence encoding an AAV capsid protein,
   an insect cell promoter operably linked to the at least one gene, and
   two DNA sequences enabling the one or more protein expression cassettes to integrate into the rBV DNA backbone; and
   upon infection of the rBV genome into an insect cell, AAV vectors are produced at a level about 3 times greater as compared to AAV vectors produced from an rBV DNA backbone without a deletion of the v-cath gene.

2. The rBV genome of claim 1, wherein the DNA fragment of the rBV DNA backbone comprises a DNA sequence homologous to two sequences flanking the one or more protein expression cassettes in a donor plasmid.

3. The rBV genome of claim 1, wherein the DNA fragment of the rBV DNA backbone is derived from bMON14272.

4. The rBV genome of claim 3, wherein the DNA fragment of the rBV DNA backbone comprises an origin of replication.

5. The rBV genome of claim 3, wherein the DNA fragment of the rBV DNA backbone further comprises a reporter gene.

6. The rBV genome of claim 1, wherein the rBV DNA backbone further comprises a selection marker expression gene cassette integrated into the v-cath deletion.

7. The rBV genome of claim 1, wherein the two DNA sequences enabling the one or more protein expression cassettes to integrate into the rBV DNA backbone are homologous to the DNA sequences in the rBV DNA backbone or are transposable elements.

8. A recombinant baculovirus (rBV) vector or particle comprising:
   the rBV genome of claim 1; and
   at least one baculoviral capsid protein.

9. An isolated insect cell comprising the rBV vector or particle of claim 8.

10. The insect cell of claim 9, further comprising at least one AAV capsid protein expressed from the one or more protein expression cassettes in the rBV DNA backbone of the rBV genome.

11. A heterologous expression system comprising:
   the rBV vector or particle of claim 8; and
   an insect cell susceptible to infection and capable of expressing at least one AAV capsid protein encoded by the rBV DNA backbone in the rBV vector or particle.

12. A non-viscous insect cell lysate, comprising:
   the rBV genome of claim 1; and
   at least one AAV capsid protein encoded by the rBV DNA backbone and expressed in the lysate.

13. The rBV genome of claim 1, wherein the DNA fragment enabling integration of one or more protein expression cassettes into the rBV DNA backbone comprises a transposon fragment.

14. The rBV genome of claim 1, wherein the one or more protein expression cassettes comprise sequences encoding AAV capsid proteins VP1, VP2, and VP3, and upon infection of the rBV genome into an insect cell, AAV vectors are produced at a level about 4 times greater as compared to AAV vectors produced from an rBV DNA backbone without a deletion of the v-cath gene.

* * * * *

SEQUENCE LISTING

```
<160> NUMBER OF SEQ ID NOS: 15

<210> SEQ ID NO 1
<211> LENGTH: 71
<212> TYPE: DNA
<213> ORGANISM: Artificial Sequence
<220> FEATURE:
<223> OTHER INFORMATION: Synthetic polynucleotide sequence.

<400> SEQUENCE: 1
taataaatga ctgcagtaga cgcaagttcg tttctcatac cacaggcgtt tccatatgaa     60
tatcctcctt a                                                           71

<210> SEQ ID NO 2
<211> LENGTH: 46
<212> TYPE: DNA
<213> ORGANISM: Artificial Sequence
<220> FEATURE:
<223> OTHER INFORMATION: Synthetic polynucleotide sequence.

<400> SEQUENCE: 2
ataactagtc aataatcaat gtcgtgtagg ctggagctgc ttcgaa                     46

<210> SEQ ID NO 3
<211> LENGTH: 30
<212> TYPE: DNA
<213> ORGANISM: Artificial Sequence
<220> FEATURE:
<223> OTHER INFORMATION: Synthetic polynucleotide sequence.

<400> SEQUENCE: 3
gacattgatt attgactagt tattaatagt                                       30

<210> SEQ ID NO 4
<211> LENGTH: 72
<212> TYPE: DNA
<213> ORGANISM: Artificial Sequence
<220> FEATURE:
<223> OTHER INFORMATION: Synthetic polynucleotide sequence.

<400> SEQUENCE: 4
gaacaaaatt ttgttttatt tgtttgtgta cggcgttgta aacagcgcgg ttagatccag     60
acatgataag at                                                          72
```

-continued

```
<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide sequence.

<400> SEQUENCE: 5
taataaatga ctgcagtaga cgcaa                                      25

<210> SEQ ID NO 6
<211> LENGTH: 30
<212> TYPE: DNA
<213> ORGANISM: Artificial Sequence
<220> FEATURE:
<223> OTHER INFORMATION: Synthetic polynucleotide sequence.

<400> SEQUENCE: 6
gaacaaaatt ttgttttatt tgtttgtgta                                 30

<210> SEQ ID NO 7
<211> LENGTH: 70
<212> TYPE: DNA
<213> ORGANISM: Artificial Sequence
<220> FEATURE:
<223> OTHER INFORMATION: Synthetic polynucleotide sequence.

<400> SEQUENCE: 7
gaacaaaatt ttgttttatt tgtttgtgta cggcgttgta aacagcgcgg ttgtgtaggc    60
tggagctgct                                                       70

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide sequence.

<400> SEQUENCE: 8
atttgacttg gtcagggccg                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide sequence.

<400> SEQUENCE: 9
tgttacgcag cagggcagtc                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide sequence.

<400> SEQUENCE: 10
ctacgagcgc ataattgcga                                            20

<210> SEQ ID NO 11
<211> LENGTH: 23
<212> TYPE: DNA
<213> ORGANISM: Artificial Sequence
<220> FEATURE:
```

<223> OTHER INFORMATION: Synthetic polynucleotide sequence.

<400> SEQUENCE: 11
gtttggtcat gtagttaact ttg                                                    23

<210> SEQ ID NO 12
<211> LENGTH: 3275
<212> TYPE: DNA
<213> ORGANISM: Artificial Sequence
<220> FEATURE:
<223> OTHER INFORMATION: Synthetic polynucleotide sequence.

<400> SEQUENCE: 12
taataaatga ctgcagtaga cgcaagttcg tttctcatac cacaggcgtt tccatatgaa       60
tatcctcctt agttcctatt ccgaagttcc tattctctag aaagtatagg aacttcggcg      120
cgcctacctg tgacggaaga tcacttcgca gaataaataa atcctggtgt ccctgttgat      180
accgggaagc cctgggccaa cttttggcga aaatgagacg ttgatcggca cgtaagaggt      240
tccaactttc accataatga aataagatca ctaccgggcg tattttttga gttgtcgaga      300
ttttcaggag ctaaggaagc taaaatggag aaaaaaatca ctggatatac caccgttgat      360
atatcccaat ggcatcgtaa agaacatttt gaggcatttc agtcagttgc tcaatgtacc      420
tataaccaga ccgttcagct ggatattacg gcctttttaa agaccgtaaa gaaaaataag      480
cacaagtttt atccggcctt tattcacatt cttgcccgcc tgatgaatgc tcatccggaa      540
ttacgtatgg caatgaaaga cggtgagctg gtgatatggg atagtgttca cccttgttac      600
accgtttttc catgagcaaac tgaaacgttt tcatcgctct ggagtgaata ccacgacgat      660
ttccggcagt ttctacacat atattcgcaa gatgtggcgt gttacggtga aaacctggcc      720
tatttcccta aagggtttat tgagaatatg tttttcgtct cagccaatcc ctgggtgagt      780
ttcaccagtt ttgatttaaa cgtggccaat atggacaact tcttcgcccc cgttttcacc      840
atgggcaaat attatacgca aggcgacaag gtgctgatgc cgctggcgat tcaggttcat      900
catgccgttt gtgatggctt ccatgtcggc agatgcttaa tgaatacaac agtactgcga      960
tgagtggcag ggcggggcgt aaggcgcgcc atttaaatga agttcctatt ccgaagttcc     1020
tattctctag aaagtatagg aacttcgaag cagctccagc ctacacgaca ttgattattg     1080
actagttatt aatagtaatc aattacgggg tcattagttc atagcccata tatggagttc     1140
cgcgttacat aacttacggt aaatggcccg cctggctgac cgcccaacga cccccgccca     1200
ttgacgtcaa taatgacgta tgttcccata gtaacgccaa tagggacttt ccattgacgt     1260
caatgggtgg agtatttacg gtaaactgcc cacttggcag tacatcaagt gtatcatatg     1320
ccaagtccgc cccctattga cgtcaatgac ggtaaatggc ccgcctggca ttatgcccag     1380
tacatgacct tacgggactt tcctacttgg cagtacatct acgtattagt catcgctatt     1440
accatggtga tgcggttttg gcagtacacc aatgggcgtg gatagcggtt tgactcacgg     1500
ggatttccaa gtctccaccc cattgacgtc aatgggagtt tgttttggca ccaaaatcaa     1560
cgggactttc caaaatgtcg taataacccc gccccgttga cgcaaatggg cggtaggcgt     1620
gtacggtggg aggtctatat aagcagagct cgtttagtga accgtcagaa ttttgtaata     1680
cgactcacta tagggcggcc gggaattcgc accatggtg agcaagggcg aggagctgtt     1740
caccggggtg gtgcccatcc tggtcgagct ggacggcgac gtaaacggcc acaagttcag     1800
cgtgtccggc gagggcgagg gcgatgccac ctacggcaag ctgaccctga agttcatctg     1860
caccaccggc aagctgcccg tgccctggcc caccctcgtg accaccctga cctacggcgt     1920

```
gcagtgcttc agccgctacc ccgaccacat gaagcagcac gacttcttca agtccgccat    1980
gcccgaaggc tacgtccagg agcgcaccat cttcttcaag gacgacggca actacaagac    2040
ccgcgccgag gtgaagttcg agggcgacac cctggtgaac cgcatcgagc tgaagggcat    2100
cgacttcaag gaggacggca acatcctggg gcacaagctg gagtacaact acaacagcca    2160
caacgtctat atcatggccg acaagcagaa gaacggcatc aaggtgaact tcaagatccg    2220
ccacaacatc gaggacggca gcgtgcagct cgccgaccac taccagcaga caccccccat    2280
cggcgacggc cccgtgctgc tgcccgacaa ccactacctg agcacccagt ccgccctgag    2340
caaagacccc aacgagaagc gcgatcacat ggtcctgctg gagttcgtga ccgccgccgg    2400
gatcactctc ggcatggacg agctgtacaa gtaactcgag aatcaacctc tggattacaa    2460
aatttgtgaa agattgactg gtattcttaa ctatgttgct ccttttacgc tatgtggata    2520
cgctgcttta atgcctttgt atcatgctat tgcttcccgt atggctttca ttttctcctc    2580
cttgtataaa tcctggttgc tgtctcttta tgaggagttg tggcccgttg tcaggcaacg    2640
tggcgtggtg tgcactgtgt ttgctgacgc aacccccact ggttggggca ttgccaccac    2700
ctgtcagctc ctttccggga ctttcgcttt ccccctccct attgccacgg cggaactcat    2760
cgccgcctgc cttgcccgct gctggacagg ggctcggctg ttgggcactg acaattccgt    2820
ggtgttgtcg gggaagctga cgtcctttcc atggctgctc gcctgtgttg ccacctggat    2880
tctgcgcggg acgtccttct gctacgtccc ttcggccctc aatccagcgg accttccttc    2940
ccgcggcctg ctgccggctc tgcggcctct tccgcgtctt cgcctccgcc ctcagacgag    3000
tcggatctcc ctttgggccg cctccccgcg gtacccaatt cgccctatag tgagtcgtat    3060
tacgcgcgca gcggccgacc atggcccaac ttgtttattg cagcttataa tggttacaaa    3120
taaagcaata gcatcacaaa tttcacaaat aaagcatttt tttcactgca ttctagttgt    3180
ggtttgtcca aactcatcaa tgtatcttat catgtctgga tctaaccgcg ctgtttacaa    3240
cgccgtacac aaacaaataa aacaaaattt tgttc                                3275
```

```
<210> SEQ ID NO 13
<211> LENGTH: 7107
<212> TYPE: DNA
<213> ORGANISM: Artificial Sequence
<220> FEATURE:
<223> OTHER INFORMATION: Synthetic polynucleotide sequence.

<400> SEQUENCE: 13
tgtgggcgga caataaagtc ttaaactgaa caaaatagat ctaaactatg acaataaagt      60
cttaaactag acagaatagt tgtaaactga aatcagtcca gttatgctgt gaaaaagcat     120
actggacttt tgttatggct aaagcaaact cttcattttc tgaagtgcaa attgcccgtc     180
gtattaaaga ggggcgtggc caagggcatg gtaaagacta tattcgcggc gttgtgacaa     240
tttaccgaac aactccgcgg ccgggaagcc gatctcggct tgaacgaatt gttaggtggc     300
ggtacttggg tcgatatcaa agtgcatcac ttcttcccgt atgcccaact ttgtatagag     360
agccactgcg ggatcgtcac cgtaatctgc ttgcacgtag atcacataag caccaagcgc     420
gttggcctca tgcttgagga gattgatgag cgcggtggca atgccctgcc tccggtgctc     480
gccggagact gcgagatcat agatatagat ctcactacgc ggctgctcaa acctgggcag     540
aacgtaagcc gcgagagcgc caacaaccgc ttcttggtcg aaggcagcaa gcgcgatgaa     600
tgtcttacta cggagcaagt cccgaggta atcggagtcc ggctgatgtt gggagtaggt     660
```

-continued

```
ggctacgtct ccgaactcac gaccgaaaag atcaagagca gcccgcatgg atttgacttg      720
gtcagggccg agcctacatg tgcgaatgat gcccatactt gagccaccta actttgtttt      780
agggcgactg ccctgctgcg taacatcgtt gctgctgcgt aacatcgttg ctgctccata      840
acatcaaaca tcgacccacg gcgtaacgcg cttgctgctt ggatgcccga ggcatagact      900
gtacaaaaaa acagtcataa caagccatga aaaccgccac tgcgccgtta ccaccgctgc      960
gttcggtcaa ggttctggac cagttgcgtg agcgcatacg ctacttgcat tacagtttac     1020
gaaccgaaca ggcttatgtc aactgggttc gtgccttcat ccgtttccac ggtgtgcgtc     1080
acccggcaac cttgggcagc agcgaagtcg aggcatttct gtcctggctg gcgaacgagc     1140
gcaaggtttc ggtctccacg catcgtcagg cattggcggc cttgctgttc ttctacggca     1200
aggtgctgtg cacggatctg ccctggcttc aggagatcgg tagacctcgg ccgtcgcggc     1260
gcttgccggt ggtgctgacc ccggatgaag tggttcgcat cctcggtttt ctggaaggcg     1320
agcatcgttt gttcgcccag gactctagct atagttctag tggttggcct acgtacccgt     1380
agtggctatg gcagggcttg ccgccccgac gttggctgcg agccctgggc cttcacccga     1440
acttgggggt tggggtgggg aaaaggaaga aacgcgggcg tattggtccc aatggggtct     1500
cggtggggta tcgacagagt gccagccctg ggaccgaacc ccgcgtttat gaacaaacga     1560
cccaacaccc gtgcgtttta ttctgtcttt ttattgccgt catagcgcgg gttccttccg     1620
gtattgtctc cttccgtgtt tcagttagcc tcccccatct cccggtaccg catgctcctt     1680
cagagagagt gtcctcgagc caatctgaaa caataccatc ggcagccata cctgatttaa     1740
atcatttatt gttcaaagat gcagtcatcc aaatccacat tgaccagatc gcaggcagtg     1800
caagcgtctg gcacctttcc catgatatga tgaatgtagc acagtttctg atacgccttt     1860 ttgacgcacag aaacgggttg agattctgac acgggaaagc actctaaaca gtctttctgt     1920
ccgtgagtga agcagatatt tgaattctga ttcattctct cgcattgtct gcagggaaac     1980
agcatcagat tcatgcccac gtgacgagaa catttgtttt ggtacctgtc tgcgtagttg     2040
atcgaagctt ccgcgtctga cgtcgatggc tgcgcaactg actcgcgcac ccgtttgggc     2100
tcacttatat ctgcgtcact gggggcgggt ctttttcttgg ctccacccctt tttgacgtag     2160 aattcatgct ccacctcaac cacgtgatcc tttgcccacc ggaaaaagtc tttgacttcc     2220
tgcttggtga ccttcccaaa gtcatgatcc agacggcggg tgagttcaaa tttgaacatc     2280
cggtcttgca acggctgctg gtgttcgaag gtcgttgagt tcccgtcaat cacggcgcac     2340
atgttggtgt tggaggtgac gatcacggga gtcgggtcta tctgggccga ggacttgcat     2400
ttctggtcca cgcgcacctt gcttcctccg agaatggctt tggccgactc cacgaccttg     2460
gcggtcatct tcccctcctc ccaccagatc accatcttgt cgacacagtc gttgaaggga     2520
aagttctcat tggtccagtt tacgcacccg tagaagggca cagtgtgggc tatggcctcc     2580
gcgatgttgg tcttcccggt agttgcaggc ccaaacagcc agatggtgtt cctcttgccg     2640
aactttttcg tggcccatcc cagaaagacg gaagccgcat attggggatc gtaccgtttt     2700
agttccaaaa tttttataaat ccgattgctg gaaatgtcct ccacgggctg ctggcccacc     2760
aggtagtcgg gggcggtttt agtcaggctc ataatctttc ccgcattgtc caaggcagcc     2820
ttgatttggg accgcgagtt ggaggccgca ttgaaggaga tgtatgaggc ctggtcctcc     2880
tggatccact gcttctccga ggtaatcccc ttgtccacga gccacccgac cagctccatg     2940
tacctggctg aagttttttga tctgatcacc ggcgcatcag aattgggatt ctgattctct     3000
ttgttctgct cctgcgtctg cgacacgtgc gtcagatgct gcgccaccaa ccgtttacgc     3060
```

```
tccgtgagat tcaaacaggc gctgaaacaa taggaaggga gtggatgtca gtgtgtgctg   3120 cccggggggct ctgactacag gtctccccct tcgcgcccga tggtgggacg gtatgaataa  3180
tccggaatat ttataggttt ttttattaca aaactgttac gaaaacagta aaatacttat   3240
ttatttgcga gatggttatc attttaatta tctccatgat agatctctat cactgatagg   3300
gagtacttac cttaaatact gttccatatt agtccacgcc cactggagct caggctgggt   3360
tttggggagc aagtaattgg ggatgtagca ctcatccacc accttgttcc cgcctccggc   3420
gccatttctg gtctttgtga ccgcgaacca gtttggcaaa gtcggctcga tcccgcggta   3480
aattctctga atcagttttt cgcgaatctg actcaggaaa cgtcccaaaa ccatggattt   3540 cacccggtg gtttccacga gcacgtgcat gtggaagtag ctctctccct tctcaaattg     3600
cacaaagaaa agggcctccg gggccttact cacacggcgc cattccgtca gaaagtcgcg    3660
ctgcagcttc tcggccacgg tcaggggtgc ctgctcaatc agattcagat ccatgtcaga   3720
atctggcggc aactcccatt ccttctcggc cacccagttc acaaagctgt cagaaatgcc   3780
gggcagatgc tcgtcaaggt cgctggggac cttaatcaca atctcgtaaa accccggcat   3840
ggcgggtagg gtgatcaagt cttcgtcgag tgattgtaaa taaaatgtaa tttacagtat   3900
agtattttaa ttaatataca aatgatttga taataattct tatttaacta taatatattg   3960
tgttgggttg aattaaaggt ccgtagcttt cgaatctagg ctcaagcagt gatcagatcc   4020
agacatgata agatacattg atgagtttgg acaaaccaca actagaatgc agtgaaaaaa   4080
atgctttatt tgtgaaattt gtgatgctat tgctttattt gtaaccatta taagctgcaa   4140
taaacaagtt aacaacaaca attgcattca ttttatgttt caggttcagg gggaggtgtg    4200
ggaggttttt taaagcaagt aaaacctcta caaatgtggt atggctgatt atgatcctct   4260
agtacttctc gacaagcttg tcgagactgc aggctctaga ttacagatta cgagtcaggt   4320
atctggtgcc aatggggcga ggctctgaat acacgccatt agtgtccaca gtaaagtcca   4380
cattaacaga cttgttgtag ttggaagtgt actgaatttc gggattccag cgtttgctgt   4440
tttccttctg cagctcccac tcgatctcca cgctgacctg tcccgtggag tactgtgtga   4500
tgaaggaagc aaactttgcc gcactgaagg tggtcgaagg attcgcaggt accggggtgt    4560
tcttgatgag aatctgtgga ggagggtgtt taagtccgaa tccacccatg aggggagagg   4620
ggtgaaaatg tccgtccgtg tgtggaatct ttgcccagat gggcccctga aggtacacat    4680
ctctgtcctg ccagaccatg cctggaagaa cgccttgtgt gttgacatct gcggtagctg   4740
cttgcctagc aggtcttgtt gtttcgccga gtgctaggtt gcctctctgg aggttggtag    4800
atacagaacc atactgctcc gtagccacgg gattggttgt cctgatttcc tcttcgtctg   4860
taatcatgac ctttttcaatg tccacatttg ttttctctga gccttgcttc ccaaagatga   4920
gaaccccgct ctgaggaaaa aacttttctt catcgtcctt gtggcttgcc atggccgggc   4980
ccggattcac cagagagtct ctgccattga ggtggtactt ggtagctcca gtccacgagt    5040
attcactgtt gttgttatcc gcagatgtct ttgatactcg ctgctggcgg taacagggtc   5100
caggaagcca gttcctagac tggtcccgaa tgtcactcgc tccggcctga gaaaactgaa   5160
gccttgactg cgtggtggtt ccacttggag tgtttgttct gctcaagtaa tacaggtact   5220
ggtcgatgag aggattcatg agacggtcca gactctggct gtgagcgtag ctgctgtgga   5280
aaggaacgtc ctcaaaagtg tagctgaagg taaagttgtt tccggtacgc agcatctgag   5340
aaggaaagta ctccaggcag taaaatgaag agcgtcctac tgcctgactc ccgttgttca   5400
```

-continued

```
gggtgaggta tccatactgt ggcaccatga agacgtctgc tgggaacggc gggaggcatc    5460
cttgatgcgc cgagccgagg acgtacggga gctggtactc cgagtcagta aacacctgaa    5520
ccgtgctggt aaggttattg gcaatcgtcg tcgtaccgtc attctgcgtg acctctttga    5580
cttgaatgtt aaagagcttg aagttgagtc tcttgggtcg gaatccccag ttgttgttga    5640
tgagtctttg ccagtcacgt ggtgaaaagt ggcagtggaa tctgttgaag tcaaaatacc    5700
cccaaggggt gctgtagcca aagtagtgat tgtcgttcga ggctcctgat tggctggaaa    5760
tttgtttgta gaggtggttg ttgtaggtgg gcagggccca ggttcgggtg ctggtggtga    5820
tgactctgtc gcccatccat gtggaatcgc aatgccaatt tcccgaggaa ttacccactc    5880
cgtcggcgcc ctcgttattg tctgccattg gtgcgccact gcctgtagcc atcgtattag    5940
ttcccagacc agaggggggct gctggtggct gtccgagagg ctgggggtca ggtactgagt    6000
ctgcgtctcc agtctgacca aaattcaatc ttttttcttgc aggctgctgg cccgcctttc    6060
cggttcccga ggaggagtct ggctccacag gagagtgctc taccggcctc tttttttcccg    6120 gagccgtctt aacaggttcc tcaaccaggc ccagaggttc aagaaccctc tttttcgcct    6180
ggaagactgc tcgtccgagg ttgcccccaa aagacgtatc ttctttaagg cgctcctgaa    6240
actccgcgtc ggcgtggttg tacttgaggt acgggttgtc tccgctgtcg agctgccggt    6300
cgtaggcttt gtcgtgctcg agggccgcgg cgtctgcctc gttgaccggc tctcccttgt    6360
cgagtccgtt gaagggtccg aggtacttgt acccaggaag cacaagaccc ctgctgtcgt    6420
ccttatgccg ctctgcgggc tttggtggtg gtgggccagg tttgagcttc caccactgtc    6480
ttattccttc agagagagtg tcctcgagcc aatctgaaac aataggaagg gagtggatgt    6540
cagtgtgtgc tgcccggggg ctctgactac aggtctcccc cttcgcgccc gatggtggga    6600
cggtatgaat aatccggaat atttataggt tttttatta caaaactgtt acgaaaacag    6660
taaaatactt atttatttgc gagatggtta tcattttaat tatctccatg atagatctct    6720
atcactgata gggagtactt acctggaaga taaccatcgg cagccatggt ggcggatccg    6780
cgcccgatgg tgggacggta tgaataatcc ggaatattta taggtttttt tattacaaaa    6840
ctgttacgaa aacagtaaaa tacttatttta tttgcgagat ggttatcatt ttaattatct    6900
ccatgatcta ttaatattcc ggagtatacc taggagatcc gaaccagata agtgaaatct    6960
agttccaaac tattttgtca tttttaattt tcgtattagc ttacgacgct acacccagtt    7020
cccatctatt ttgtcactct tccctaaata atccttaaaa actccatttc cacccctccc    7080
agttcccaac tattttgtcc gcccaca                                        7107
```

```
<210> SEQ ID NO 14
<211> LENGTH: 195
<212> TYPE: DNA
<213> ORGANISM: Artificial Sequence
<220> FEATURE:
<223> OTHER INFORMATION: Synthetic polynucleotide sequence.

<400> SEQUENCE: 14
taataaatga ctgcagtaga cgcaagttcg tttctcatac cacaggcgtt tccatatgaa      60
tatcctcctt agttcctatt ccgaagttcc tattctctag aaagtatagg aacttcgaag     120
cagctccagc ctacacgaca ttgattattg actagttatt aatagtaatc aattacgggg     180
tcattagttc atagc                                                      195
```

```
<210> SEQ ID NO 15
<211> LENGTH: 188
```

-continued

```
<212> TYPE: DNA
<213> ORGANISM: Artificial Sequence
<220> FEATURE:
<223> OTHER INFORMATION: Synthetic polynucleotide sequence.

<400> SEQUENCE: 15
aaatgaacaa aattttgttt tatttgtttg tgtacggcgt tgtaaacagc gcggttgtgt          60
aggctggagc tgcttcgaag ttcctatact ttctagagaa taggaacttc ggaataggaa         120
ctaaggagga tattcatatg gaaacgcctg tggtatgaga aacgaacttg cgtctactgc         180
agtcattt                                                                  188
```